US010696648B2

(12) United States Patent
Williams et al.

(10) Patent No.: US 10,696,648 B2
(45) Date of Patent: Jun. 30, 2020

(54) INHIBITORS OF INDOLEAMINE 2,3-DIOXYGENASE AND METHODS OF THEIR USE

(71) Applicant: BRISTOL-MYERS SQUIBB COMPANY, Princeton, NJ (US)

(72) Inventors: David K. Williams, Princeton, NJ (US); Weifang Shan, Princeton, NJ (US); James Aaron Balog, Princeton Junction, NJ (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 16/098,239

(22) PCT Filed: May 4, 2017

(86) PCT No.: PCT/US2017/030992
§ 371 (c)(1),
(2) Date: Nov. 1, 2018

(87) PCT Pub. No.: WO2017/192811
PCT Pub. Date: Nov. 9, 2017

(65) Prior Publication Data
US 2019/0144416 A1 May 16, 2019

Related U.S. Application Data

(60) Provisional application No. 62/331,849, filed on May 4, 2016.

(51) Int. Cl.
| | | |
|---|---|---|
| *C07D 401/10* | (2006.01) | |
| *C07C 275/30* | (2006.01) | |
| *C07C 275/36* | (2006.01) | |
| *C07C 275/34* | (2006.01) | |
| *C07C 275/28* | (2006.01) | |
| *C07C 275/42* | (2006.01) | |
| *C07C 275/26* | (2006.01) | |
| *A61P 35/00* | (2006.01) | |
| *A61K 31/4709* | (2006.01) | |
| *A61K 31/47* | (2006.01) | |
| *A61K 31/277* | (2006.01) | |
| *A61K 31/17* | (2006.01) | |
| *C07D 401/04* | (2006.01) | |
| *C07D 215/18* | (2006.01) | |
| *C07C 275/32* | (2006.01) | |

(52) U.S. Cl.
CPC ........... *C07D 401/04* (2013.01); *A61K 31/17* (2013.01); *A61K 31/277* (2013.01); *A61K 31/47* (2013.01); *A61K 31/4709* (2013.01); *A61P 35/00* (2018.01); *C07C 275/26* (2013.01); *C07C 275/28* (2013.01); *C07C 275/30* (2013.01); *C07C 275/32* (2013.01); *C07C 275/34* (2013.01); *C07C 275/36* (2013.01); *C07C 275/42* (2013.01); *C07D 215/18* (2013.01); *C07C 2601/02* (2017.05); *C07C 2601/08* (2017.05); *C07C 2601/14* (2017.05)

(58) Field of Classification Search
CPC ..... A61P 35/00; C07C 275/34; C07C 275/26; C07C 275/28; C07C 275/30; C07C 275/32; C07C 275/36; C07C 275/42; C07C 2601/02; C07C 2601/08; C07C 2601/14; A61K 31/4709; A61K 31/47; A61K 31/277; A61K 31/17; C07D 401/04; C07D 215/18
See application file for complete search history.

(56) References Cited

U.S. PATENT DOCUMENTS

| | | | | |
|---|---|---|---|---|
| 3,424,760 A | * | 1/1969 | Welstead, Jr. | ........ C07D 207/14 548/557 |
| 4,123,529 A | | 10/1978 | Verge et al. | |
| 6,288,230 B1 | | 9/2001 | Chen et al. | |
| 8,088,803 B2 | | 1/2012 | Combs et al. | |
| 2003/0114517 A1 | * | 6/2003 | Greenlee | ............... C07C 275/30 514/438 |
| 2004/0072818 A1 | * | 4/2004 | Dunning | .............. C07D 215/46 514/210.21 |
| 2006/0258719 A1 | | 11/2006 | Combs et al. | |
| 2016/0022619 A1 | | 1/2016 | Balog et al. | |
| 2016/0137653 A1 | | 5/2016 | Beck et al. | |

FOREIGN PATENT DOCUMENTS

| | | | |
|---|---|---|---|
| WO | 99/29310 | A2 | 6/1999 |
| WO | 2004/094409 | A1 | 11/2004 |
| WO | 2006/029879 | A2 | 3/2006 |
| WO | 2006/105021 | A2 | 10/2006 |
| WO | 2006/122150 | A1 | 11/2006 |

(Continued)

OTHER PUBLICATIONS

Vlahos et al., "A specific inhibitor of phosphatidyleinositol 3-kinase, 2-(4-morpholinyl)-8-phenyl-4H-1-benzopyran-4-one (LY294002)", J. Biol. Chem, Feb. 18, 1994, 269(7), 5241-5248.

(Continued)

*Primary Examiner* — Alexander R Pagano
*Assistant Examiner* — Ebenezer O Sackey
(74) *Attorney, Agent, or Firm* — BakerHostetler

(57) ABSTRACT

There are disclosed compounds that modulate or inhibit the enzymatic activity of indoleamine 2,3-dioxygenase (IDO), pharmaceutical compositions containing said compounds and methods of treating proliferative disorders, such as cancer, viral infections and/or inflammatory disorders utilizing the compounds of the invention.

20 Claims, No Drawings

(56) References Cited

FOREIGN PATENT DOCUMENTS

| WO | 2007/005874 | A2 | 1/2007 |
|---|---|---|---|
| WO | 2007/075598 | | 7/2007 |
| WO | 2008/036642 | | 3/2008 |
| WO | 2008/036653 | | 3/2008 |
| WO | 2008/132601 | A1 | 11/2008 |
| WO | 2009/009116 | A2 | 1/2009 |
| WO | 2009/044273 | A2 | 4/2009 |
| WO | 2009/056652 | | 5/2009 |
| WO | 2009/073620 | | 6/2009 |
| WO | 2010/019570 | A2 | 2/2010 |
| WO | 2010/077634 | A1 | 7/2010 |
| WO | 2011/028683 | A1 | 3/2011 |
| WO | 2011/056652 | A1 | 5/2011 |
| WO | 2011/070024 | A1 | 6/2011 |
| WO | 2011/107553 | A1 | 9/2011 |
| WO | 2011/131407 | A1 | 10/2011 |
| WO | 2011/140249 | A2 | 11/2011 |
| WO | 2012/032433 | A1 | 3/2012 |
| WO | 2012/142237 | A1 | 10/2012 |
| WO | 2012/145493 | A1 | 10/2012 |
| WO | 2013/079174 | A1 | 6/2013 |
| WO | 2013/087699 | A1 | 6/2013 |
| WO | 2013/119716 | A1 | 8/2013 |
| WO | 2013/132044 | A1 | 9/2013 |
| WO | 2013/169264 | A1 | 11/2013 |
| WO | 2014/008218 | A1 | 1/2014 |
| WO | 2014/036357 | A1 | 3/2014 |
| WO | 2015/006520 | A1 | 1/2015 |
| WO | 2016/073738 | A2 | 5/2016 |
| WO | 2016/073770 | A1 | 5/2016 |
| WO | 2016/073774 | A2 | 5/2016 |

OTHER PUBLICATIONS

Serafini et al., "Myeloid suppressor cells in cancer: recruitment, phenotype, properties, and mechanisms of immune suppression", In Seminars in Cancer Biol., Feb. 1, 2006, 16(1), 53-65.
Sekulic et al., "A direct linkage between the phosphoinositide 3-kinase-AKT signaling pathway and the mammalian target of rapamycin in mitogen-stimulated and transformed cells", Cancer Res., Jul. 1, 2000, 60(13), 3504-3513.
Scheller et al., "Paclitaxel Balloon Coating, A Novel Method for Prevention and Therapy of Restenosis", Circulation, Aug. 17, 2004, 110(7), 810-814.
Sausville et al., "Cyclin-dependent kinase modulators studied at the NCI: pre-clinical and clinical studies", Curr. Med. Chem. Anti-Cancer Agents, Jan. 1, 2003, 3(1), 47-56.
Sarkar et al., "Induction of Indoleamine 2, 3-dioxygenase by interferon-? in human islets", Diabetes, Jan. 1, 2007, 56(1), 72-79.
Sambrook et al., "Molecular Cloning", Third Edition, Cold Spring Harbor Laboratory Press, © 2001, 21 pages.
Notari, Theory and Practice of Prodrug Kinetics, Methods in Enzymology, Academic Press, 1985, 112, 309-396.
Nielsen et al., "Glycolamide esters as biolabile prodrugs of carboxylic acid agents: synthesis, stability, bioconversion, and physicochemical properties", J. Pharm. Sci., Apr. 1988, 77(4), 285-298.
Littlejohn et al., "Expression and purification of recombinant human indoleamine 2, 3-dioxygenase", Prot. Exp. and Purif, Jun. 1, 2000, 19(1), 22-29.
Kohl et al., "Inhibition of farnesyltransferase induces regression of mammary and salivary carcinomas in ras transgenic mice", Nat. Med., Aug. 1995, 1(8), 792-797.
Kakeya et al., Studies on Prodrugs of Cephalosporins. I. Synthesis and Biological Properties of Glycyloxybenzoyloxymethyl and Glycylaminobenzoyloxymethyl Esters of 7B-[2-(2-Aminothiazol-4-yl)-(Z)-2-methoxyiminoacetamido]-3-methyl-3-cephem-4-carboxylic Acid, Chem. Pharm. Bull., Feb. 25, 1984, 32(2), 692-698.
Ishiyama, et al., Palladium (0)-catalyzed cross-coupling reaction of alkoxydiboron with haloarenes: a direct procedure for arylboronic esters, The Journal of Org. Chem., Nov. 1995, 60(23), 7508-7510.
Goldstein et al., "Biological efficacy of a chimeric antibody to the epidermal growth factor receptor in human tumor xenograft model", Clin. Cancer Res., Nov. 1, 1995, 1(11): 1311-1318.
Bundgaard, H.(C) Means to enhance penetration: (1) Prodrugs as a means to improve the delivery of peptide drugs, Adv. Drug Deilv. Rev., Jan. 1, 1992, 8(1), 1-38.
Bundgaard, H. Chapter 5: "Design and Application or Produgs", A Textbook of Drug Design and Development, pp. 113-191, Krogsgaard-Larsen, P. et al., eds., Harwood Academic Publishers, 1991.
Bundgaard, "Design of Prodrugs: Bioreversible derivatives for various functional groups and chemical entities", 1985, Design of Prodrugs, 1985, 96 pages.
Brandacher, et al., Prognostic value of indoleamine 2, 3-dioxygenase expression in colorectal cancer: effect on tower-infiltrating T cells, Clin. Cancer Res., Feb. 15, 2006, 12(4), 1144-1151.
Ball, H.J. et al., Characterization of an indoleamine 2, 3-dioxygenase-like protein found in humans and mice, Gene, Jul. 1, 2007, 396(1), 203-213.

\* cited by examiner

INHIBITORS OF INDOLEAMINE 2,3-DIOXYGENASE AND METHODS OF THEIR USE

CROSS-REFERENCE TO RELATED APPLICATIONS

This application is the National Stage Application of International Patent Application No. PCT/US2017/030992 filed May 4, 2017, which claims the benefit of U.S. Provisional Application No. 62/331,849, filed May 4, 2016. Each of these applications is incorporated by reference herein in its entirety.

FIELD OF THE INVENTION

The invention relates generally to compounds that modulate or inhibit the enzymatic activity of indoleamine 2,3-dioxygenase (IDO), pharmaceutical compositions containing said compounds and methods of treating proliferative disorders, such as cancer, viral infections and/or autoimmune diseases utilizing the compounds of the invention.

BACKGROUND OF THE INVENTION

Indoleamine 2,3-dioxygenase (IDO; also known as IDO1) is an IFN-γ target gene that plays a role in immunomodulation. IDO is an oxidoreductase and one of two enzymes that catalyze the first and rate-limiting step in the conversion of tryptophan to N-formylkynurenine. It exists as a 41 kD monomer that is found in several cell populations, including immune cells, endothelial cells, and fibroblasts. IDO is relatively well-conserved between species, with mouse and human sharing 63% sequence identity at the amino acid level. Data derived from its crystal structure and site-directed mutagenesis show that both substrate binding and the relationship between the substrate and iron-bound dioxygenase are necessary for activity. A homolog to IDO (IDO2) has been identified that shares 44% amino acid sequence homology with IDO, but its function is largely distinct from that of IDO. (See, e.g., Serafini, P. et al., *Semin. Cancer Biol.*, 16(1):53-65 (February 2006) and Ball, H. J. et al., Gene, 396(1):203-213 (Jul. 1, 2007)).

IDO plays a major role in immune regulation, and its immunosuppressive function manifests in several manners. Importantly, IDO regulates immunity at the T cell level, and a nexus exists between IDO and cytokine production. In addition, tumors frequently manipulate immune function by upregulation of IDO. Thus, modulation of IDO can have a therapeutic impact on a number of diseases, disorders and conditions.

A pathophysiological link exists between IDO and cancer. Disruption of immune homeostasis is intimately involved with tumor growth and progression, and the production of IDO in the tumor microenvironment appears to aid in tumor growth and metastasis. Moreover, increased levels of IDO activity are associated with a variety of different tumors (Brandacher, G. et al., *Clin. Cancer Res.*, 12(4):1144-1151 (Feb. 15, 2006)).

Treatment of cancer commonly entails surgical resection followed by chemotherapy and radiotherapy. The standard treatment regimens show highly variable degrees of long-term success because of the ability of tumor cells to essentially escape by regenerating primary tumor growth and, often more importantly, seeding distant metastasis. Recent advances in the treatment of cancer and cancer-related diseases, disorders and conditions comprise the use of combination therapy incorporating immunotherapy with more traditional chemotherapy and radiotherapy. Under most scenarios, immunotherapy is associated with less toxicity than traditional chemotherapy because it utilizes the patient's own immune system to identify and eliminate tumor cells.

In addition to cancer, IDO has been implicated in, among other conditions, immunosuppression, chronic infections, and autoimmune diseases or disorders (e.g., rheumatoid arthritis). Thus, suppression of tryptophan degradation by inhibition of IDO activity has tremendous therapeutic value. Moreover, inhibitors of IDO can be used to enhance T cell activation when the T cells are suppressed by pregnancy, malignancy, or a virus (e.g., HIV). Although their roles are not as well defined, IDO inhibitors may also find use in the treatment of patients with neurological or neuropsychiatric diseases or disorders (e.g., depression).

Small molecule inhibitors of IDO have been developed to treat or prevent IDO-related diseases. For example, the IDO inhibitors 1-methyl-DL-tryptophan; p-(3-benzofuranyl)-DL-alanine; p-[3-benzo(b)thienyl]-DL-alanine; and 6-nitro-L-tryptophan have been used to modulate T cell-mediated immunity by altering local extracellular concentrations of tryptophan and tryptophan metabolites (WO 99/29310). Compounds having IDO inhibitory activity are further reported in PCT Publication No. WO 2004/094409.

In view of the role played by indoleamine 2,3-dioxygenase in a diverse array of diseases, disorders and conditions, and the limitations (e.g., efficacy) of current IDO inhibitors, new IDO modulators, and compositions and methods associated therewith, are needed.

SUMMARY OF THE INVENTION

The invention is directed to compounds of formula I or formula II:

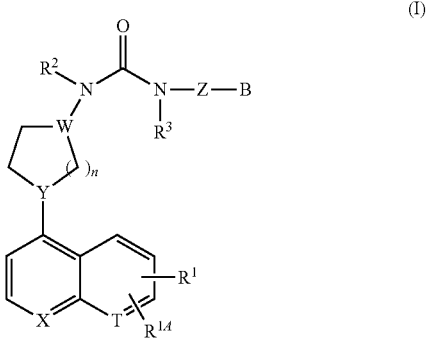

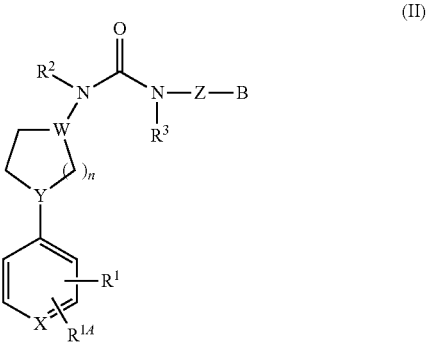

wherein X is CH or N; T is CH or N; $R^1$ is H, halo, or $C_1$-$C_6$haloalkyl; $R^{1A}$ is H, halo, or $C_1$-$C_6$haloalkyl; Y is CH or N; W is —CH—, —C($C_1$-$C_6$alkyl)-, or N; n is 0, 1, 2, 3, or 4; $R^2$ is $C_1$-$C_6$alkyl or -alkaryl optionally substituted with —O$C_1$-$C_6$alkyl, —$C_1$-$C_6$alkCOOH, or —$C_1$-$C_6$alkCOO$C_1$-$C_6$alkyl; $R^3$ is H or $C_1$-$C_6$alkyl; Z is a bond or $C_1$-$C_6$alkylene optionally substituted with one, two, or three $R^4$ substituents independently selected from $C_1$-$C_6$alkyl; and B is aryl optionally substituted with 1, 2, or 3 substituents independently selected from —OH, $C_1$-$C_6$alkyl, $C_1$-$C_6$haloalkyl, halo, —O$C_1$-$C_6$alkyl, —O$C_1$-$C_6$haloalkyl, —CN, aryl, or —Oaryl; or B is $C_3$-$C_{12}$cycloalkyl optionally substituted with 1, 2, or 3 substituents independently selected from —OH, $C_1$-$C_6$alkyl, $C_1$-$C_6$haloalkyl, halo, —O$C_1$-$C_6$alkyl, —O$C_1$-$C_6$haloalkyl, —CN, aryl, or —Oaryl.

Also within the scope of the invention are pharmaceutically acceptable salts, stereoisomers, tautomers, and solvates of the compounds of formula I and formula II.

The invention is also directed to pharmaceutical compositions comprising one or more compounds of formula I and/or formula II. The invention is also directed to methods of treating, e.g., cancer using one or more compounds of formula I and/or formula II.

DETAILED DESCRIPTION OF THE INVENTION

Compounds of the Invention

The invention is directed to compounds of formula I and formula II:

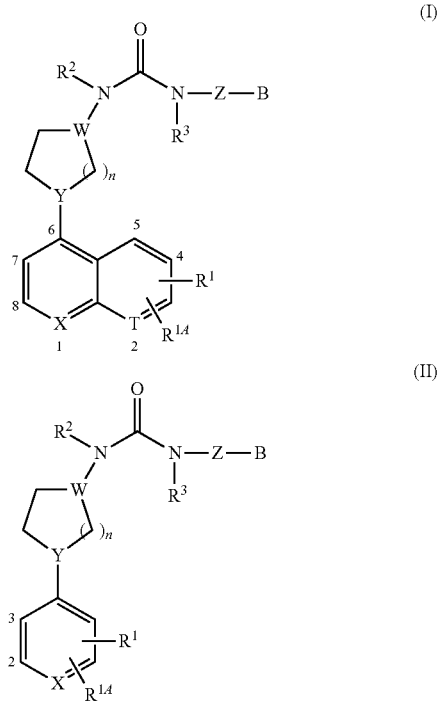

According to the disclosure, X is CH or N. In some embodiments, X is CH. In other embodiments, X is N.

According to the disclosure T is CH or N. In some aspects, T is CH. In other aspects, T is N.

In some embodiments of formula I, X is CH and T is CH. In other embodiments, X is N and T is CH. In other embodiments, X is CH and T is N. In other embodiments, X is N and T is N.

According to the disclosure, $R^1$ is H, halo, or $C_1$-$C_6$haloalkyl. In other aspects, $R^1$ is H, halo, $C_1$-$C_6$alkyl, or $C_1$-$C_6$haloalkyl. In some aspects, $R^1$ is H. In some aspects, $R^1$ is halo (F, Cl, Br, or I), preferably F. In other aspects, $R^1$ is $C_1$-$C_6$alkyl, for example, methyl, ethyl, isopropyl, butyl, and t-butyl. In yet other aspects, $R^1$ is $C_1$-$C_6$haloalkyl, for example, —$CF_3$. In some aspects, $R^1$ is halo, $C_1$-$C_6$alkyl, or $C_1$-$C_6$haloalkyl. In other aspects, $R^1$ is halo or $C_1$-$C_6$haloalkyl.

In those aspects of the disclosure comprising compounds of formula I, when $R^1$ is halo, $C_1$-$C_6$alkyl, or $C_1$-$C_6$haloalkyl, the $R^1$ is preferably present at the 4-carbon position of the ring. In other aspects of the disclosure comprising compounds of formula I, when $R^1$ is halo, $C_1$-$C_6$alkyl, or $C_1$-$C_6$haloalkyl, the $R^1$ can be present at the 2-carbon position of the ring. Preferably, in those aspects of the disclosure comprising compounds of formula I, $R^1$ is F or $CF_3$ at the 4-carbon position of the ring.

In those aspects of the disclosure comprising compounds of formula II, when $R^1$ is halo, $C_1$-$C_6$alkyl, or $C_1$-$C_6$haloalkyl, the $R^1$ is preferably present at the 2-carbon position of the phenyl or pyridyl ring. In other aspects of the disclosure comprising compounds of formula II, when $R^1$ is halo, $C_1$-$C_6$alkyl, or $C_1$-$C_6$haloalkyl, the $R^1$ can be present at the 3-carbon position of the phenyl or pyridyl ring. Preferably, in those aspects of the disclosure comprising compounds of formula II, $R^1$ is F or $CF_3$ at the 2-carbon position of the phenyl or pyridyl ring.

According to the disclosure, $R^{1A}$ is H, halo, $C_1$-$C_6$alkyl, or $C_1$-$C_6$haloalkyl. In preferred aspects, $R^{1A}$ is H. In some aspects, $R^{1A}$ is halo (F, Cl, Br, or I). In other preferred aspects, $R^{1A}$ is $C_1$-$C_6$alkyl, for example, methyl, ethyl, isopropyl, butyl, and t-butyl. In yet other aspects, $R^{1A}$ is $C_1$-$C_6$haloalkyl, for example, —$CF_3$.

According to the disclosure, Y is CH or N. In some aspects, Y is CH. In other aspects, Y is N. In alternative embodiments, Y is —C($C_1$-$C_6$alkyl), for example, —C($CH_3$)— or C($CH_2CH_3$).

According to the disclosure, W is CH, —C($C_1$-$C_6$alkyl)-, or N. In some aspects, W is CH. In other aspects, W is —C($C_1$-$C_6$alkyl)-, for example, —C($CH_3$)—, —C($CH_2CH_3$)—, —C(i-propyl), or —C(butyl)-. In other aspects, W is N. In some aspects, W is CH or —C($C_1$-$C_6$alkyl)-. In other aspects, W is CH or N. In yet other aspects, W is N or —C($C_1$-$C_6$alkyl)-.

In some aspects, Y is CH and W is CH. In other aspects, Y is CH and W is N. In other aspects, Y is N and W is CH. In still other aspects, Y is N and W is N. In some aspects, Y is CH and W is C($C_1$-$C_6$alkyl). In other aspects, Y is N and W is C($C_1$-$C_6$alkyl).

According to the disclosure, n is 0, 1, 2, 3, or 4. In preferred aspects, n is 2. In other aspects, n is 0. In other aspects, n is 1. In yet other aspects, n is 3. In still other aspects, n is 4. In some aspects, n is 0 to 2 or 1 to 2. In yet other aspects, n is 1 to 3.

According to the disclosure, $R^2$ is $C_1$-$C_6$alkyl or -alkaryl optionally substituted with —O$C_1$-$C_6$alkyl, $C_1$-$C_6$alkCOOH, or —$C_1$-$C_6$alkCOO$C_1$-$C_6$alkyl. In some aspects, $R^2$ is H. In some aspects, $R^2$ is $C_1$-$C_6$alkyl, for example, methyl, ethyl, propyl, isopropyl, butyl, s-butyl, t-butyl, pentyl, or hexyl. In other aspects, $R^2$ is unsubstituted alkaryl, for example, $C_1$-$C_3$alk-phenyl, preferably, benzyl (—$CH_2$-phenyl). In other aspects $R^2$ is substituted -alkaryl, for example, substituted $C_1$-$C_3$alk-phenyl, preferably, benzyl (—$CH_2$-phenyl). In some embodiments, $R^2$ is -alkaryl substituted with —$OC_1$-$C_6$alkyl, for example, substituted with methoxy, ethoxy, propoxy, isoproxy, butoxy, or t-butoxy.

In still other aspects, $R^2$ is -alkaryl substituted with —$C_1$-$C_6$alkCOOH, for example, substituted with —$C_1$-$C_{56}$alkCOOH, —$C_1$-$C_4$alkCOOH, —$C_1$-$C_3$alkCOOH, —$C_1$-$C_2$alkCOOH, or —$C_1$alkCOOH. In still other aspects, $R^2$ is -alkaryl substituted with —$C_1$-$C_6$alkCOO$C_1$-$C_6$alkyl, for example, substituted with —$C_1$-$C_5$alkCOO$C_1$-$C_6$alkyl, —$C_1$-$C_4$alkCOO$C_1$-$C_6$alkyl, —$C_1$-$C_3$alkCOO$C_1$-$C_6$alkyl, —$C_1$-$C_2$alkCOO$C_1$-$C_6$alkyl, —$C_1$alkCOO$C_1$-$C_6$alkyl, —$C_1$-$C_6$alkCOO$C_1$-$C_5$alkyl, —$C_1$-$C_6$alkCOO$C_1$-$C_4$alkyl, —$C_1$-$C_6$alkCOO$C_1$-$C_3$alkyl, —$C_1$-$C_6$alkCOO$C_1$-$C_2$alkyl, or —$C_1$-$C_6$alkC methoxy, ethoxy, propoxy, isoproxy, butoxy, or t-butoxy alkyeleneOO$C_1$alkyl.

According to the disclosure, $R^3$ is H or $C_1$-$C_6$alkyl. In some aspects, $R^3$ is H. In other aspects, $R^3$ is $C_1$-$C_6$alkyl, for example, methyl, ethyl, propyl, isopropyl, butyl, s-butyl, t-butyl, pentyl, or hexyl.

According to the disclosure, Z is a bond or $C_1$-$C_6$alkylene optionally substituted with one, two, or three $R^4$ substituents independently selected from $C_1$-$C_6$alkyl. In preferred aspects, Z is a bond. In other aspects, Z is an unsubstituted $C_1$-$C_6$alkylene, for example, $C_1$-$C_5$alkylene, $C_1$-$C_4$alkylene, $C_1$-$C_3$alkylene, $C_1$-$C_2$alkylene, or $C_1$alkylene. In other aspects, Z is a $C_1$-$C_6$alkylene, for example, $C_1$-$C_5$alkylene, $C_1$-$C_4$alkylene, $C_1$-$C_3$alkylene, $C_1$-$C_2$alkylene, or $C_1$alkylene substituted with one, two, or three $R^4$ substituents, preferably one or two $R^4$ substituents, independently selected from $C_1$-$C_6$alkyl. In preferred aspects, Z is a $C_1$alkylene substituted with one $C_1$-$C_6$alkyl, preferably methyl.

According to some aspects of the disclosure, B is unsubstituted aryl, for example, unsubstituted phenyl or naphthyl. In other aspects, B is aryl substituted with 1, 2, or 3 substituents, preferably 1 or 2 substituents. The B substituents, which can be referred to as one or more R groups, are preferably independently selected from —OH, $C_1$-$C_6$alkyl, $C_1$-$C_6$haloalkyl, halo, —$OC_1$-$C_6$alkyl, —$OC_1$-$C_6$haloalkyl, —CN, aryl, or —Oaryl. Preferred substituted aryl moieties include phenyl and naphthyl, with phenyl being particularly preferred. In some aspects, the aryl is substituted with at least one substituent that is —OH. In some aspects, the aryl is substituted with at least one substituent that is $C_1$-$C_6$alkyl, for example, methyl, ethyl, propyl, isopropyl, butyl, s-butyl, t-butyl, pentyl, or hexyl. In other aspects, the aryl is substituted with at least one substituent that is $C_1$-$C_6$haloalkyl, for example, —$CF_3$. In other embodiments, the aryl is substituted with at least one substituent that is halo, for example, F, Cl, or Br, with F and Cl substituents being particularly preferred aryl substituents. In some aspects, the aryl is substituted with at least one substituent that is —$OC_1$-$C_6$alkyl, for example, methoxy, ethoxy, propoxy, isoproxy, butoxy, or t-butoxy. In yet other aspects, the aryl is substituted with at least one substituent that is —$OC_1$-$C_6$haloalkyl, for example, —$OCF_3$. In some embodiments, the aryl is substituted with at least one substituent that is —CN. In other aspects, the aryl is substituted with at least one substituent that is another aryl moiety, for example, a phenyl or naphthyl moiety. In some embodiments, the aryl is substituted with at least one substituent that is —Oaryl, for example, —Ophenyl.

According to some aspects of the disclosure, B is unsubstituted $C_3$-$C_{12}$cycloalkyl, for example, $C_3$cycloalkyl (e.g., cyclopropyl), $C_4$cycloalkyl (e.g., cyclobutyl), $C_5$cycloalkyl (e.g., cyclopentyl), $C_6$cycloalkyl (e.g., cyclohexyl), $C_7$cycloalkyl (e.g., bicyclo[2.2.1]heptanyl), $C_8$cycloalkyl (bicyclo[2.2.2]octanyl), $C_9$cycloalkyl, $C_{10}$cycloalkyl (e.g., adamantyl), $C_{11}$cycloalkyl, or $C_{12}$cycloalkyl. In some aspects, B is unsubstituted $C_3$-$C_6$cycloalkyl. In other aspects, B is unsubstituted $C_7$-$C_{12}$cycloalkyl or $C_7$-$C_{10}$cycloalkyl.

In other aspects, B is $C_3$-$C_{12}$cycloalkyl substituted with 1, 2, or 3 substituents, preferably 1 or 2 substituents. For example, in some aspects, B is substituted $C_3$cycloalkyl, $C_4$cycloalkyl, $C_5$cycloalkyl, $C_6$cycloalkyl, $C_7$cycloalkyl, $C_8$cycloalkyl, $C_9$cycloalkyl, $C_{10}$cycloalkyl, $C_{11}$cycloalkyl, or $C_{12}$cycloalkyl. In other aspects, B is substituted $C_3$-$C_6$cycloalkyl. In other aspects, B is substituted $C_7$-$C_{12}$cycloalkyl or $C_7$-$C_{10}$cycloalkyl. The B substituents, which can be referred to as one or more R groups, are preferably independently selected from —OH, $C_1$-$C_6$alkyl, $C_1$-$C_6$haloalkyl, halo, —$OC_1$-$C_6$alkyl, —$OC_1$-$C_6$haloalkyl, —CN, aryl, or —Oaryl. Preferred $C_3$-$C_{12}$cycloalkyl moieties include cyclopropyl, cyclobutyl, cyclopentyl, cyclohexyl, bicyclo[2.2.1]heptanyl, bicyclo[2.2.2]octanyl, and adamantyl. In some aspects, the $C_3$-$C_{12}$cycloalkyl is substituted with at least one substituent that is —OH. In some aspects, the $C_3$-$C_{12}$cycloalkyl is substituted with at least one substituent that is $C_1$-$C_6$alkyl, for example, methyl, ethyl, propyl, isopropyl, butyl, s-butyl, t-butyl, pentyl, or hexyl. In other aspects, the $C_3$-$C_{12}$cycloalkyl is substituted with at least one substituent that is $C_1$-$C_6$haloalkyl, for example, —$CF_3$. In other embodiments, the $C_3$-$C_{12}$cycloalkyl is substituted with at least one substituent that is halo, for example, F, Cl, or Br, with F and Cl substituents being particularly preferred $C_3$-$C_{12}$cycloalkyl substituents. In some aspects, the $C_3$-$C_{12}$cycloalkyl is substituted with at least one substituent that is —$OC_1$-$C_6$alkyl, for example, methoxy, ethoxy, propoxy, isoproxy, butoxy, or t-butoxy. In yet other aspects, the $C_3$-$C_{12}$cycloalkyl is substituted with at least one substituent that is —$OC_1$-$C_6$haloalkyl, for example, —$OCF_3$. In some embodiments, the $C_3$-$C_{12}$cycloalkyl is substituted with at least one substituent that is —CN. In other aspects, the $C_3$-$C_{12}$cycloalkyl is substituted with at least one substituent that is an aryl moiety, for example, a phenyl or naphthyl moiety. In some embodiments, the $C_3$-$C_{12}$cycloalkyl is substituted with at least one substituent that is —Oaryl, for example, —Ophenyl.

Pharmaceutically acceptable salts, stereoisomers, tautomers, and solvates of all embodiments of formulas I and II are also within the scope of the invention.

Preferred sub-formulas of formula I and formula II are those wherein Y is CH, W is CH, Z is a bond, and n is 2 include, for example,

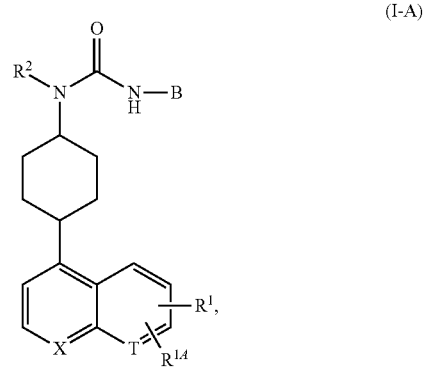

(I-A)

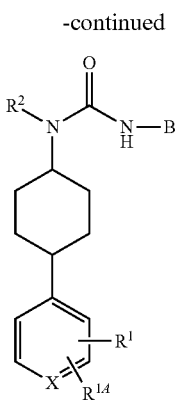

(II-A)

In some aspects, X in I-A and II-A is CH and T is CH. In some aspects, X is N and T is CH. In other aspects, X is CH and T is N. In other aspects, X is N and T is N. In other aspects, B in I-A and II-A is optionally substituted aryl. In yet other aspects, B in I-A and II-A is optionally substituted $C_3$-$C_{12}$cycloalkyl. In some aspects of formulas I-A and II-A, X is CH, B is optionally substituted aryl, $R^1$ is F or $CF_3$, $R^{1A}$ is H, $R^2$ is H, and $R^3$ is H. In some aspects of formulas I-A and II-A, X is N, B is optionally substituted aryl, $R^1$ is F or $CF_3$, $R^{1A}$ is H, $R^2$ is H, and $R^3$ is H. Pharmaceutically acceptable salts, stereoisomers, tautomers, and solvates of formulas I-A and II-A are within the scope of the invention.

Some preferred aspects of the disclosure include sub-formulas of formula I and formula II including I-B and II-B wherein Y is N, W is CH, Z is a bond, and n is 2 and include:

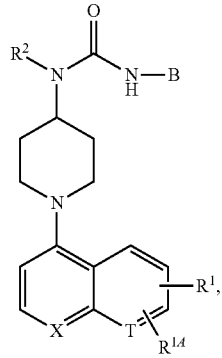

(I-B)

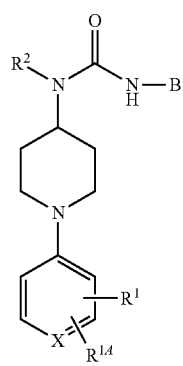

(II-B)

In some aspects, X in I-B and II-B is CH. In other aspects, X in I-B and II-B is N. In other aspects, X is CH and T is CH. In some aspects, X is N and T is CH. In other aspects, X is CH and T is N. In other aspects, X is N and T is N. In other aspects, B in I-B and II-B is optionally substituted aryl. In yet other aspects, B in I-B and II-B is optionally substituted $C_3$-$C_{12}$cycloalkyl. In some aspects of formulas I-B and II-B, X is CH, B is optionally substituted aryl, $R^1$ is F or $CF_3$, $R^{1A}$ is H, $R^2$ is H, and $R^3$ is H. In some aspects of formulas I-B and II-B, X is N, B is optionally substituted aryl, $R^1$ is F or $CF_3$, $R^{1A}$ is H, $R^2$ is H, and $R^3$ is H. Pharmaceutically acceptable salts, stereoisomers, tautomers, and solvates of formulas I-B and II-B are within the scope of the invention.

Some preferred aspects of the disclosure include sub-formulas of formula I and formula II including I-C and II-C wherein Y is CH, W is CH, Z is $C_1$alkylene, and n is 2 and include:

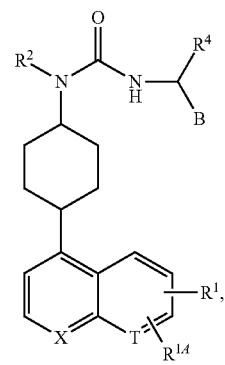

(I-C)

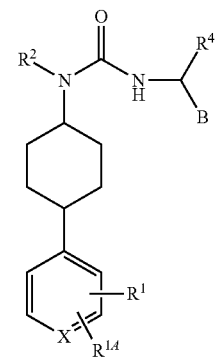

(II-C)

In some aspects, X in I-C and II-C is CH. In other aspects, X in I-C and II-C is N. In other aspects, X is CH and T is CH. In some aspects, X is N and T is CH. In other aspects, X is CH and T is N. In other aspects, X is N and T is N. In other aspects, B in I-C and II-C is optionally substituted aryl. In yet other aspects, B in I-C and II-C is optionally substituted $C_3$-$C_{12}$cycloalkyl. In some aspects of formulas I-C and II-C, X is CH, B is optionally substituted aryl, $R^1$ is F or $CF_3$, $R^{1A}$ is H, $R^2$ is H, and $R^3$ is H. In some aspects of formulas I-C and II-C, X is N, B is optionally substituted aryl, $R^1$ is F or $CF_3$, $R^{1A}$ is H, $R^2$ is H, and $R^3$ is H. Preferably, $R^4$ in compounds of formula I-C and II-C is methyl. Pharmaceutically acceptable salts, stereoisomers, tautomers, and solvates of formulas I-C and II-C are within the scope of the invention.

Some preferred aspects of the disclosure include sub-formulas of formula I and formula II including I-D and II-D wherein Y is N, W is CH, Z is $C_1$alkylene, and n is 2 and include:

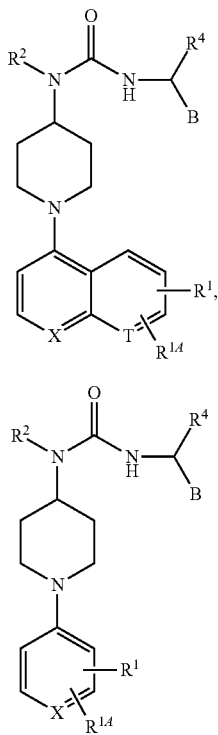

(I-D)

(II-D)

In some aspects, X in I-D and II-D is CH. In other aspects, X in I-D and II-D is N. In other aspects, X is CH and T is CH. In some aspects, X is N and T is CH. In other aspects, X is CH and T is N. In other aspects, X is N and T is N. In other aspects, B in I-D and II-D is optionally substituted aryl. In yet other aspects, B in I-D and II-D is optionally substituted $C_3$-$C_{12}$cycloalkyl. In some aspects of formulas I-D and II-D, X is CH, B is optionally substituted aryl, $R^1$ is F or $CF_3$, $R^{1A}$ is H, $R^2$ is H, and $R^3$ is H. In some aspects of formulas I-D and II-D, X is N, B is optionally substituted aryl, $R^1$ is F or $CF_3$, $R^{1A}$ is H, $R^2$ is H, and $R^3$ is H. Preferably, $R^4$ in compounds of formula I-D and II-D is methyl. Pharmaceutically acceptable salts, stereoisomers, tautomers, and solvates of formulas I-D and II-D are within the scope of the invention.

In another embodiment, the compounds of the invention have human IDO $IC_{50}$ values >50 nM. In another embodiment, the compounds of the invention have human IDO $IC_{50}$ values ≤50 nM. In another embodiment, the compounds of the invention have human IDO $IC_{50}$ values <5 nM.

OTHER EMBODIMENTS OF THE INVENTION

In another embodiment, the present invention provides a composition comprising one or more compounds of the present invention and/or a pharmaceutically acceptable salt thereof, a stereoisomer thereof, a tautomer thereof, or a solvate thereof.

In another embodiment, the present invention provides a pharmaceutical composition comprising a pharmaceutically acceptable carrier and at least one of the compounds of the present invention and/or a pharmaceutically acceptable salt thereof, a stereoisomer thereof, a tautomer thereof, or a solvate thereof.

In another embodiment, the present invention provides a pharmaceutical composition, comprising a pharmaceutically acceptable carrier and a therapeutically effective amount of at least one of the compounds of the present invention and/or a pharmaceutically acceptable salt thereof, a stereoisomer thereof, a tautomer thereof, or a solvate thereof.

In another embodiment, the present invention provides a process for making a compound of the present invention and/or a pharmaceutically acceptable salt thereof, a stereoisomer thereof, a tautomer thereof, or a solvate thereof.

In another embodiment, the present invention provides an intermediate for making a compound of the present invention and/or a pharmaceutically acceptable salt thereof, a stereoisomer thereof, a tautomer thereof, or a solvate thereof.

In another embodiment, the present invention provides a method for the treatment and/or prophylaxis of various types of cancer, viral infections and/or autoimmune diseases, comprising administering to a patient in need of such treatment and/or prophylaxis a therapeutically effective amount of one or more compounds of the present invention and/or a pharmaceutically acceptable salt thereof, a stereoisomer thereof or a tautomer thereof, alone, or, optionally, in combination with another compound of the present invention and/or at least one other type of therapeutic agent, such as a chemotherapeutic agent or a signal transductor inhibitor.

In another embodiment, the present invention provides a compound of the present invention, and/or a pharmaceutically acceptable salt thereof, a stereoisomer thereof or a tautomer thereof, for use in therapy.

In another embodiment, the present invention provides a combined preparation of a compound of the present invention, and/or a pharmaceutically acceptable salt thereof, a stereoisomer thereof or a tautomer thereof, and additional therapeutic agent(s) for simultaneous, separate or sequential use in therapy.

In another embodiment, the present invention provides a combined preparation of a compound of the present invention, and/or a pharmaceutically acceptable salt thereof, a stereoisomer thereof or a tautomer thereof, and additional therapeutic agent(s) for simultaneous, separate or sequential use in the treatment and/or prophylaxis of multiple diseases or disorders associated with the enzymatic activity of IDO.

In another aspect, the invention provides a method of treating a patient suffering from or susceptible to a medical condition that is sensitive to enzymatic activity of IDO. A number of medical conditions can be treated. The method comprises administering to the patient a therapeutically effective amount of a composition comprising a compound described herein and/or a pharmaceutically acceptable salt thereof, a stereoisomer thereof or a tautomer thereof. For example, the compounds described herein may be used to treat or prevent viral infections, proliferative diseases (e.g., cancer), and autoimmune diseases.

Therapeutic Applications

The compounds and pharmaceutical compositions of the present invention are useful in treating or preventing any disease or conditions that are sensitive to enzymatic activity of IDO. These include viral and other infections (e.g., skin infections, GI infection, urinary tract infections, genitourinary infections, systemic infections), proliferative diseases (e.g., cancer), and autoimmune diseases (e.g., rheumatoid arthritis, lupus). The compounds and pharmaceutical compositions may be administered to animals, preferably mammals (e.g., domesticated animals, cats, dogs, mice, rats), and more preferably humans. Any method of administration may be used to deliver the compound or pharmaceutical composition to the patient. In certain embodiments, the compound or pharmaceutical composition is administered orally. In other embodiments, the compound or pharmaceutical composition is administered parenterally.

Compounds of the invention can modulate activity of the enzyme indoleamine-2,3-dioxygenase (IDO). The term "modulate" is meant to refer to an ability to increase or decrease activity of an enzyme or receptor. Accordingly, compounds of the invention can be used in methods of modulating IDO by contacting the enzyme with any one or more of the compounds or compositions described herein. In some embodiments, compounds of the present invention can act as inhibitors of IDO. In further embodiments, the compounds of the invention can be used to modulate activity of IDO in cell or in an individual in need of modulation of the enzyme by administering a modulating (e.g., inhibiting) amount of a compound of the invention.

Compounds of the invention can inhibit activity of the enzyme indoleamine-2,3-dioxygenase (IDO). For example, the compounds of the invention can be used to inhibit activity of IDO in cell or in an individual in need of modulation of the enzyme by administering an inhibiting amount of a compound of the invention.

The present invention further provides methods of inhibiting the degradation of tryptophan in a system containing cells expressing IDO such as a tissue, living organism, or cell culture. In some embodiments, the present invention provides methods of altering (e.g., increasing) extracellular tryptophan levels in a mammal by administering an effective amount of a compound of composition provided herein. Methods of measuring tryptophan levels and tryptophan degradation are routine in the art.

The present invention further provides methods of inhibiting immunosuppression such as IDO-mediated immunosuppression in a patient by administering to the patient an effective amount of a compound or composition recited herein. IDO-mediated immunosuppression has been associated with, for example, cancers, tumor growth, metastasis, viral infection, and viral replication.

The present invention further provides methods of treating diseases associated with activity or expression, including abnormal activity and/or overexpression, of IDO in an individual (e.g., patient) by administering to the individual in need of such treatment a therapeutically effective amount or dose of a compound of the present invention or a pharmaceutical composition thereof. Example diseases can include any disease, disorder or condition that is directly or indirectly linked to expression or activity of the IDO enzyme, such as over expression or abnormal activity. An IDO-associated disease can also include any disease, disorder or condition that can be prevented, ameliorated, or cured by modulating enzyme activity. Examples of IDO-associated diseases include cancer, viral infection such as HIV infection, HCV infection, depression, neurodegenerative disorders such as Alzheimer's disease and Huntington's disease, trauma, age-related cataracts, organ transplantation (e.g., organ transplant rejection), and autoimmune diseases including asthma, rheumatoid arthritis, multiple sclerosis, allergic inflammation, inflammatory bowel disease, psoriasis and systemic lupus erythematosus.

As used herein, the term "cell" is meant to refer to a cell that is in vitro, ex vivo or in vivo. In some embodiments, an ex vivo cell can be part of a tissue sample excised from an organism such as a mammal. In some embodiments, an in vitro cell can be a cell in a cell culture. In some embodiments, an in vivo cell is a cell living in an organism such as a mammal.

As used herein, the term "contacting" refers to the bringing together of indicated moieties in an in vitro system or an in vivo system. For example, "contacting" the IDO enzyme with a compound of the invention includes the administration of a compound of the present invention to an individual or patient, such as a human, having IDO, as well as, for example, introducing a compound of the invention into a sample containing a cellular or purified preparation containing the IDO enzyme.

The term "IDO inhibitor" refers to an agent capable of inhibiting the activity of indoleamine 2,3-dioxygenase (IDO) and thereby reversing IDO-mediated immunosuppression. The IDO inhibitor may inhibit IDO1 and/or IDO2 (INDOL1). An IDO inhibitor may be a reversible or irreversible IDO inhibitor. "A reversible IDO inhibitor" is a compound that reversibly inhibits IDO enzyme activity either at the catalytic site or at a non-catalytic site and "an irreversible IDO inhibitor" is a compound that irreversibly destroys IDO enzyme activity.

Types of cancers that may be treated with the compounds of this invention include, but are not limited to, brain cancers, skin cancers, bladder cancers, ovarian cancers, breast cancers, gastric cancers, pancreatic cancers, prostate cancers, colon cancers, blood cancers, lung cancers and bone cancers. Examples of such cancer types include neuroblastoma, intestine carcinoma such as rectum carcinoma, colon carcinoma, familiar adenomatous polyposis carcinoma and hereditary non-polyposis colorectal cancer, esophageal carcinoma, labial carcinoma, larynx carcinoma, hypopharynx carcinoma, tongue carcinoma, salivary gland carcinoma, gastric carcinoma, adenocarcinoma, medullary thyroid carcinoma, papillary thyroid carcinoma, renal carcinoma, kidney parenchymal carcinoma, ovarian carcinoma, cervix carcinoma, uterine corpus carcinoma, endometrium carcinoma, chorion carcinoma, pancreatic carcinoma, prostate carcinoma, testis carcinoma, breast carcinoma, urinary carcinoma, melanoma, brain tumors such as glioblastoma, astrocytoma, meningioma, medulloblastoma and peripheral neuroectodermal tumors, Hodgkin lymphoma, non-Hodgkin lymphoma, Burkitt lymphoma, acute lymphatic leukemia (ALL), chronic lymphatic leukemia (CLL), acute myeloid leukemia (AML), chronic myeloid leukemia (CML), adult T-cell leukemia lymphoma, diffuse large B-cell lymphoma (DLBCL), hepatocellular carcinoma, gall bladder carcinoma, bronchial carcinoma, small cell lung carcinoma, non-small cell lung carcinoma, multiple myeloma, basalioma, teratoma, retinoblastoma, choroid melanoma, seminoma, rhabdomyosarcoma, craniopharyngioma, osteosarcoma, chondrosarcoma, myosarcoma, liposarcoma, fibrosarcoma, Ewing sarcoma and plasmacytoma.

Thus, according to another embodiment, the invention provides a method of treating an autoimmune disease by providing to a patient in need thereof a compound or composition of the present invention. Examples of such autoimmune diseases include, but are not limited to, collagen diseases such as rheumatoid arthritis, systemic lupus erythematosus, Sharp's syndrome, CREST syndrome (calcinosis, Raynaud's syndrome, esophageal dysmotility, telangiectasia), dermatomyositis, vasculitis (Morbus Wegener's) and Sjögren's syndrome, renal diseases such as Goodpasture's syndrome, rapidly-progressing glomerulonephritis and membranoproliferative glomerulonephritis type II, endocrine diseases such as type-I diabetes, autoimmune polyendocrinopathy-candidiasis-ectodermal dystrophy (APECED), autoimmune parathyroidism, pernicious anemia, gonad insufficiency, idiopathic Morbus Addison's, hyperthyreosis, Hashimoto's thyroiditis and primary myxedema, skin diseases such as pemphigus vulgaris, bullous pemphigoid, herpes gestationis, epidermolysis bullosa and erythema multiforme major, liver diseases such as primary biliary cirrhosis, autoimmune cholangitis, autoimmune hepatitis type-1, autoimmune hepatitis type-2, primary sclerosing cholangitis, neuronal diseases such as multiple sclerosis, myasthenia gravis, myasthenic Lambert-Eaton syndrome, acquired neuromyotomy, Guillain-Barré syndrome (Muller-Fischer syndrome), stiff-man syndrome, cerebellar degeneration, ataxia, opsoclonus, sensoric neuropathy and achalasia, blood diseases such as autoimmune hemolytic anemia, idiopathic thrombocytopenic purpura (Morbus Werlhof), infectious diseases with associated autoimmune reactions such as AIDS, malaria and Chagas disease.

One or more additional pharmaceutical agents or treatment methods such as, for example, anti-viral agents, chemotherapeutics or other anticancer agents, immune enhancers, immunosuppressants, radiation, anti-tumor and anti-viral vaccines, cytokine therapy (e.g., IL2 and GM-CSF), and/or tyrosine kinase inhibitors can be optionally used in combination with the compounds of the present invention for treatment of IDO-associated diseases, disorders or conditions. The agents can be combined with the present compounds in a single dosage form, or the agents can be administered simultaneously or sequentially as separate dosage forms.

Suitable chemotherapeutic or other anticancer agents include, for example, alkylating agents (including, without limitation, nitrogen mustards, ethylenimine derivatives, alkyl sulfonates, nitrosoureas and triazenes) such as uracil mustard, chlormethine, cyclophosphamide (CYTOXAN®), ifosfamide, melphalan, chlorambucil, pipobroman, triethylene-melamine, triethylenethiophosphoramine, busulfan, carmustine, lomustine, streptozocin, dacarbazine, and temozolomide.

In the treatment of melanoma, suitable agents for use in combination with the compounds of the present invention include: dacarbazine (DTIC), optionally, along with other chemotherapy drugs such as carmustine (BCNU) and cisplatin; the "Dartmouth regimen", which consists of DTIC, BCNU, cisplatin and tamoxifen; a combination of cisplatin, vinblastine, and DTIC, temozolomide or YERVOY®. Compounds according to the invention may also be combined with immunotherapy drugs, including cytokines such as interferon alpha, interleukin 2, and tumor necrosis factor (TNF) in the treatment of melanoma.

Compounds of the invention may also be used in combination with vaccine therapy in the treatment of melanoma. Anti-melanoma vaccines are, in some ways, similar to the anti-virus vaccines which are used to prevent diseases caused by viruses such as polio, measles, and mumps. Weakened melanoma cells or parts of melanoma cells called antigens may be injected into a patient to stimulate the body's immune system to destroy melanoma cells.

Melanomas that are confined to the arms or legs may also be treated with a combination of agents including one or more compounds of the invention, using a hyperthermic isolated limb perfusion technique. This treatment protocol temporarily separates the circulation of the involved limb from the rest of the body and injects high doses of chemotherapy into the artery feeding the limb, thus providing high doses to the area of the tumor without exposing internal organs to these doses that might otherwise cause severe side effects. Usually the fluid is warmed to 102° to 104° F.

Melphalan is the drug most often used in this chemotherapy procedure. This can be given with another agent called tumor necrosis factor (TNF).

Suitable chemotherapeutic or other anticancer agents include, for example, antimetabolites (including, without limitation, folic acid antagonists, pyrimidine analogs, purine analogs and adenosine deaminase inhibitors) such as methotrexate, 5-fluorouracil, floxuridine, cytarabine, 6-mercaptopurine, 6-thioguanine, fludarabine phosphate, pentostatine, and gemcitabine.

Suitable chemotherapeutic or other anticancer agents further include, for example, certain natural products and their derivatives (for example, vinca alkaloids, antitumor antibiotics, enzymes, lymphokines and epipodophyllotoxins) such as vinblastine, vincristine, vindesine, bleomycin, dactinomycin, daunorubicin, doxorubicin, epirubicin, idarubicin, ara-C, paclitaxel (Taxol), mithramycin, deoxycoformycin, mitomycin-C, L-asparaginase, interferons (especially IFN-a), etoposide, and teniposide.

Other cytotoxic agents include navelbene, CPT-11, anastrazole, letrazole, capecitabine, reloxafine, and droloxafine.

Also suitable are cytotoxic agents such as epidophyllotoxin; an antineoplastic enzyme; a topoisomerase inhibitor; procarbazine; mitoxantrone; platinum coordination complexes such as cisplatin and carboplatin; biological response modifiers; growth inhibitors; antihormonal therapeutic agents; leucovorin; tegafur; and haematopoietic growth factors.

Other anticancer agent(s) include antibody therapeutics such as trastuzumab (HERCEPTIN®), antibodies to costimulatory molecules such as CTLA-4, 4-1BB and PD-1, or antibodies to cytokines (IL-1O or TGF-β).

Other anticancer agents also include those that block immune cell migration such as antagonists to chemokine receptors, including CCR2 and CCR4.

Other anticancer agents also include those that augment the immune system such as adjuvants or adoptive T cell transfer.

Anticancer vaccines include dendritic cells, synthetic peptides, DNA vaccines and recombinant viruses.

The pharmaceutical composition of the invention may optionally include at least one signal transduction inhibitor (STI). A "signal transduction inhibitor" is an agent that selectively inhibits one or more vital steps in signaling pathways, in the normal function of cancer cells, thereby leading to apoptosis. Suitable STIs include, but are not limited to: (i) bcr/abl kinase inhibitors such as, for example, STI 571 (GLEEVEC®); (ii) epidermal growth factor (EGF) receptor inhibitors such as, for example, kinase inhibitors (IRESSA®, SSI-774) and antibodies (Imclone: C225 [Goldstein et al., *Clin. Cancer Res.*, 1:1311-1318 (1995)], and Abgenix: ABX-EGF); (iii) her-2/neu receptor inhibitors such as farnesyl transferase inhibitors (FTI) such as, for example, L-744,832 (Kohl et al., *Nat. Med.*, 1(8):792-797 (1995)); (iv) inhibitors of Akt family kinases or the Akt pathway, such as, for example, rapamycin (see, for example, Sekulic et al., *Cancer Res.*, 60:3504-3513 (2000)); (v) cell cycle kinase inhibitors such as, for example, flavopiridol and UCN-O1 (see, for example, Sausville, *Curr. Med. Chem. Anti-Canc. Agents*, 3:47-56 (2003)); and (vi) phosphatidyl inositol kinase inhibitors such as, for example, LY294002 (see, for example, Vlahos et al., *J. Biol. Chem.*, 269:5241-5248 (1994)). Alternatively, at least one STI and at least one IDO inhibitor may be in separate pharmaceutical compositions. In a specific embodiment of the present invention, at least one IDO inhibitor and at least one STI may be administered to the patient concurrently or sequentially. In other words, at least one IDO inhibitor may be administered first, at least one STI may be administered first, or at least one IDO inhibitor and at least one STI may be administered at the same time. Additionally, when more than one IDO inhibitor and/or STI is used, the compounds may be administered in any order.

The present invention further provides a pharmaceutical composition for the treatment of a chronic viral infection in a patient comprising at least one IDO inhibitor, optionally, at least one chemotherapeutic drug, and, optionally, at least one antiviral agent, in a pharmaceutically acceptable carrier. The pharmaceutical compositions may include at least one IDO inhibitor of the instant invention in addition to at least one established (known) IDO inhibitor. In a specific embodiment, at least one of the IDO inhibitors of the pharmaceutical composition is selected from the group consisting of compounds of formulas I and II.

Also provided is a method for treating a chronic viral infection in a patient by administering an effective amount of the above pharmaceutical composition.

In a specific embodiment of the present invention, at least one IDO inhibitor and at least one chemotherapeutic agent may be administered to the patient concurrently or sequentially. In other words, at least one IDO inhibitor may be administered first, at least one chemotherapeutic agent may be administered first, or at least one IDO inhibitor and the at least one STI may be administered at the same time. Additionally, when more than one IDO inhibitor and/or chemotherapeutic agent is used, the compounds may be administered in any order. Similarly, any antiviral agent or STI may also be administered at any point in comparison to the administration of an IDO inhibitor.

Chronic viral infections that may be treated using the present combinatorial treatment include, but are not limited to, diseases caused by: hepatitis C virus (HCV), human papilloma virus (HPV), cytomegalovirus (CMV), herpes simplex virus (HSV), Epstein-Barr virus (EBV), varicella zoster virus, Coxsackie virus, human immunodeficiency virus (HIV). Notably, parasitic infections (e.g., malaria) may also be treated by the above methods wherein compounds known to treat the parasitic conditions are optionally added in place of the antiviral agents.

In yet another embodiment, the pharmaceutical compositions comprising at least one IDO inhibitor of the instant invention may be administered to a patient to prevent arterial restenosis, such as after balloon endoscopy or stent placement. In a particular embodiment, the pharmaceutical composition further comprises at least one taxane (e.g., paclitaxel (Taxol); see, e.g., Scheller et al., *Circulation*, 110:810-814 (2004)).

Suitable antiviral agents contemplated for use in combination with the compounds of the present invention can comprise nucleoside and nucleotide reverse transcriptase inhibitors (NRTIs), non-nucleoside reverse transcriptase inhibitors (NNRTIs), protease inhibitors and other antiviral drugs.

Examples of suitable NRTIs include zidovudine (AZT); didanosine (ddI); zalcitabine (ddC); stavudine (d4T); lamivudine (3TC); abacavir (1592U89); adefovir dipivoxil [bis(POM)-PMEA]; lobucavir (BMS-180194); BCH-I0652; emtricitabine [(−)-FTC]; beta-L-FD4 (also called beta-L-D4C and named beta-L-2',3'-dicleoxy-5-fluoro-cytidene); DAPD, ((−)-beta-D-2,6-diamino-purine dioxolane); and lodenosine (FddA). Typical suitable NNRTIs include nevirapine (BI-RG-587); delaviradine (BHAP, U-90152); efavirenz (DMP-266); PNU-142721; AG-1549; MKC-442 (1-(ethoxy-methyl)-5-(1-methylethyl)-6-(phenylmethyl)-(2,4 (1H,3H)-pyrimidinedione); and (+)-calanolide A (NSC-675451) and B. Typical suitable protease inhibitors include saquinavir (Ro 31-8959); ritonavir (ABT-538); indinavir (MK-639); nelfinavir (AG-1343); amprenavir (141W94); lasinavir (BMS-234475); DMP-450; BMS-2322623; ABT-378; and AG-1549. Other antiviral agents include hydroxyurea, ribavirin, IL-2, IL-12, pentafuside and Yissum Project No. 11607.

Combination with an Immuno-Oncology Agent

Further provided herein are methods of treatment wherein a compound of formula I or formula II is administered with one or more immuno-oncology agents. The immuno-oncology agents used herein, also known as cancer immunotherapies, are effective to enhance, stimulate, and/or upregulate immune responses in a subject.

In one aspect, the Compound of formula I or formula II is sequentially administered prior to administration of the immuno-oncology agent. In another aspect, the Compound of formula I or formula II is administered concurrently with the immunology-oncology agent. In yet another aspect, the Compound of formula I or formula II is sequentially administered after administration of the immuno-oncology agent.

In another aspect, the Compound of formula I or formula II may be co-formulated with an immuno-oncology agent.

Immuno-oncology agents include, for example, a small molecule drug, antibody, or other biologic or small molecule. Examples of biologic immuno-oncology agents include, but are not limited to, cancer vaccines, antibodies, and cytokines. In one aspect, the antibody is a monoclonal antibody. In another aspect, the monoclonal antibody is humanized or human.

In one aspect, the immuno-oncology agent is (i) an agonist of a stimulatory (including a co-stimulatory) receptor or (ii) an antagonist of an inhibitory (including a co-inhibitory) signal on T cells, both of which result in amplifying antigen-specific T cell responses (often referred to as immune checkpoint regulators).

Certain of the stimulatory and inhibitory molecules are members of the immunoglobulin super family (IgSF). One important family of membrane-bound ligands that bind to co-stimulatory or co-inhibitory receptors is the B7 family, which includes B7-1, B7-2, B7-H1 (PD-L1), B7-DC (PD-L2), B7-H2 (ICOS-L), B7-H3, B7-H4, B7-H5 (VISTA), and B7-H6. Another family of membrane bound ligands that bind to co-stimulatory or co-inhibitory receptors is the TNF family of molecules that bind to cognate TNF receptor family members, which includes CD40 and CD40L, OX-40, OX-40L, CD70, CD27L, CD30, CD30L, 4-1BBL, CD137 (4-1BB), TRAIL/Apo2-L, TRAILR1/DR4, TRAILR2/DR5, TRAILR3, TRAILR4, OPG, RANK, RANKL, TWEAKR/Fn14, TWEAK, BAFFR, EDAR, XEDAR, TACI, APRIL, BCMA, LTβR, LIGHT, DcR3, HVEM, VEGI/TL1A, TRAMP/DR3, EDAR, EDA1, XEDAR, EDA2, TNFR1, Lymphotoxin α/TNFβ, TNFR2, TNFα, LTβR, Lymphotoxin α 1β2, FAS, FASL, RELT, DR6, TROY, NGFR.

In another aspect, the immuno-oncology agent is a cytokine that inhibits T cell activation (e.g., IL-6, IL-10, TGF-ß, VEGF, and other immunosuppressive cytokines) or a cytokine that stimulates T cell activation, for stimulating an immune response.

In one aspect, T cell responses can be stimulated by a combination of the Compound of Formula I or formula II and one or more of (i) an antagonist of a protein that inhibits T cell activation (e.g., immune checkpoint inhibitors) such as CTLA-4, PD-1, PD-L1, PD-L2, LAG-3, TIM-3, Galectin 9, CEACAM-1, BTLA, CD69, Galectin-1, TIGIT, CD113, GPR56, VISTA, 2B4, CD48, GARP, PD1H, LAIR1, TIM-1, and TIM-4, and (ii) an agonist of a protein that stimulates T cell activation such as B7-1, B7-2, CD28, 4-1BB (CD137), 4-1BBL, ICOS, ICOS-L, OX40, OX40L, GITR, GITRL, CD70, CD27, CD40, DR3 and CD28H.

Other agents that can be combined with the Compound of formula I or formula II for the treatment of cancer include antagonists of inhibitory receptors on NK cells or agonists of activating receptors on NK cells. For example, the Compound of formula I or formula II can be combined with antagonists of KIR, such as lirilumab.

Yet other agents for combination therapies include agents that inhibit or deplete macrophages or monocytes, including but not limited to CSF-1R antagonists such as CSF-1R antagonist antibodies including RG7155 (WO 11/70024, WO 11/107553, WO 11/131407, WO 13/87699, WO 13/119716, WO 13/132044) or FPA-008 (WO 11/140249, WO 13/169264, WO 14/036357).

In another aspect, the Compound of formula I or formula II can be used with one or more of agonistic agents that ligate positive costimulatory receptors, blocking agents that attenuate signaling through inhibitory receptors, antagonists, and one or more agents that increase systemically the frequency of anti-tumor T cells, agents that overcome distinct immune suppressive pathways within the tumor microenvironment (e.g., block inhibitory receptor engagement (e.g., PD-L1/PD-1 interactions), deplete or inhibit Tregs (e.g., using an anti-CD25 monoclonal antibody (e.g., daclizumab) or by ex vivo anti-CD25 bead depletion), inhibit metabolic enzymes such as IDO, or reverse/prevent T cell anergy or exhaustion) and agents that trigger innate immune activation and/or inflammation at tumor sites.

In one aspect, the immuno-oncology agent is a CTLA-4 antagonist, such as an antagonistic CTLA-4 antibody. Suitable CTLA-4 antibodies include, for example, YERVOY® (ipilimumab) or tremelimumab.

In another aspect, the immuno-oncology agent is a PD-1 antagonist, such as an antagonistic PD-1 antibody. Suitable PD-1 antibodies include, for example, OPDIVO® (nivolumab), KEYTRUDA® (pembrolizumab), or MEDI-0680 (AMP-514; WO 2012/145493). The immuno-oncology agent may also include pidilizumab (CT-011), though its specificity for PD-1 binding has been questioned. Another approach to target the PD-1 receptor is the recombinant protein composed of the extracellular domain of PD-L2 (B7-DC) fused to the Fc portion of IgG1, called AMP-224.

In another aspect, the immuno-oncology agent is a PD-L1 antagonist, such as an antagonistic PD-L1 antibody. Suitable PD-L1 antibodies include, for example, MPDL3280A (RG7446; WO 2010/077634), durvalumab (MEDI4736), BMS-936559 (WO 2007/005874), and MSB0010718C (WO 2013/79174).

In another aspect, the immuno-oncology agent is a LAG-3 antagonist, such as an antagonistic LAG-3 antibody. Suitable LAG3 antibodies include, for example, BMS-986016 (WO 10/19570, WO 14/08218), or IMP-731 or IMP-321 (WO 08/132601, WO 09/44273).

In another aspect, the immuno-oncology agent is a CD137 (4-1BB) agonist, such as an agonistic CD137 antibody. Suitable CD137 antibodies include, for example, urelumab and PF-05082566 (WO 12/32433).

In another aspect, the immuno-oncology agent is a GITR agonist, such as an agonistic GITR antibody. Suitable GITR antibodies include, for example, BMS-986153, BMS-986156, TRX-518 (WO 06/105021, WO 09/009116) and MK-4166 (WO 11/028683).

In another aspect, the immuno-oncology agent is an IDO antagonist. Suitable IDO antagonists include, for example, INCB-024360 (WO 2006/122150, WO 07/75598, WO 08/36653, WO 08/36642), indoximod, or NLG-919 (WO 09/73620, WO 09/1156652, WO 11/56652, WO 12/142237).

In another aspect, the immuno-oncology agent is an OX40 agonist, such as an agonistic OX40 antibody. Suitable OX40 antibodies include, for example, MEDI-6383 or MEDI-6469.

In another aspect, the immuno-oncology agent is an OX40L antagonist, such as an antagonistic OX40 antibody. Suitable OX40L antagonists include, for example, RG-7888 (WO 06/029879).

In another aspect, the immuno-oncology agent is a CD40 agonist, such as an agonistic CD40 antibody. In yet another embodiment, the immuno-oncology agent is a CD40 antagonist, such as an antagonistic CD40 antibody. Suitable CD40 antibodies include, for example, lucatumumab or dacetuzumab.

In another aspect, the immuno-oncology agent is a CD27 agonist, such as an agonistic CD27 antibody. Suitable CD27 antibodies include, for example, varlilumab.

In another aspect, the immuno-oncology agent is MGA271 (to B7H3) (WO 11/109400).

The present invention also includes pharmaceutical kits useful, for example, in the treatment or prevention of IDO-associated diseases or disorders, obesity, diabetes and other diseases referred to herein which include one or more containers containing a pharmaceutical composition comprising a therapeutically effective amount of a compound of the invention. Such kits can further include, if desired, one or more of various conventional pharmaceutical kit components, such as, for example, containers with one or more pharmaceutically acceptable carriers, additional containers, as will be readily apparent to those skilled in the art. Instructions, either as inserts or as labels, indicating quantities of the components to be administered, guidelines for administration, and/or guidelines for mixing the components, can also be included in the kit.

The combination therapy is intended to embrace administration of these therapeutic agents in a sequential manner, that is, wherein each therapeutic agent is administered at a different time, as well as administration of these therapeutic agents, or at least two of the therapeutic agents, in a substantially simultaneous manner. Substantially simultaneous administration can be accomplished, for example, by administering to the subject a single dosage form having a fixed ratio of each therapeutic agent or in multiple, single dosage forms for each of the therapeutic agents. Sequential or substantially simultaneous administration of each therapeutic agent can be effected by any appropriate route including, but not limited to, oral routes, intravenous routes, intramuscular routes, and direct absorption through mucous membrane tissues. The therapeutic agents can be administered by the same route or by different routes. For example, a first therapeutic agent of the combination selected may be administered by intravenous injection while the other therapeutic agents of the combination may be administered orally. Alternatively, for example, all therapeutic agents may be administered orally or all therapeutic agents may be administered by intravenous injection. Combination therapy also can embrace the administration of the therapeutic agents as described above in further combination with other biologically active ingredients and non-drug therapies (e.g., surgery or radiation treatment). Where the combination therapy further comprises a non-drug treatment, the non-drug treatment may be conducted at any suitable time so long as a beneficial effect from the co-action of the combination of the therapeutic agents and non-drug treatment is achieved. For example, in appropriate cases, the beneficial effect is still achieved when the non-drug treatment is temporally removed from the administration of the therapeutic agents, perhaps by days or even weeks.

Pharmaceutical Compositions and Dosing

The invention also provides pharmaceutically acceptable compositions which comprise a therapeutically effective amount of one or more of the compounds of formula I and/or Formula II, formulated together with one or more pharmaceutically acceptable carriers (additives) and/or diluents, and optionally, one or more additional therapeutic agents described above.

The compounds of this invention can be administered for any of the uses described herein by any suitable means, for example, orally, such as tablets, capsules (each of which includes sustained release or timed release formulations), pills, powders, granules, elixirs, tinctures, suspensions (including nanosuspensions, microsuspensions, spray-dried dispersions), syrups, and emulsions; sublingually; buccally; parenterally, such as by subcutaneous, intravenous, intramuscular, or intrastemal injection, or infusion techniques (e.g., as sterile injectable aqueous or non-aqueous solutions or suspensions); nasally, including administration to the nasal membranes, such as by inhalation spray; topically, such as in the form of a cream or ointment; or rectally such as in the form of suppositories. They can be administered alone, but generally will be administered with a pharmaceutical carrier selected on the basis of the chosen route of administration and standard pharmaceutical practice.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically acceptable carrier" as used herein means a pharmaceutically acceptable material, composition or vehicle, such as a liquid or solid filler, diluent, excipient, manufacturing aid (e.g., lubricant, talc magnesium, calcium or zinc stearate, or steric acid), or solvent encapsulating material, involved in carrying or transporting the subject compound from one organ, or portion of the body, to another organ, or portion of the body. Each carrier must be "acceptable" in the sense of being compatible with the other ingredients of the formulation and not injurious to the patient.

The term "pharmaceutical composition" means a composition comprising a compound of the invention in combination with at least one additional pharmaceutically acceptable carrier. A "pharmaceutically acceptable carrier" refers to media generally accepted in the art for the delivery of biologically active agents to animals, in particular, mammals, including, i.e., adjuvant, excipient or vehicle, such as diluents, preserving agents, fillers, flow regulating agents, disintegrating agents, wetting agents, emulsifying agents, suspending agents, sweetening agents, flavoring agents, perfuming agents, antibacterial agents, antifungal agents, lubricating agents and dispensing agents, depending on the nature of the mode of administration and dosage forms.

Pharmaceutically acceptable carriers are formulated according to a number of factors well within the purview of those of ordinary skill in the art. These include, without limitation: the type and nature of the active agent being formulated; the subject to which the agent-containing composition is to be administered; the intended route of administration of the composition; and the therapeutic indication being targeted. Pharmaceutically acceptable carriers include both aqueous and non-aqueous liquid media, as well as a variety of solid and semi-solid dosage forms. Such carriers can include a number of different ingredients and additives in addition to the active agent, such additional ingredients being included in the formulation for a variety of reasons, e.g., stabilization of the active agent, binders, etc., well known to those of ordinary skill in the art. Descriptions of suitable pharmaceutically acceptable carriers, and factors involved in their selection, are found in a variety of readily available sources such as, for example, Allen, Jr., L. V. et al., *Remington: The Science and Practice of Pharmacy* (2 Volumes), 22nd Edition, Pharmaceutical Press (2012).

The dosage regimen for the compounds of the present invention will, of course, vary depending upon known factors, such as the pharmacodynamic characteristics of the particular agent and its mode and route of administration; the species, age, sex, health, medical condition, and weight of the recipient; the nature and extent of the symptoms; the kind of concurrent treatment; the frequency of treatment; the route of administration, the renal and hepatic function of the patient, and the effect desired.

By way of general guidance, the daily oral dosage of each active ingredient, when used for the indicated effects, will range between about 0.001 to about 5000 mg per day, preferably between about 0.01 to about 1000 mg per day, and most preferably between about 0.1 to about 250 mg per day. Intravenously, the most preferred doses will range from about 0.01 to about 10 mg/kg/minute during a constant rate infusion. Compounds of this invention may be administered in a single daily dose, or the total daily dosage may be administered in divided doses of two, three, or four times daily.

The compounds are typically administered in admixture with suitable pharmaceutical diluents, excipients, or carriers (collectively referred to herein as pharmaceutical carriers) suitably selected with respect to the intended form of administration, e.g., oral tablets, capsules, elixirs, and syrups, and consistent with conventional pharmaceutical practices.

Dosage forms (pharmaceutical compositions) suitable for administration may contain from about 1 milligram to about 2000 milligrams of active ingredient per dosage unit. In these pharmaceutical compositions the active ingredient will ordinarily be present in an amount of about 0.1-95% by weight based on the total weight of the composition.

A typical capsule for oral administration contains at least one of the compounds of the present invention (250 mg), lactose (75 mg), and magnesium stearate (15 mg). The mixture is passed through a 60 mesh sieve and packed into a No. 1 gelatin capsule.

A typical injectable preparation is produced by aseptically placing at least one of the compounds of the present invention (250 mg) into a vial, aseptically freeze-drying and sealing. For use, the contents of the vial are mixed with 2 mL of physiological saline, to produce an injectable preparation.

The present invention includes within its scope pharmaceutical compositions comprising, as an active ingredient, a therapeutically effective amount of at least one of the compounds of the present invention, alone or in combination with a pharmaceutical carrier. Optionally, compounds of the present invention can be used alone, in combination with other compounds of the invention, or in combination with one or more other therapeutic agent(s), e.g., an anticancer agent or other pharmaceutically active material.

Regardless of the route of administration selected, the compounds of the present invention, which may be used in a suitable hydrated form, and/or the pharmaceutical compositions of the present invention, are formulated into pharmaceutically acceptable dosage forms by conventional methods known to those of skill in the art.

Actual dosage levels of the active ingredients in the pharmaceutical compositions of this invention may be varied so as to obtain an amount of the active ingredient which is effective to achieve the desired therapeutic response for a particular patient, composition, and mode of administration, without being toxic to the patient.

The selected dosage level will depend upon a variety of factors including the activity of the particular compound of the present invention employed, or the ester, salt or amide thereof, the route of administration, the time of administration, the rate of excretion or metabolism of the particular compound being employed, the rate and extent of absorption, the duration of the treatment, other drugs, compounds and/or materials used in combination with the particular compound employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved.

In general, a suitable daily dose of a compound of the invention will be that amount of the compound which is the lowest dose effective to produce a therapeutic effect. Such an effective dose will generally depend upon the factors described above.

If desired, the effective daily dose of the active compound may be administered as two, three, four, five, six or more sub-doses administered separately at appropriate intervals throughout the day, optionally, in unit dosage forms. In certain aspects of the invention, dosing is one administration per day.

While it is possible for a compound of the present invention to be administered alone, it is preferable to administer the compound as a pharmaceutical formulation (composition).

Definitions

Unless specifically stated otherwise herein, references made in the singular may also include the plural. For example, "a" and "an" may refer to either one, or one or more.

Unless otherwise indicated, any heteroatom with unsatisfied valences is assumed to have hydrogen atoms sufficient to satisfy the valences.

Throughout the specification and the appended claims, a given chemical formula or name shall encompass all stereo and optical isomers and racemates thereof where such isomers exist. Unless otherwise indicated, all chiral (enantiomeric and diastereomeric) and racemic forms are within the scope of the invention. Many geometric isomers of C=C double bonds, C=N double bonds, ring systems, and the like can also be present in the compounds, and all such stable isomers are contemplated in the present invention. Cis- and trans- (or E- and Z-) geometric isomers of the compounds of the present invention are described and may be isolated as a mixture of isomers or as separated isomeric forms. The present compounds can be isolated in optically active or racemic forms. Optically active forms may be prepared by resolution of racemic forms or by synthesis from optically active starting materials. All processes used to prepare compounds of the present invention and intermediates made therein are considered to be part of the present invention. When enantiomeric or diastereomeric products are prepared, they may be separated by conventional methods, for example, by chromatography or fractional crystallization. Depending on the process conditions the end products of the present invention are obtained either in free (neutral) or salt form. Both the free form and the salts of these end products are within the scope of the invention. If so desired, one form of a compound may be converted into another form. A free base or acid may be converted into a salt; a salt may be converted into the free compound or another salt; a mixture of isomeric compounds of the present invention may be separated into the individual isomers. Compounds of the present invention, free form and salts thereof, may exist in multiple tautomeric forms, in which hydrogen atoms are transposed to other parts of the molecules and the chemical bonds between the atoms of the molecules are consequently rearranged. It should be understood that all tautomeric forms, insofar as they may exist, are included within the invention.

For purposes of clarity and in accordance with standard convention in the art, the symbol

is used in formulas and tables to show the bond that is the point of attachment of the moiety or substituent to the core/nucleus of the structure.

Additionally, for purposes of clarity, where a substituent has a dash (—) that is not between two letters or symbols; this is used to indicate a point of attachment for a substituent. For example, —CONH$_2$ is attached through the carbon atom.

Additionally, for purposes of clarity, when there is no substituent shown at the end of a solid line, this indicates that there is a methyl (CH$_3$) group connected to the bond.

As used herein, the terms "alkyl" and "alkylene" (also referred to as "alk") are intended to include both branched and straight-chain saturated aliphatic hydrocarbon groups having the specified number of carbon atoms. For example, "C$_1$-C$_6$ alkyl" or "C$_{1-6}$ alkyl" denotes alkyl having 1 to 6 carbon atoms. Example alkyl groups include, but are not limited to, methyl (Me), ethyl (Et), propyl (e.g., n-propyl and isopropyl), butyl (e.g., n-butyl, isobutyl, t-butyl), and pentyl (e.g., n-pentyl, isopentyl, neopentyl). "C$_1$-C$_6$alkylene" denotes alkylene having 1 to 6 carbon atoms. Example alkylene groups include, but are not limited to, methylene (—CH$_2$—), ethylene (—CH$_2$CH$_2$—), and the like.

As used herein, "aryl" refers to an aromatic ring system which includes, but not limited to phenyl, biphenyl, indanyl, 1-naphthyl, 2-naphthyl and terahydronaphthyl.

"Halo" or "halogen" includes fluoro, chloro, bromo, and iodo.

"Haloalkyl" is intended to include both branched and straight-chain saturated aliphatic hydrocarbon groups having the specified number of carbon atoms, substituted with 1 or more halogens. Examples of haloalkyl include, but are not limited to, fluoromethyl, difluoromethyl, trifluoromethyl, trichloromethyl, pentafluoroethyl, pentachloroethyl, 2,2,2-trifluoroethyl, heptafluoropropyl, and heptachloropropyl. Examples of haloalkyl also include "fluoroalkyl" that is intended to include both branched and straight-chain saturated aliphatic hydrocarbon groups having the specified number of carbon atoms, substituted with 1 or more fluorine atoms.

The term "cycloalkyl" refers to hydrocarbon rings having the indicated number of ring atoms, e.g., $C_3$-$C_6$cycloalkyl or $C_3$-$C_{12}$cycloalkyl, and being fully saturated. "Cycloalkyl" is also meant to refer to bicyclic and polycylic hydrocarbon rings such as, for example, bicyclo[2.2.1]heptane, bicyclo [2.2.2] octane, and adamantyl. $C_{3-6}$ cycloalkyl is intended to include $C_3$, $C_4$, $C_5$, and $C_6$ cycloalkyl groups. Example cycloalkyl groups include, but are not limited to, cyclopropyl, cyclobutyl, cyclopentyl, cyclohexyl, and norbornyl.

As referred to herein, the term "substituted" means that at least one hydrogen atom is replaced with a non-hydrogen group, provided that normal valencies are maintained and that the substitution results in a stable compound.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic groups such as amines; and alkali or organic salts of acidic groups such as carboxylic acids. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, and nitric; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, and isethionic, and the like.

The pharmaceutically acceptable salts of the present invention can be synthesized from the parent compound that contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in Allen, Jr., L. V., ed., *Remington: The Science and Practice of Pharmacy,* 22nd Edition, Pharmaceutical Press, London, UK (2012). The disclosure of which is hereby incorporated by reference.

In addition, compounds of formula I and formula II may have prodrug forms.

Any compound that will be converted in vivo to provide the bioactive agent (i.e., a compound of formula I or II) is a prodrug within the scope and spirit of the invention. Various forms of prodrugs are well known in the art. For examples of such prodrug derivatives, see:

a) Bundgaard, H., ed., *Design of Prodrugs*, Elsevier (1985), and Widder, K. et al., eds., *Methods in Enzymology*, 112:309-396, Academic Press (1985);

b) Bundgaard, H., Chapter 5: "Design and Application of Prodrugs", *A Textbook of Drug Design and Development*, pp. 113-191, Krogsgaard-Larsen, P. et al., eds., Harwood Academic Publishers (1991);

c) Bundgaard, H., *Adv. Drug Deliv. Rev.,* 8:1-38 (1992);

d) Nielsen, N. M. et al., *J. Pharm. Sci.,* 77:285 (1988);

e) Kakeya, N. et al., *Chem. Pharm. Bull.,* 32:692 (1984); and g) Rautio, J., ed., *Prodrugs and Targeted Delivery* (*Methods and Principles in Medicinal Chemistry*), Vol. 47, Wiley-VCH (2011).

Compounds containing a carboxy group can form physiologically hydrolyzable esters that serve as prodrugs by being hydrolyzed in the body to yield formula I or formula II compounds per se. Such prodrugs are preferably administered orally since hydrolysis in many instances occurs principally under the influence of the digestive enzymes. Parenteral administration may be used where the ester per se is active, or in those instances where hydrolysis occurs in the blood. Examples of physiologically hydrolyzable esters of compounds of formula I or formula II include $C_{1-6}$alkyl, $C_{1-6}$alkylbenzyl, 4-methoxybenzyl, indanyl, phthalyl, methoxymethyl, $C_{1-6}$ alkanoyloxy-$C_{1-6}$alkyl (e.g., acetoxymethyl, pivaloyloxymethyl or propionyloxymethyl), $C_{1-6}$alkoxycarbonyloxy-$C_{1-6}$alkyl (e.g., methoxycarbonyloxymethyl or ethoxycarbonyloxymethyl, glycyloxymethyl, phenylglycyloxymethyl, (5-methyl-2-oxo-1,3-dioxolen-4-yl)-methyl), and other well-known physiologically hydrolyzable esters used, for example, in the penicillin and cephalosporin arts. Such esters may be prepared by conventional techniques known in the art.

Preparation of prodrugs is well known in the art and described in, for example, King, F. D., ed., *Medicinal Chemistry: Principles and Practice*, The Royal Society of Chemistry, Cambridge, UK (Second Edition, reproduced, 2006); Testa, B. et al., *Hydrolysis in Drug and Prodrug Metabolism. Chemistry, Biochemistry and Enzymology*, VCHA and Wiley-VCH, Zurich, Switzerland (2003); Wermuth, C. G., ed., *The Practice of Medicinal Chemistry*, Third Edition, Academic Press, San Diego, Calif. (2008).

The present invention is intended to include all isotopes of atoms occurring in the present compounds. Isotopes include those atoms having the same atomic number but different mass numbers. By way of general example and without limitation, isotopes of hydrogen include deuterium and tritium. Isotopes of carbon include $^{13}C$ and $^{14}C$. Isotopically-labeled compounds of the invention can generally be prepared by conventional techniques known to those skilled in the art or by processes analogous to those described herein, using an appropriate isotopically-labeled reagent in place of the non-labeled reagent otherwise employed.

The term "solvate" means a physical association of a compound of this invention with one or more solvent molecules, whether organic or inorganic. This physical association includes hydrogen bonding. In certain instances the solvate will be capable of isolation, for example, when one or more solvent molecules are incorporated in the crystal lattice of the crystalline solid. The solvent molecules in the solvate may be present in a regular arrangement and/or a non-ordered arrangement. The solvate may comprise either a stoichiometric or nonstoichiometric amount of the solvent molecules. "Solvate" encompasses both solution-phase and isolable solvates. Exemplary solvates include, but are not limited to, hydrates, ethanolates, methanolates, and isopropanolates. Methods of solvation are generally known in the art.

As used herein, the term "patient" refers to organisms to be treated by the methods of the present invention. Such organisms preferably include, but are not limited to, mammals (e.g., murines, simians, equines, bovines, porcines, canines, felines, and the like), and most preferably refers to humans.

As used herein, the term "effective amount" means that amount of a drug or pharmaceutical agent, i.e., a compound of the invention, that will elicit the biological or medical response of a tissue, system, animal or human that is being sought, for instance, by a researcher or clinician. Furthermore, the term "therapeutically effective amount" means any amount which, as compared to a corresponding subject who has not received such amount, results in improved treatment, healing, prevention, or amelioration of a disease, disorder, or side effect, or a decrease in the rate of advancement of a disease or disorder. An effective amount can be administered in one or more administrations, applications or dosages and is not intended to be limited to a particular formulation or administration route. The term also includes within its scope amounts effective to enhance normal physiological function As used herein, the term "treating" includes any effect, e.g., lessening, reducing, modulating, ameliorating or eliminating, that results in the improvement of the condition, disease, disorder, and the like, or ameliorating a symptom thereof.

As used herein, the term "pharmaceutical composition" refers to the combination of an active agent with a carrier, inert or active, making the composition especially suitable for diagnostic or therapeutic use in vivo or ex vivo.

For therapeutic use, salts of the compounds of the present invention are contemplated as being pharmaceutically acceptable. However, salts of acids and bases that are non-pharmaceutically acceptable may also find use, for example, in the preparation or purification of a pharmaceutically acceptable compound.

Methods of Preparation

The compounds of the present invention may be prepared from starting materials which are known in the chemical literature or are commercially available by methods such as those illustrated in the following Schemes utilizing chemical transformations known to those skilled in the art of organic chemistry. Solvents, temperatures, pressures, and other reaction conditions may readily be selected by one of ordinary skill in the art. These Schemes are illustrative and are not meant to limit the possible techniques one skilled in the art may use to manufacture compounds disclosed herein. Different methods may be evident to those skilled in the art. Additionally, the various steps in the synthesis may be performed in an alternate sequence or order to give the desired compound(s). Further, the representation of the reactions in these Schemes as discrete steps does not preclude their being performed in tandem, either by telescoping multiple steps in the same reaction vessel or by performing multiple steps without purifying or characterizing the intermediate(s). In addition, many of the compounds prepared by the methods below can be further modified using conventional chemistry well known to those skilled in the art. All documents cited herein are incorporated herein by reference in their entirety.

Reference can also be made to International Application Nos. PCT/US2015/059271, PCT/US2015/059311, and PCT/US2015/059316.

References to many of these chemical transformations employed herein can be found in Smith, M. B. et al., March's Advanced Organic Chemistry Reactions, Mechanisms, and Structure, Fifth Edition, Wiley-Interscience, New York (2001), or other standard texts on the topic of synthetic organic chemistry. Certain transformations may require that reactive functional groups be masked by protecting group(s). A convenient reference which provides conditions for introduction, removal, and relative susceptibility to reaction conditions of these groups is Greene, T. W. et al., Protective Groups in Organic Synthesis, Third Edition, Wiley-Interscience, New York (1999).

Schemes 1-2 depict methods for preparing compounds of formula I. These methods can also be applied to preparation of compounds of the disclosure.

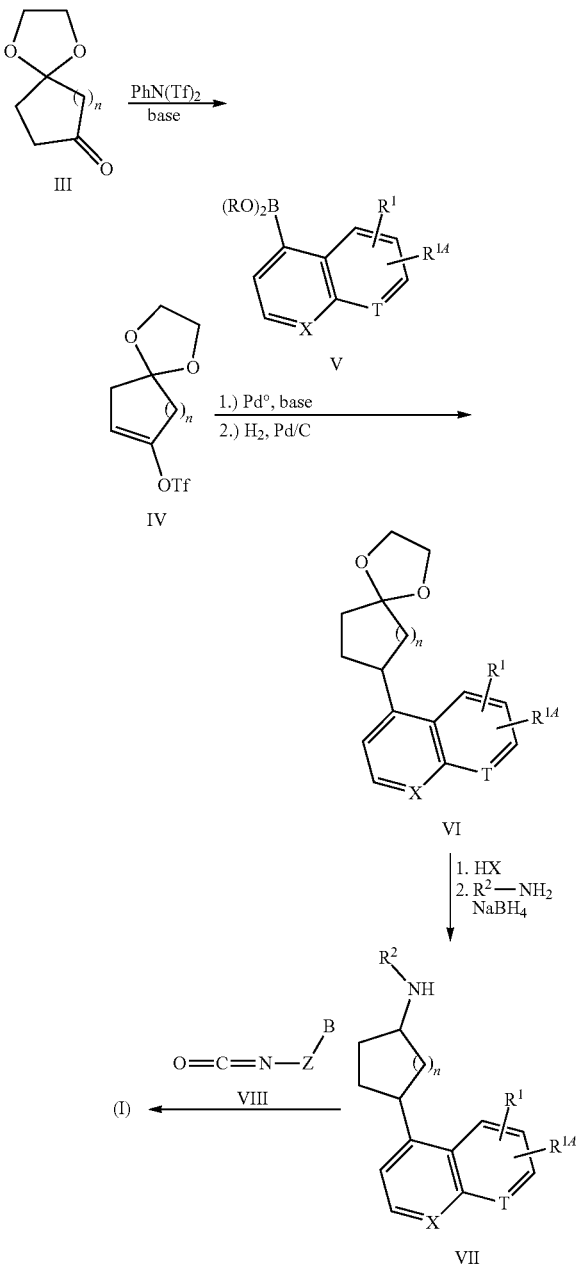

Ketones III can be deprotonated with bases such as LiHMDS and react with N-phenyltrifluoromethanesulfonimide or similar reagents to afford triflates of the general structure IV. These triflates participate in Suzuki couplings (T. Ishiyama, M. Murata, N. Miyaura, *J. Org. Chem.*, 1995, 60, 7508-7510) with boronic acids or esters Ar—B(OR)$_2$ such as V to afford coupled products. Many variations on this reaction are known, but generally it involves heating the two substrates and a catalyst such as (Ph$_3$P)$_4$Pd in a solvent such as DMF with a base such as aq. potassium carbonate. Reduction of the olefin provides intermediate VI. Hydrolysis of the ketal group affords the corresponding ketone. Typically, this is accomplished by heating with an aqueous acid such as HCl in the presence of a co-solvent such as THF. In addition to the cyclic ethylene glycol-based ketal shown, other cyclic and acyclic ketal protecting groups could be used. The resulting ketone can be treated with an amine R$^2$—NH$_2$ to generate an intermediate imine that can be reduced by NaBH$_4$ or similar hydride reducing agents to afford secondary amines of the general structure VII. These amines can be treated with an isocyanate of general structure VIII to give compounds of formula I.

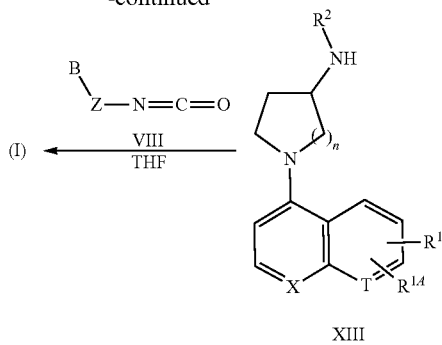

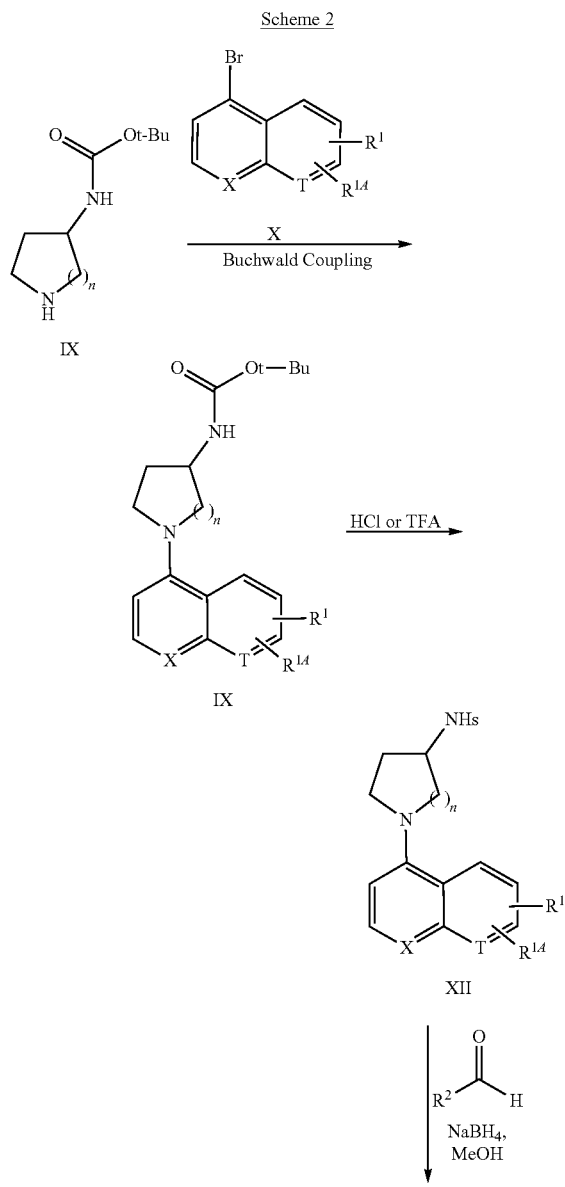

Tertiary butyl carbamates of amino piperidines and pyrrolidines of general structure IX are known compounds and can undergo S$_N$Ar reactions with halogenated heteroaromatics of general structure X to afford intermediates XI. Treatment of the benzyl carbamate XI under strongly acidic conditions, such as TFA or HCl, will afford amines of general structure XII. Treatment of amines XII with an aldehyde and a reducing agent, such as sodium borohydride, can afford the substituted amine of general structure XIII. Amines XIII can then be treated with isocyanates of general structure VIII to give compounds of formula I.

EXAMPLES

The following Examples are put forth so as to provide those of ordinary skill in the art with a complete disclosure and description of how to make and use the present invention, and are not intended to limit the scope of what the inventors regard as their invention, nor are they intended to represent that the experiments below were performed or that they are all of the experiments that may be performed. It is to be understood that exemplary descriptions written in the present tense were not necessarily performed, but rather that the descriptions can be performed to generate data and the like of a nature described therein. Efforts have been made to ensure accuracy with respect to numbers used (e.g., amounts, temperature, etc.), but some experimental errors and deviations should be accounted for.

Unless indicated otherwise, parts are parts by weight, molecular weight is weight average molecular weight, temperature is in degrees Celsius (° C.), and pressure is at or near atmospheric. Standard abbreviations are used, including the following: wt=wildtype; bp=base pair(s); kb=kilobase(s); nt=nucleotides(s); aa=amino acid(s); s or sec=second(s); min=minute(s); h or hr=hour(s); ng=nanogram; g=microgram; mg=milligram; g=gram; kg=kilogram; dl or dL=deciliter; μl or μL=microliter; ml or mL=milliliter; l or L=liter; M=micromolar; mM=millimolar; M=molar; kDa=kilodalton; i.m.=intramuscular(ly); i.p.=intraperitoneal(ly); SC or SQ=subcutaneous(ly); QD=daily; BID=twice daily; QW=weekly; QM=monthly; HPLC=high performance liquid chromatography; BW=body weight; U=unit; ns=not statistically significant; PBS=phosphate-buffered saline; IHC=immunohistochemistry; DMEM=Dulbecco's Modification of Eagle's Medium; EDTA=ethylenediaminetetraacetic acid.

Method A:

Waters Acquity SDS using the following method: Linear Gradient of 2% to 98% solvent B over 1.7 min; UV visualization at 220 nm; Column: BEH C18 2.1 mm×50 mm; 1.7 μm particle (Heated to Temp. 50° C.); Flow rate: 0.8 ml/min; Mobile phase A: 100% Water, 0.05% TFA; Mobile phase B: 100% Acetonitrile, 0.05% TFA.

Method B:

Waters Acquity SDS using the following method: Linear Gradient of 2% to 98% solvent B over 1.7 min; UV visualization at 220 nm; Column: BEH C18 2.1 mm×50 mm; 1.7 um particle (Heated to Temp. 50° C.); Flow rate: 0.8 ml/min; Mobile phase A: 100% Water, 0.05% TFA; Mobile phase B: 100% Acetonitrile, 0.05% TFA.

Method I:

Column: Waters Acquity UPLC BEH C18, 2.1×50 mm, 1.7-μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0-100% B over 3 minutes, then a 0.75-minute hold at 100% B; Flow: 1.0 mL/min; Detection: UV at 220 nm.

Example 1

3-(4-Chlorophenyl)-1-(1-(6-fluoroquinolin-4-yl)piperidin-4-yl)-1-methylurea

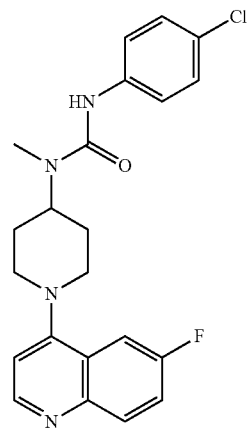 [SMILES: CN(C(=O)Nc1ccc(Cl)cc1)C1CCN(c2ccnc3ccc(F)cc23)CC1]

1A. tert-Butyl (1-(6-fluoroquinolin-4-yl)piperidin-4-yl)(methyl)carbamate

To a homogeneous mixture of 4-chloro-6-fluoroquinoline (200.0 mg, 1.1 mmol) in anhydrous NMP (5 mL), in a sealable vial, was added 4-Boc-4-N-methyl-aminopiperidine (330.0 mg, 1.5 mmol) followed by DIPEA (0.8 mL, 4.6 mmol). The vial was sealed and the mixture was stirred at 120° C. for 15 hours. After cooling to room temperature, the reaction mixture was partitioned between EtOAc and water. The layers were separated and the aqueous layer was extracted twice more with EtOAc. The organic extracts were combined, washed with brine, dried ($Na_2SO_4$), filtered and concentrated in vacuo to afford the crude product which was used without further purification, based on quantitative yield. MS(ES): m/z=360 $[M+H]^+$. $t_R$=0.75 min (Method A).

1B. 1-(6-Fluoroquinolin-4-yl)-N-methylpiperidin-4-amine

To a homogeneous mixture of tert-butyl (1-(6-fluoroquinolin-4-yl)piperidin-4-yl)(methyl)carbamate (396.0 mg, 1.1 mmol) in dioxane (2 mL), under nitrogen atmosphere, was added 4M HCl in dioxane (2 mL, 8.0 mmol). The resultant mixture was stirred at ambient temperature for 6 hours, during which time a precipitate formed. Vacuum filtration afforded the HCl salt of the title compound as a pale yellow solid (347.2 mg, 95% yield) which was used without further purification. MS(ES): m/z=260 $[M+H]^+$. $t_R$=0.43 min (Method A).

Example 1. 3-(4-Chlorophenyl)-1-(1-(6-fluoroquinolin-4-yl)piperidin-4-yl)-1-methylurea To a heterogeneous mixture of the HCl salt of 1-(6-fluoroquinolin-4-yl)-N-methylpiperidin-4-amine (94B, 30.0 mg, 0.09 mmol) in anhydrous THF (1 mL), at room temperature, was added DIPEA (0.05 mL, 0.29 mmol) followed by 1-chloro-4-isocyanatobenzene (16.6 mg, 0.11 mmol). The resulting mixture was stirred for 88 hours, before being diluted with DMSO, filtered through a syringe filter, then purified via preparative HPLC/MS to afford the title compound (19.3 mg; 52% yield). MS(ES): m/z=413 $[M+H]^+$. $t_R$=1.43 min (Method I). $^1$H NMR (500 MHz, DMSO-$d_6$) δ 8.67 (d, J=4.3 Hz, 1H), 8.44 (s, 1H), 8.07-7.98 (m, 1H), 7.75-7.57 (m, 2H), 7.52 (d, J=8.0 Hz, 2H), 7.28 (d, J=8.2 Hz, 2H), 7.06 (d, J=4.5 Hz, 1H), 4.39-4.22 (m, 1H), 3.58-3.38 (m, 2H), 2.98-2.84 (m, 5H), 2.18-2.02 (m, 2H), 1.73 (d, J=11.4 Hz, 2H).

Example 2

3-(4-Butylphenyl)-1-(1-(6-fluoroquinolin-4-yl)piperidin-4-yl)-1-methylurea

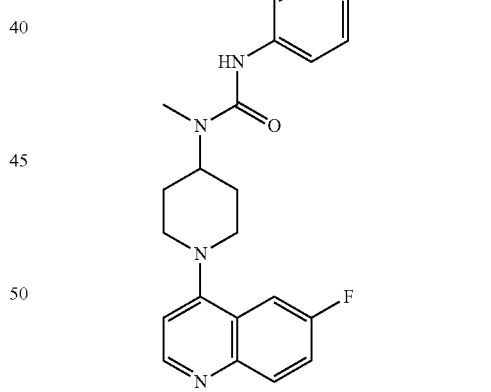

Example 2 (33.1 mg; 84% yield) was prepared following a procedure analogous to that for the synthesis of Example 1, except that 4-N-butylphenyl isocyanate (0.019 mL, 0.11 mmol) was used instead of 1-chloro-4-isocyanatobenzene. MS(ES): m/z=435 $[M+H]^+$. $T_r$=1.78 min (Method I). $^1$H NMR (500 MHz, DMSO-$d_6$) δ 8.62 (d, J=6.5 Hz, 1H), 8.23 (s, 1H), 8.04 (dd, J=8.6, 5.0 Hz, 1H), 7.94-7.85 (m, 2H), 7.31 (d, J=7.9 Hz, 2H), 7.22 (d, J=6.6 Hz, 1H), 7.04 (d, J=8.1 Hz, 2H), 4.47-4.36 (m, 1H), 4.15 (d, J=12.9 Hz, 2H), 3.74-3.59 (m, 1H), 3.44 (t, J=12.4 Hz, 2H), 2.85 (s, 3H), 2.08-1.95 (m, 2H), 1.77 (d, J=11.4 Hz, 2H), 1.49 (quin, J=7.4 Hz, 2H), 1.32-1.11 (m, 3H), 0.86 (t, J=7.3 Hz, 3H).

Example 3

1-(1-(6-Fluoroquinolin-4-yl)piperidin-4-yl)-1-methyl-3-(4-(trifluoromethoxy)phenyl)urea

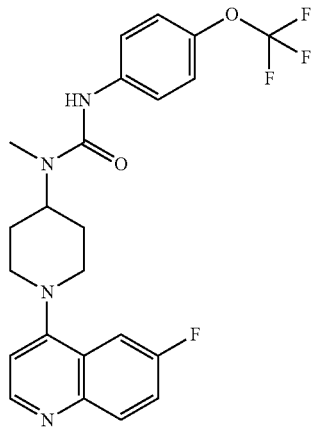 [SMILES: CN(C(=O)Nc1ccc(OC(F)(F)F)cc1)C1CCN(c2ccnc3ccc(F)cc23)CC1]

Example 3 (36.0 mg; 85% yield) was prepared following a procedure analogous to that for the synthesis of Example 1, except that by 4-(trifluoromethoxy)phenyl isocyanate (0.016 mL, 0.11 mmol) was used instead of 1-chloro-4-isocyanatobenzene. MS(ES): m/z=463 [M+H]$^+$. T$_r$=1.56 min (Method I). $^1$H NMR (500 MHz, DMSO-d$_6$) δ 8.65 (d, J=6.5 Hz, 1H), 8.54 (s, 1H), 8.05 (dd, J=8.4, 5.0 Hz, 1H), 7.94-7.85 (m, 2H), 7.55 (d, J=8.7 Hz, 2H), 7.28-7.21 (m, 3H), 4.46-4.38 (m, 1H), 4.13 (d, J=12.5 Hz, 2H), 3.65-3.38 (m, 2H), 2.88 (s, 3H), 2.09-1.99 (m, 2H), 1.81-1.75 (m, 2H).

Example 4

3-(4-Chlorophenyl)-1-(4-methoxybenzyl)-1-((1r,4r)-4-phenylcyclohexyl)urea

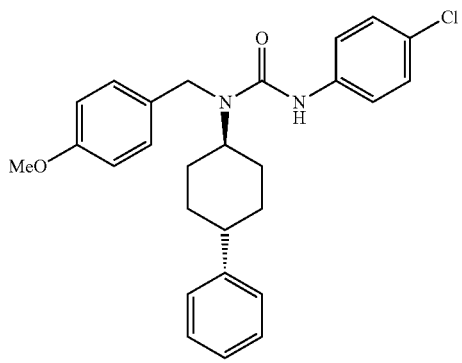

4A. trans-N-(4-Methoxybenzyl)-4-phenylcyclohexanamine

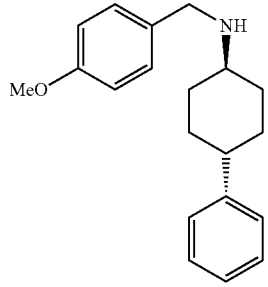

A suspension of 4-phenylcyclohexanone (2 g, 11.48 mmol) in DCM (30 mL) was treated with (4-methoxyphenyl)methanamine (1.575 g, 11.48 mmol) and magnesium perchlorate (0.128 g, 0.574 mmol). After stirring at rt for 16 h Na$_2$SO$_4$ was added and stirring continued at rt for 1 hr. The mixture was filtered washed with MeOH and the mother liquor was conc. to yield a yellow viscous oil. The oil was dissolved in MeOH (10 mL), and treated with NaBH$_4$ (0.651 g, 17.22 mmol) in portions, then stirred at rt for 30 min until the reaction was done. The reaction was quenched with water (75 ml) and extracted with EtOAc (3x). The combined organic extracts were dried, filtered, and concentrated. The yellow residue was purified on an ISCO silica column (40 g), eluting with (DCM: 10% MeOH in DCM contain 2.5% NH$_4$OH=0%-70%) in 20 mins. to yield (1r,4r)-N-(4-methoxybenzyl)-4-phenylcyclohexanamine (870 mg, 2.94 mmol, 25%)$^1$H NMR (500 MHz, chloroform-d) δ 7.32-7.22 (m, 3H), 7.22-7.10 (m, 4H), 6.92-6.77 (m, 2H), 3.84-3.70 (m, 5H), 2.60-2.46 (m, 2H), 2.15-2.02 (m, 2H), 1.97-1.82 (m, 2H), 1.49 (qd, J=12.9, 3.0 Hz, 2H), 1.36-1.15 (m, 2H) MS: Anal. Calc'd for C$_{20}$H$_{25}$NO 295.194, found [M+H] 296.1 LC: tr=1.4 min (Method I)

Example 4. 3-(4-Chlorophenyl)-1-(4-methoxybenzyl)-1-((1r,4r)-4-phenylcyclohexyl)urea To a solution of trans-N-(4-methoxybenzyl)-4-phenylcyclohexanamine (20 mg, 0.068 mmol) in THF (0.5 mL) at RT was added 1-chloro-4-isocyanatobenzene (20.79 mg, 0.135 mmol). The reaction was stirred at RT for 2 h. The crude material was purified via preparative LC/MS with the following conditions: Column: XBridge C18, 19x200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 50-100% B over 20 minutes, then a 5-minute hold at 100% B; Flow: 20 mL/min. Fractions containing the desired product were combined and dried via centrifugal evaporation. The yield of the product was 27.8 mg (0.062 mmol, 91%)$^1$H NMR (500 MHz, DMSO-d$_6$) δ 8.41 (br. s., 1H), 7.51-7.39 (m, J=8.4 Hz, 2H), 7.31-7.24 (m, 4H), 7.23-7.04 (m, 5H), 6.93-6.75 (m, J=8.2 Hz, 2H), 4.52 (br. s., 2H), 4.16 (br. s., 1H), 3.80-3.69 (m, 4H), 2.43 (br. s., 1H), 1.78 (d, J=10.4 Hz, 2H), 1.68 (br. s., 2H), 1.65-1.46 (m, 4H) MS: Anal. Calc'd for C$_{27}$H$_{29}$ClN$_2$O$_2$ 448.192, found [M+H] 449.3 LC: t$_r$=2.56 min (Method I)

These compounds were obtained following the procedures in Example 4 using the corresponding isocyanates and intermediate 4A.

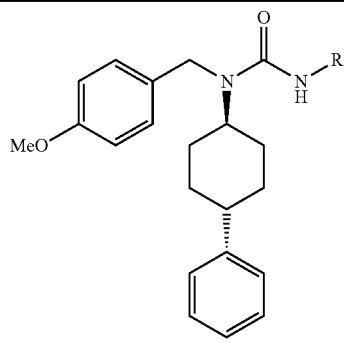

| Ex. No. | Name | R | Tr (min)$^{Method\ I}$ | [M + H]$^+$ |
|---|---|---|---|---|
| 5 | 3-(2,4-difluorophenyl)-1-(4-methoxybenzyl)-1-(trans-4-phenylcyclohexyl)urea | 2,4-difluorophenyl | 2.46 | 451.1 |
| 6 | 3-(4-chloro-2-fluorophenyl)-1-(4-methoxybenzyl)-1-(trans-4-phenylcyclohexyl)urea | 4-chloro-2-fluorophenyl | 2.6 | 467.1 |
| 7 | 1-(4-methoxybenzyl)-3-(3-phenoxyphenyl)-1-(trans-4-phenylcyclohexyl)urea | 4-phenoxyphenyl | 2.7 | 507.3 |
| 8 | 3-(3,4-difluorophenyl)-1-(4-methoxybenzyl)-1-(trans-4-phenylcyclohexyl)urea | 3,4-difluorophenyl | 2.5 | 451.3 |
| 9 | 3-(4-fluorophenyl)-1-(4-methoxybenzyl)-1-(trans-4-phenylcyclohexyl)urea | 4-fluorophenyl | 2.4 | 433.3 |
| 10 | 1-(4-methoxybenzyl)-1-(trans-4-phenylcyclohexyl)-3-(4-(trifluoromethoxy)phenyl)urea | 4-(trifluoromethoxy)phenyl | 2.6 | 499.1 |
| 11 | 1-(4-methoxybenzyl)-1-(trans-4-phenylcyclohexyl)-3-(p-tolyl)urea | p-tolyl | 2.48 | 429.2 |
| 12 | 1-(4-methoxybenzyl)-1-(trans-4-phenylcyclohexyl)-3-(4-(trifluoromethyl)phenyl)urea | 4-(trifluoromethyl)phenyl | 2.6 | 483.2 |

-continued

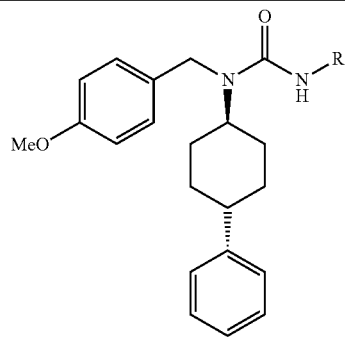

| Ex. No. | Name | R | Tr (min)$^{Method\ I}$ | [M + H]$^+$ |
|---|---|---|---|---|
| 13 | 3-(4-ethoxyphenyl)-1-(4-methoxybenzyl)-1-(trans-4-phenylcyclohexyl)urea | 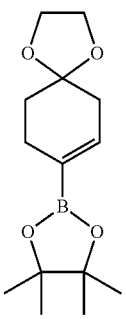 | 2.4 | 459.2 |

Example 14

3-(4-Chlorophenyl)-1-(trans-4-(6-fluoroquinolin-4-yl)cyclohexyl)-1-methylurea

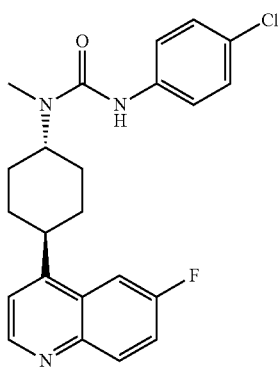 [SMILES: CN(C(=O)Nc1ccc(Cl)cc1)[C@H]1CC[C@H](c2ccnc3ccc(F)cc32)CC1]

Preparation 14A:

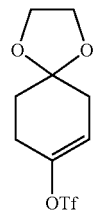

To a stirred solution of 1,4-dioxaspiro[4.5]decan-8-one (300 g, 1920.86 mmol, 1.0 eq) and phenyltrifluoromethanesulfonimide (823.47 g, 2305.03 mmol, 1.2 eq) in MTBE (7.5 L) under $N_2$ at −78° C. was added 2.0 M NaHMDS in THF (1152.2 mL, 2305.03 mmol, 1.2 eq) over 70 minutes, and the mixture was stirred for an additional 60 minutes. The reaction mixture was warmed to room temperature and stirred overnight until TLC showed complete consumption of the starting material. The mixture was quenched with aqueous $KHSO_4$ (100 ml), filtrated to remove the solid and concentrated the filtrate completely. To the residue was added 3 L MTBE, then washed with 5% NaOH (1.5 L×3). The organic phase was concentrated to obtain 567 g crude Preparation 14A (light yellow oil, yield 102%). The crude can be used directly in next step without further purification.

Preparation 14A: $^1$H NMR (400 MHz, CDCl$_3$): δ (ppm) 5.65 (t, J=4.0 Hz, 1H), 3.98 (d, J=1.5 Hz, 4H), 2.53 (s, 2H), 2.40 (s, 2H), 1.90 (t, J=6.6 Hz, 2H)

Preparation 14B:

A mixture of crude Preparation 14A (600 g, 2.08 mol, 1 eq), B$_2$Pin$_2$ (687.1 g, 2.71 mol, 1.3 eq), KOAc (613 g, 6.24 mol, 3 eq), NaBr (86 g 0.833 mol, 0.4 eq) and Pd(dppf)Cl$_2$ (76 g, 0.1 mol, 0.05 eq) in dioxane (6.5 L) was heated to reflux overnight. Once the reaction was complete, the mixture was concentrated and purified by FCC (2%→10%→20% EtOAc/PE) to give Preparation 14B (369 g, 66%).

Preparation 14B: LC-MS: 267.1 (M+1)+, $^1$H NMR (400 MHz, CDCl$_3$) δ 6.46 (s, 1H), 3.98 (s, 4H), 2.37-2.35 (m, 4H), 1.74-1.60 (t, 2H), 1.24 (s, 12H).

Preparation 14C:

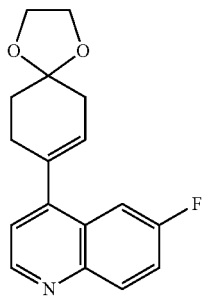 [SMILES: Fc1ccc2nccc(C3=CCC4(CC3)OCCO4)c2c1]

A mixture of Preparation 14B (368 g, 1.38 mol, 1.3 eq), 4-Chloro-6-fluoroquinoline (195 g, 1.07 mol, 1 eq), $K_2CO_3$ (445 g, 3.22 mol, 3 eq) and $Pd(PPh_3)_4$ (25 g, 22 mmol, 0.02 eq) in dioxane-water (3 L, 4:1) was heated to reflux overnight. The solution was then concentrated and extracted with EtOAc. Purification by FCC (38% EtOAc/petrolium ether) gave Preparation 14C (236 g, 77%).

Preparation 14C: LC-MS: 286.1 (M+1)+, $^1$H NMR (400 MHz, CDCl$_3$) δ 8.80-8.29 (d, 1H), 8.11-8.07 (q, 1H), 7.63-7.61 (q, 1H), 7.47-7.46 (q, 1H), 7.26-7.22 (m, 1H), 5.75-5.74 (m, 1H), 4.08-4.05 (m, 4H), 2.63-2.59 (m, 2H), 2.59-2.53 (m, 2H), 2.0-1.97 (m, 2H).

Preparation 14D:

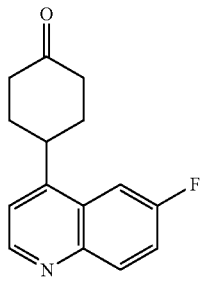 [SMILES: O=C1CCC(c2ccnc3ccc(F)cc23)CC1]

To Preparation 14C (125 g, 0.44 mol) in IPA (2 L) at 55° C. was added 10% Pd/C and the mixture was stirred under an atmosphere of H2 overnight. The mixture was filtered and concentrated to give crude Preparation 14D (130 g), which was used directly in the next step.

Preparation 14E:

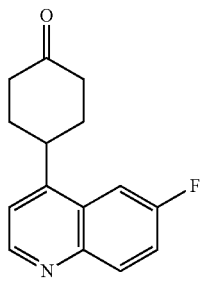 [SMILES: O=C1CCC(c2ccnc3ccc(F)cc23)CC1]

Preparation 14D (100 g, 0.348 mol) was treated with 4 N HCl (300 mL) in acetone (1200 mL) at 45° C. overnight. The mixture was monitored by TLC. Then the solution was then concentrated in vacuo. The residue was adjusted to pH 9 with 6 N NaOH and the mixture was partitioned between ethyl acetate and water. The organic layer was washed with brine, dried over anhydrous Na$_2$SO$_4$, filtered and concentrated to give light yellow solid, which was then purified by silica gel column using hexanes and ethyl acetate (from 20 percent ethyl acetate to 70% ethyl acetate) to afford Preparation 14E as a white solid, (47 g+20 g mixture, yield>55%).

Preparation 40E: LC-MS: 244.0 (M+1)+, $^1$H NMR (400 MHz, CDCl$_3$) δ 8.84 (d, J=4.6 Hz, 1H), 8.16 (dd, J=9.3, 5.7 Hz, 1H), 7.72 (dd, J=10.3, 2.8 Hz, 1H), 7.52 (ddd, J=9.2, 7.8, 2.7 Hz, 1H), 7.29 (d, J=4.6 Hz, 1H), 3.69 (ddd, J=12.1, 9.0, 3.3 Hz, 1H), 2.77-2.54 (m, 4H), 2.37 (ddd, J=13.4, 5.9, 3.0 Hz, 2H), 2.04 (qd, J=12.6, 5.3 Hz, 2H).

14F and 14G. trans-4-(6-Fluoroquinolin-4-yl)cyclohexanamine and cis-4-(6-Fluoroquinolin-4-yl)-N-methylcyclohexanamine

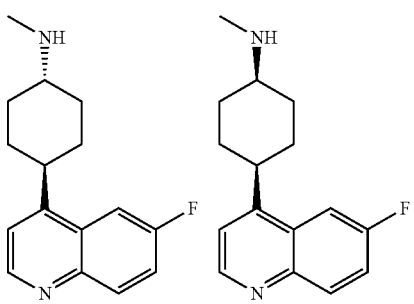

To a solution of 14E (100 mg, 0.411 mmol) and methanamine (0.822 mL, 1.644 mmol) in CH$_2$Cl$_2$ (2 mL) at RT was added acetic acid (0.024 mL, 0.411 mmol), followed by sodium triacetoxyborohydride (131 mg, 0.617 mmol). The reaction was stirred at RT for 5 h. Then it was diluted with MeOH and purified with prep HPLC (PHENOMENEX® Luna 5μ 30×100 mm), 40 mL/min flow rate with gradient of 0% B-100% B over 12 minutes Hold at 100% B for 2 min. (A: 0.1% TFA in water/MeOH (90:10), B: 0.1% TFA in water/MeOH (10:90) monitoring at 254 nm to afford 14F (65 mg, 0.127 mmol, 31%) and 14G (120 mg, 0.235, 57%).

14F: $^1$H NMR (400 MHz, DMSO-d$_6$) δ 8.88 (d, J=4.6 Hz, 1H), 8.55 (br. s., 2H), 8.20-8.03 (m, 2H), 7.73 (td, J=8.7, 2.8 Hz, 1H), 7.51 (d, J=4.6 Hz, 1H), 3.39 (br. s., 1H), 3.11 (br. s., 1H), 2.63 (t, J=5.5 Hz, 3H), 2.17 (br. s., 2H), 2.01 (d, J=7.0 Hz, 2H), 1.76-1.52 (m, 4H) MS: Anal. Calc'd for $C_{16}H_{19}FN_2$ 258.153, found [M+H] 259.1 LC: tr=0.43 min (Method A).

14G: $^1$H NMR (400 MHz, DMSO-d$_6$) δ 8.94 (d, J=4.8 Hz, 1H), 8.58 (br. s., 2H), 8.21-8.07 (m, 2H), 7.80-7.67 (m, 1H), 7.60 (d, J=4.8 Hz, 1H), 3.60-3.47 (m, 1H), 3.42 (br. s., 1H), 2.66 (t, J=5.4 Hz, 3H), 2.17-1.94 (m, 4H), 1.93-1.68 (m, 4H) MS: Anal. Calc'd for $C_{16}H_{19}FN_2$ 258.153, found [M+H] 259.1 LC: tr=0.46 min (Method A).

Example 14. 3-(4-Chlorophenyl)-1-(trans-4-(6-fluoroquinolin-4-yl)cyclohexyl)-1-methylurea To a solution of trans-4-(6-fluoroquinolin-4-yl)-N-methylcyclohexanamine (15 mg, 0.031 mmol) in THF (0.5 mL) at RT was added 1-chloro-4-isocyanatobenzene (7.11 mg, 0.046 mmol). The reaction was stirred at RT for 2 h. The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 30-70% B over 22 minutes, then a 5-minute hold at 100% B; Flow: 20 mL/min. Fractions containing the desired product were combined and dried via centrifugal evaporation. The yield of the product was 6.6 mg (0.015 mmol, 50%) $^1$H NMR (500 MHz, DMSO-$d_6$) δ 8.78 (d, J=4.4 Hz, 1H), 8.40 (s, 1H), 8.08 (dd, J=9.0, 5.9 Hz, 1H), 7.98 (d, J=8.8 Hz, 1H), 7.66 (t, J=8.5 Hz, 1H), 7.50-7.38 (m, 3H), 7.26 (d, J=8.6 Hz, 2H), 4.15 (br. s., 1H), 3.39-3.23 (m, 1H), 2.88 (s, 4H), 1.99-1.81 (m, 4H), 1.77-1.62 (m, 4H) MS: Anal. Calc'd for $C_{23}H_{23}C_1FN_3O$ 411.151, found [M+H] 412.0 LC: tr=1.45 min (Method I)

This compound was obtained following the procedures in Example 14 using the corresponding amines (14G) and the corresponding isocyanates.

| Ex. No. | Name | R | Tr (min)$^{Method\ I}$ | [M + H]$^+$ |
|---|---|---|---|---|
| 15 | 3-(4-chlorophenyl)-1-(cis-4-(6-fluoroquinolin-4-yl)cyclohexyl)-1-methylurea | 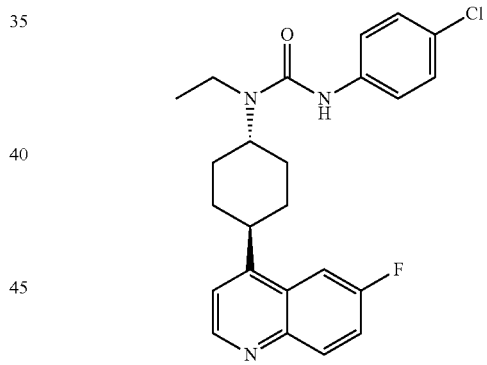 | 1.95 | 412.3 |

Example 16

3-(4-Chlorophenyl)-1-ethyl-1-(trans-4-(6-fluoroquinolin-4-yl)cyclohexyl)urea

16A. trans-N-Ethyl-4-(6-fluoroquinolin-4-yl)cyclohexanamine

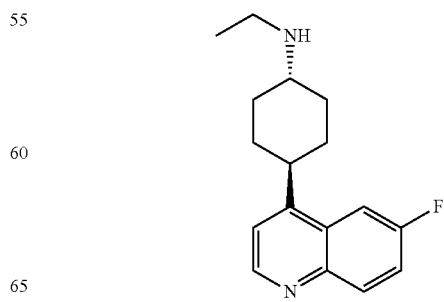

16B. cis-N-Ethyl-4-(6-fluoroquinolin-4-yl)cyclohexanamine

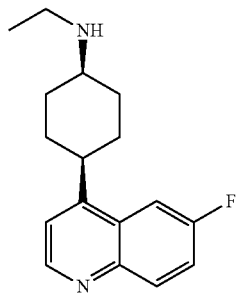 [SMILES: CCN[C@H]1CC[C@@H](c2ccnc3ccc(F)cc32)CC1]

Examples 16A and 16B were obtained following the procedures in Examples 14F and 14G using the corresponding 4-(6-fluoroquinolin-4-yl)cyclohexanone and ethanamine.

16A. $^1$H NMR (400 MHz, DMSO-$d_6$) δ 8.88 (d, J=4.6 Hz, 1H), 8.45 (br. s., 1H), 8.20-8.01 (m, 2H), 7.73 (td, J=8.7, 2.8 Hz, 1H), 7.51 (d, J=4.6 Hz, 1H), 3.38 (br. s., 1H), 3.18 (br. s., 1H), 3.06 (dd, J=12.5, 7.1 Hz, 2H), 2.18 (br. s., 2H), 2.01 (d, J=7.2 Hz, 2H), 1.76-1.56 (m, 4H), 1.24 (t, J=7.2 Hz, 3H) MS: Anal. Calc'd for $C_{17}H_{21}CFN_2$ 272.169, found [M+H] 273.1 LC: tr=0.45 min (Method A).

16B. $^1$H NMR (400 MHz, DMSO-$d_6$) δ 8.94 (d, J=4.6 Hz, 1H), 8.31 (br. s., 1H), 8.17-7.97 (m, 2H), 7.73 (td, J=8.7, 2.8 Hz, 1H), 7.57 (d, J=4.8 Hz, 1H), 3.61-3.42 (m, 2H), 3.17-2.89 (m, 2H), 2.14-1.95 (m, 4H), 1.94-1.83 (m, 2H), 1.82-1.72 (m, 2H), 1.28 (t, J=7.2 Hz, 3H) MS: Anal. Calc'd for $C_{17}H_{21}CFN_2$ 272.169, found [M+H] 273.1 LC: tr=0.48 min (Method A).

Example 16: 3-(4-Chlorophenyl)-1-ethyl-1-(trans-4-(6-fluoroquinolin-4-yl)cyclohexyl)urea Example 16 was obtained following the procedures in Example 14 using 16A and 1-chloro-4-isocyanatobenzene. $^1$H NMR (500 MHz, DMSO-$d_6$) δ 8.80 (d, J=4.4 Hz, 1H), 8.30 (s, 1H), 8.09 (dd, J=9.0, 5.8 Hz, 1H), 8.02 (d, J=10.8 Hz, 1H), 7.67 (t, J=7.6 Hz, 1H), 7.55-7.39 (m, 3H), 7.32-7.11 (m, 2H), 4.16 (br. s., 1H), 3.73-3.61 (m, 1H), 3.47-3.23 (m, 2H), 2.02-1.84 (m, 4H), 1.82-1.61 (m, 4H), 1.14 (t, J=6.9 Hz, 3H) MS: Anal. Calc'd for $C_{24}H_{25}ClFN_3O$ 425.167, found [M+H] 426.1 LC: tr=2.1 min (Method I).

This compound was obtained following the procedures in Example 14 using the corresponding amines (16B) and isocyanates.

| Ex. No. | Name | R | Tr (min)$^{Method\ I}$ | [M + H]$^+$ |
|---|---|---|---|---|
| 17 | 3-(4-chlorophenyl)-1-ethyl-1-(cis-4-(6-fluoroquinolin-4-yl)cyclohexyl)urea | 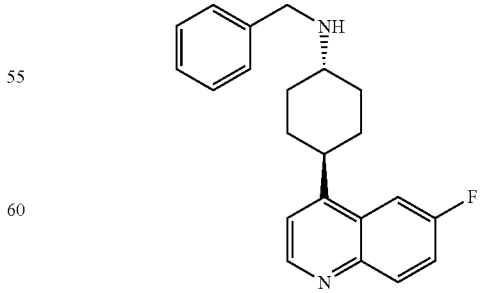 | 1.5657 | 426.3 |

Example 18

18A. trans-N-Benzyl-4-(6-fluoroquinolin-4-yl)cyclohexanamine

To a solution of 14E (100 mg, 0.411 mmol) and benzylamine (66 mg, 0.617 mmol) in $CH_2Cl_2$ (2 mL) at RT was added acetic acid (0.024 mL, 0.411 mmol), followed by sodium triacetoxyborohydride (131 mg, 0.617 mmol). The reaction was stirred at RT for 4 h. Then it was diluted with MeOH and purified with prep HPLC (Phen Luna 5 u 30×100 mm), 40 mL/min flow rate with gradient of 0% B-100% B over 12 minutes Hold at 100% B for 2 min. (A: 0.1% TFA in water/MeOH (90:10), B: 0.1% TFA in water/MeOH (10:90) monitoring at 254 nm. Evaporation of the product containing fractions gave (1r,4r)-N-benzyl-4-(6-fluoroquinolin-4-yl)cyclohexanamine (150 mg). An aliquot (15 mg) of this material was further purified under the following conditions: Column: XBridge C18, 19×200 mm, 5-m particles; Mobile Phase A: 5:95 acetonitrile:water with 10-mM ammonium acetate; Mobile Phase B: 95:5 acetonitrile:water with 10-mM ammonium acetate; Gradient: 10-50% B over 18 minutes, then a 5-minute hold at 100% B; Flow: 20 mL/min. Fractions containing the desired product were combined and dried via centrifugal evaporation. The yield of the product was 3.1 mg. In addition to the trans product, the cis product was also obtained by drying down the appropriate fractions. See 18B below.

$^1$H NMR (500 MHz, DMSO-$d_6$) δ 8.78 (br d, J=4.2 Hz, 1H), 8.08 (br dd, J=8.8, 6.0 Hz, 1H), 7.96 (br d, J=10.6 Hz, 1H), 7.72-7.62 (m, 1H), 7.43 (br d, J=7.0 Hz, 3H), 7.37 (br t, J=7.3 Hz, 2H), 7.34-7.25 (m, 1H), 3.94 (s, 1H), 3.74-3.63 (m, 1H), 3.29 (br s, 1H), 2.78 (br s, 1H), 2.14 (br s, 2H), 1.99-1.84 (m, 3H), 1.55 (br s, 4H). MS: Anal. Calc'd for $C_{22}H_{23}FN_2$ 334.185, found [M+H] 335.1 LC: tr=0.78 min (Method I).

18B. cis-N-Benzyl-4-(6-fluoroquinolin-4-yl)cyclohexanamine

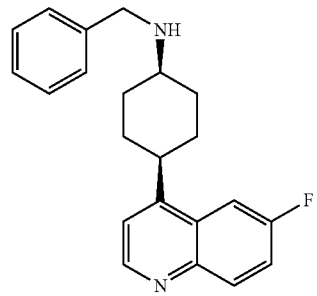 [SMILES: Fc1ccc2nccc([C@H]3CC[C@@H](NCc4ccccc4)CC3)c2c1]

Intermediate 18B was obtained following the procedures in Intermediate 18A using the corresponding 14E and benzylamine. $^1$H NMR (500 MHz, DMSO-$d_6$) δ 8.84 (d, J=3.8 Hz, 1H), 8.14-8.04 (m, 1H), 8.00 (d, J=10.8 Hz, 1H), 7.67 (t, J=8.7 Hz, 1H), 7.55-7.46 (m, 3H), 7.41 (t, J=7.2 Hz, 2H), 7.35 (d, J=7.2 Hz, 1H), 4.01 (br. s., 2H), 3.41 (br. s., 1H), 3.17 (br. s., 1H), 2.09-1.99 (m, 2H), 1.99-1.80 (m, 4H), 1.67 (d, J=12.0 Hz, 2H). MS: Anal. Calc'd for $C_{22}H_{23}FN_2$ 334.185, found [M+H] 335.2 LC: $t_r$=0.90 min (Method I).

These compounds were obtained following the procedures in Example 14 using trans-N-benzyl-4-(6-fluoroquinolin-4-yl)cyclohexanamine (Intermediate 18A) and corresponding isocyanates.

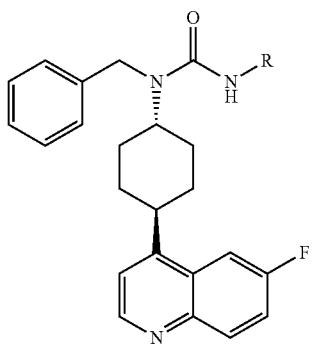

| Ex. No. | Name | R | Tr (min)$^{Method\ I}$ | [M + H]$^+$ |
|---|---|---|---|---|
| 18 | 1-benzyl-3-(4-chlorophenyl)-1-(trans-4-(6-fluoroquinolin-4-yl)cyclohexyl)urea | 4-Cl-C6H4 | 1.85 | 488.3 |
| 19 | 1-benzyl-3-(4-fluorophenyl)-1-(trans-4-(6-fluoroquinolin-4-yl)cyclohexyl)urea | 4-F-C6H4 | 1.67 | 471.9 |
| 20 | 1-benzyl-1-(trans-4-(6-fluoroquinolin-4-yl)cyclohexyl)-3-(p-tolyl)urea | 4-CH3-C6H4 | 1.81 | 468.0 |

-continued

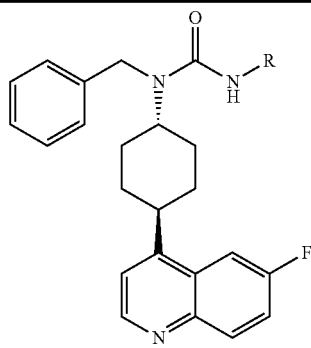

| Ex. No. | Name | R | Tr (min)$^{Method\ I}$ | [M + H]$^+$ |
|---|---|---|---|---|
| 21 | 1-benzyl-3-(4-chloro-2-fluorophenyl)-1-(trans-4-(6-fluoroquinolin-4-yl)cyclohexyl)urea | 2-F, 4-Cl phenyl | 1.92 | 506.3 |
| 22 | 1-benzyl-3-(4-cyanophenyl)-1-(trans-4-(6-fluoroquinolin-4-yl)cyclohexyl)urea | 4-CN phenyl | 1.65 | 479.3 |

These compounds were obtained following the procedures in Example 14 using cis-N-benzyl-4-(6-fluoroquinolin-4-yl)cyclohexanamine (Intermediate 18B) and corresponding isocyanates.

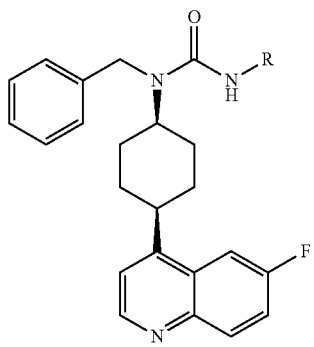

| Ex. No. | Name | R | Tr (min)$^{Method\ I}$ | [M + H]$^+$ |
|---|---|---|---|---|
| 23 | 1-benzyl-3-(4-chlorophenyl)-1-(cis-4-(6-fluoroquinolin-4-yl)cyclohexyl)urea | 4-Cl phenyl | 1.82 | 488.1 |
| 24 | 1-benzyl-3-(4-chloro-2-fluorophenyl)-1-(cis-4-(6-fluoroquinolin-4-yl)cyclohexyl)urea | 2-F, 4-Cl phenyl | 1.83 | 506.2 |

Example 25

2-(4-((3-(4-chlorophenyl)-1-(trans-4-(6-fluoroquinolin-4-yl)cyclohexyl)ureido) methyl)phenyl)acetic Acid

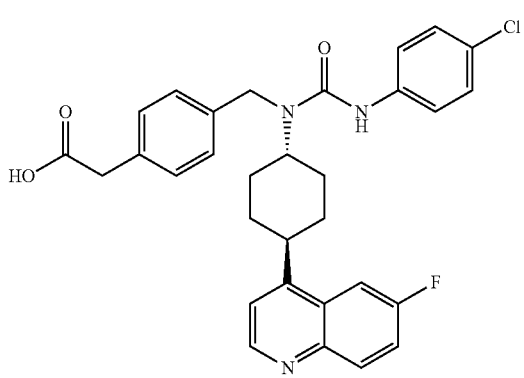 [SMILES: O=C(O)Cc1ccc(CN(C(=O)Nc2ccc(Cl)cc2)[C@H]2CC[C@H](c3ccnc4ccc(F)cc43)CC2)cc1]

25A. 2-(4-(((trans-4-(6-Fluoroquinolin-4-yl)cyclohexyl)amino)methyl)phenyl)acetic Acid

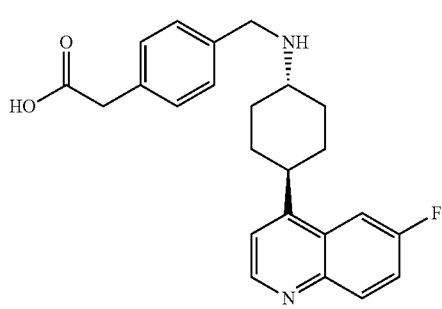 [SMILES: O=C(O)Cc1ccc(CN[C@H]2CC[C@H](c3ccnc4ccc(F)cc43)CC2)cc1]

Intermediate 25A was obtained following the procedures in Intermediate 18A using 14E and 2-(4-(aminomethyl)phenyl) acetic acid hydrochloride $^1$H NMR (500 MHz, DMSO-$d_6$) δ 8.91 (br. s., 2H), 8.83 (d, J=3.9 Hz, 1H), 8.20-8.08 (m, 1H), 8.03 (d, J=10.7 Hz, 1H), 7.71 (t, J=8.3 Hz, 1H), 7.48 (d, J=7.9 Hz, 3H), 7.35 (d, J=7.3 Hz, 2H), 4.21 (br. s., 2H), 3.60 (d, J=19.4 Hz, 2H), 3.41-3.28 (m, 1H), 3.21 (br. s., 1H), 2.28 (d, J=10.6 Hz, 2H), 2.01 (d, J=11.3 Hz, 2H), 1.81-1.59 (m, 4H) MS: Anal. Calc'd for $C_{24}H_{25}FN_2O_2$ 392.190, found [M+H]393.1 LC: tr=0.72 min (Method I).

25B. 2-(4-(((cis-4-(6-Fluoroquinolin-4-yl)cyclohexyl)amino)methyl)phenyl)acetic Acid

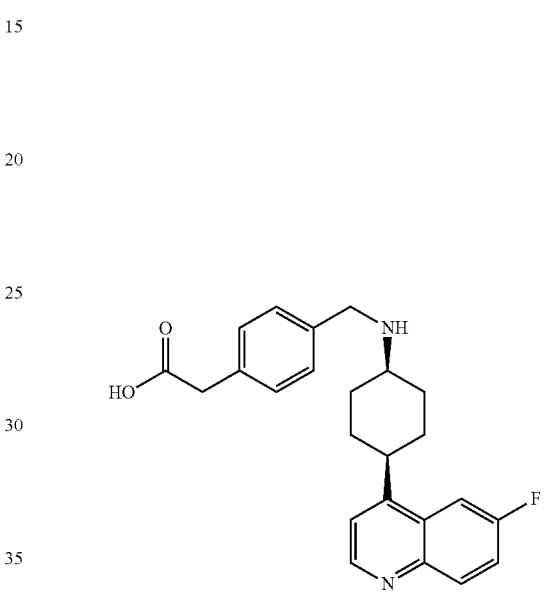

Intermediate 25B was obtained following the procedures in Intermediate 18A using 14E and 2-(4-(aminomethyl)phenyl)acetic acid hydrochloride $^1$H NMR (500 MHz, DMSO-$d_6$) δ 8.81 (d, J=4.2 Hz, 1H), 8.16-8.03 (m, 1H), 7.98 (d, J=9.6 Hz, 1H), 7.73-7.60 (m, 1H), 7.51 (d, J=4.3 Hz, 1H), 7.42-7.29 (m, J=7.6 Hz, 2H), 7.26-7.08 (m, J=7.5 Hz, 2H), 3.81 (br. s., 1H), 3.64 (br. s., 1H), 3.49 (s, 1H), 3.34 (br. s., 1H), 3.16 (s),1), 2.99 (br. s., 1H), 2.01-1.87 (m, 4H), 1.83-1.68 (m, 2H), 1.61 (d, J=11.9 Hz, 2H). MS: Anal. Calc'd for $C_{24}H_{25}FN_2O_2$ 392.190, found [M+H] 393.2 LC: tr=0.79 min (Method I).

These compounds were obtained following the procedures in Example 14 using 2-(4-(((trans-4-(6-fluoroquinolin-4-yl)cyclohexyl)amino)methyl)phenyl)acetic acid (25A) and the corresponding isocyanates.

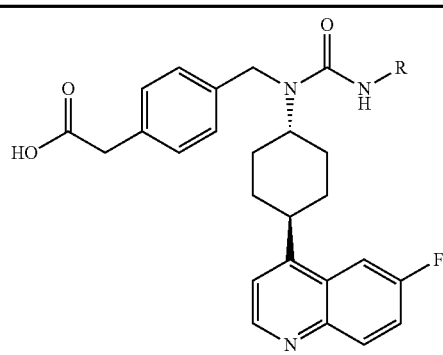

| Ex. No. | Name | R | Tr (min)$^{Method\ I}$ | [M + H]$^+$ |
|---|---|---|---|---|
| 26 | 2-(4-((3-(4-chloro-2-fluorophenyl)-1-(trans-4-(6-fluoroquinolin-4-yl)cyclohexyl)ureido)methyl)phenyl)acetic acid | 2-F, 4-Cl phenyl | 1.64 | 564.3 |
| 27 | 2-(4-((1-(trans-4-(6-fluoroquinolin-4-yl)cyclohexyl)-3-phenylureido)methyl)phenyl)acetic acid | phenyl | 1.41 | 512.4 |

30

These compounds were obtained following the procedures in Example 14 using 2-(4-(((cis-4-(6-fluoroquinolin-4-yl)cyclohexyl)amino)methyl)phenyl)acetic acid (25B) and the corresponding isocyanates.

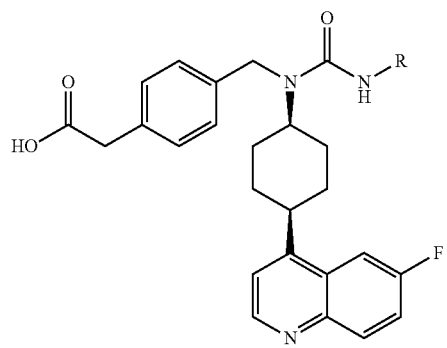

| Ex. No. | Name | R | Tr (min)$^{Method\ I}$ | [M + H]$^+$ |
|---|---|---|---|---|
| 28 | 2-(4-((3-(4-chlorophenyl)-1-(cis-4-(6-fluoroquinolin-4-yl)cyclohexyl)ureido)methyl)phenyl)acetic acid | 4-Cl phenyl | 1.63 | 546.1 |
| 29 | 2-(4-((3-(4-chloro-2-fluorophenyl)-1-(cis-4-(6-fluoroquinolin-4-yl)cyclohexyl)ureido)methyl)phenyl)acetic acid | 2-F, 4-Cl phenyl | 1.64 | 564.3 |

Example 30

3-(4-cyanophenyl)-1-(4-methoxybenzyl)-1-((1r,4r)-4-phenylcyclohexyl)urea

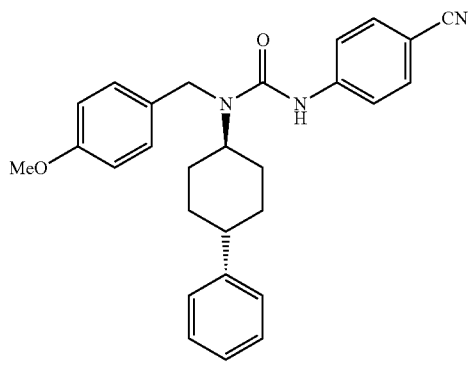

This compound was obtained following the procedures in Example 4 using the corresponding isocyanate and intermediate 4A.

Example 31

3-((S)-1-(4-chlorophenyl)ethyl)-1-(4-methoxybenzyl)-1-((1r,4S)-4-phenylcyclohexyl)urea

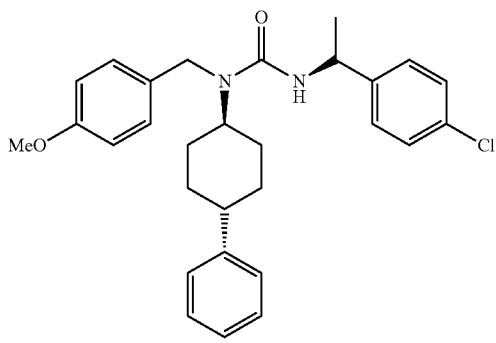

31A. (1r,4r)-N-(4-methoxybenzyl)-4-phenylcyclohexanamine

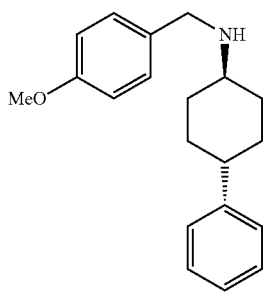

A suspension of 4-phenylcyclohexanone (2 g, 11.48 mmol) in DCM (30 mL) was treated with (4-methoxyphenyl)methanamine (1.575 g, 11.48 mmol) and magnesium perchlorate (0.128 g, 0.574 mmol). The reaction was stirred at rt for 16 h, then Na$_2$SO$_4$ was added, stirred at rt for 1 hr, and washed with MeOH. The mother liquor was conc. to yield a yellow viscous oil which was dissolved into MeOH (10 mL) and treated with NaBH$_4$ (0.651 g, 17.22 mmol) in one portion. The reaction was stirred at rt for 30 min, quenched with water (75 ml), and extracted with EtOAc (3×). The combined organic extracts were dried, filtered, concentrated. The yellow residue was purified by ISCO silica column (40 g), eluting with (DCM:10% MeOH in DCM contain 2.5% NH$_4$OH=0%-70%) in 20 mins. to yield (1r,4r)-N-(4-methoxybenzyl)-4-phenylcyclohexanamine (870 mg, 2.94 mmol, 25%) $^1$H NMR (500 MHz, CHLOROFORM-d) δ 7.32-7.22 (m, 3H), 7.22-7.10 (m, 4H), 6.92-6.77 (m, 2H), 3.84-3.70 (m, 5H), 2.60-2.46 (m, 2H), 2.15-2.02 (m, 2H), 1.97-1.82 (m, 2H), 1.49 (qd, J=12.9, 3.0 Hz, 2H), 1.36-1.15 (m, 2H) MS: Anal. Calc'd for C$_{20}$H$_{25}$NO 295.194, found [M+H] 296.1 LC: tr=1.4 min (Method A)

Example 31 ((S)-1-(4-chlorophenyl)ethyl)-1-(4-methoxybenzyl)-1-((1r,4S)-4-phenylcyclohexyl)urea To a solution of (1r,4r)-N-(4-methoxybenzyl)-4-phenylcyclohexanamine (15 mg, 0.027 mmol) in THF (0.5 mL) at RT was added (R)1-chloro-4-isocyanatobenzene (9.69 mg, 0.053 mmol), followed by Hunig's base (0.019 mL, 0.107 mmol). The reaction was stirred at RT for 2 h. The crude material was purified via preparative LC/MS with the following conditions: Column: XBridge C18, 19×200 mm, 5-m particles; Mobile Phase A: 5:95 acetonitrile:water with 10-mM ammonium acetate; Mobile Phase B: 95:5 acetonitrile:water with 10-mM ammonium acetate; Gradient: 50-100% B over 20 minutes, then a 5-minute hold at 100% B; Flow: 20 mL/min. Fractions containing the desired product were combined and dried via centrifugal evaporation. The yield of the product was 8.0 mg (0.015 mmol, 56.5%) $^1$H NMR (500 MHz, DMSO-d$_6$) δ 8.74 (d, J=4.4 Hz, 1H), 8.05 (dd, J=9.1, 5.9 Hz, 1H), 7.82 (d, J=9.2 Hz, 1H), 7.63 (t, J=8.6 Hz, 1H), 7.39 (d, J=4.4 Hz, 1H), 7.35-7.12 (m, 7H), 6.59 (d, J=7.2 Hz, 1H), 4.86 (t, J=7.1 Hz, 1H), 4.46 (br. s., 2H), 4.12 (br. s., 1H), 3.78-3.68 (m, 3H), 3.63 (br. s., 1H), 2.04 (br. s., 1H), 1.99 (br. s., 2H), 1.92 (d, J=19.6 Hz, 3H), 1.54 (br. s., 5H), 1.31 (d, J=7.1 Hz, 3H) MS: [M+H] 516.3 LC: tr=1.88 min (Method A)

Examples 32 and 33 were obtained following the procedures in Example 31 using the corresponding isocyanates.

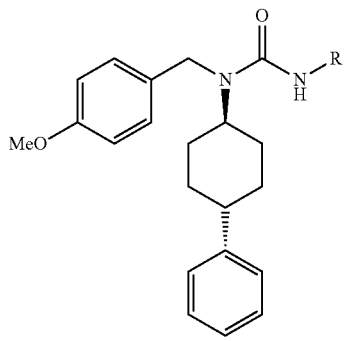

| Example | Name | R | Tr (min)$^{MethodA}$ | [M + H]$^+$ |
|---|---|---|---|---|
| 32 | 3-(4-fluorobenzyl)-1-(4-methoxybenzyl)-1-((1r,4r)-4-phenylcyclohexyl)urea | 4-fluorobenzyl | 2.4 | 447.3 |
| 33 | 3-((R)-1-(4-fluorophenyl)ethyl)-1-(4-methoxybenzyl)-1-((1r,4R)-4-phenylcyclohexyl)urea | (R)-1-(4-fluorophenyl)ethyl | 2.48 | 461.4 |

Example 34

1-((S)-1-(4-chlorophenyl)ethyl)-3-((1r,4S)-4-(6-fluoroquinolin-4-yl)cyclohexyl)urea

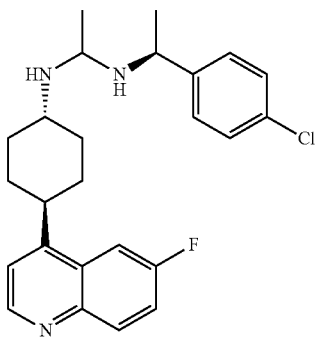 [SMILES: CC(N[C@@H](C)c1ccc(Cl)cc1)N[C@H]1CC[C@H](c2ccnc3ccc(F)cc32)CC1]

34A. (1r,4r)-4-(6-fluoroquinolin-4-yl)cyclohexanamine

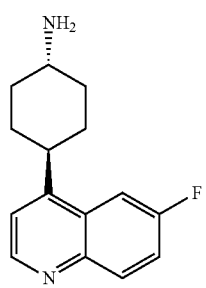 [SMILES: N[C@H]1CC[C@H](c2ccnc3ccc(F)cc32)CC1]

To a solution of Preparation 14E (4-(6-fluoroquinolin-4-yl)cyclohexanone 350 mg, 1.439 mmol) in EtOH (6 mL) in a microwave vial was added ammonium acetate (1663 mg, 21.58 mmol) followed by sodium cyanoborohydride (108 mg, 1.726 mmol). The reaction was capped and microwaved at 130° C. for 5 min. The reaction was cooled to RT and diluted with MeOH and purified with prep HPLC (Phen Luna 5 u 30×100 mm), 40 mL/min flow rate with gradient of 0% B-100% B over 12 minutes Hold at 100% B for 2 min. (A: 0.1% TFA in water/MeOH (90:10), B: 0.1% TFA in water/MeOH (10:90) monitoring at 254 nm. Fractions containing the product were combined and concentrated to give (1r,4r)-4-(6-fluoroquinolin-4-yl)cyclohexanamine (310 mg, 0.624 mmol, 43.4% yield). In addition to the trans product, the cis product was also obtained by concentrating the appropriate fractions. See 35A below. 1H NMR (400 MHz, DMSO-d6) δ 8.88 (d, J=4.6 Hz, 1H), 8.19-8.05 (m, 2H), 7.92 (br. s., 3H), 7.73 (td, J=8.7, 2.8 Hz, 1H), 7.53 (d, J=4.6 Hz, 1H), 3.36 (br. s., 1H), 3.22-3.02 (m, 1H), 2.09 (br. s., 2H), 1.96 (br. s., 2H), 1.77-1.52 (m, 4H) MS: Anal. Calc'd for $C_{15}H_{17}FN_2$ 244.138, found [M+H] 245.1 LC: tr=0.42 min (Method B)

Example 34: ((S)-1-(4-chlorophenyl)ethyl)-3-((1r,4S)-4-(6-fluoroquinolin-4-yl)cyclohexyl)urea Example 34 was obtained following the procedures in Example 14 using (1r,4r)-4-(6-fluoroquinolin-4-yl)cyclohexanamine (34A) and corresponding isocyanates.

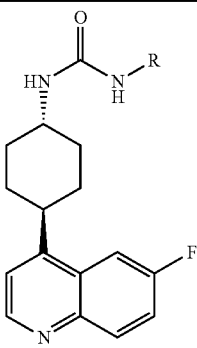

| Example | Name | R | Tr (min)$^{MethodA}$ | [M + H]$^+$ |
|---|---|---|---|---|
| 34 | 1-((S)-1-(4-chlorophenyl)ethyl)-3-((1r,4S)-4-(6-fluoroquinolin-4-yl)cyclohexyl)urea | 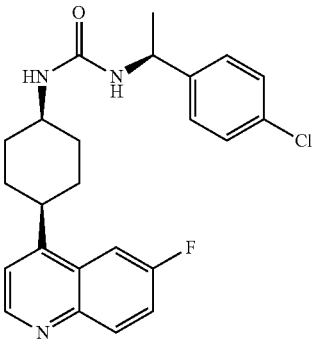 | 1.47 | 426.3 |

Example 35

1-((S)-1-(4-chlorophenyl)ethyl)-3-((1s,4R)-4-(6-fluoroquinolin-4-yl)cyclohexyl)urea

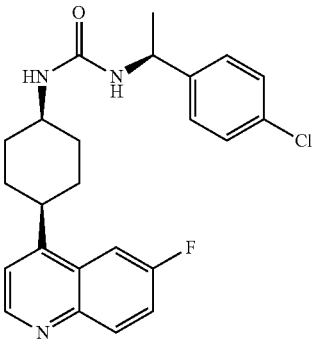 [SMILES: C[C@H](NC(=O)N[C@H]1CC[C@@H](c2ccnc3ccc(F)cc32)CC1)c1ccc(Cl)cc1]

35A.
(1s,4s)-4-(6-fluoroquinolin-4-yl)cyclohexanamine

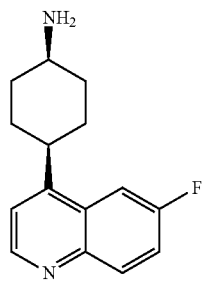 [SMILES: N[C@H]1CC[C@@H](c2ccnc3ccc(F)cc32)CC1]

To a solution of 14E (4-(6-fluoroquinolin-4-yl)cyclohexanone, 350 mg, 1.439 mmol) in EtOH (6 mL) in a microwave vial was added ammonium acetate (1663 mg, 21.58 mmol) followed by sodium cyanoborohydride (108 mg, 1.726 mmol). The reaction was capped and microwave at 130° C. for 5 min. The reaction was cooled to RT and diluted with MeOH and purified with prep HPLC (Phen Luna 5 u 30×100 mm), 40 mL/min flow rate with gradient of 0% B-100% B over 12 minutes Hold at 100% B for 2 min. (A: 0.1% TFA in water/MeOH (90:10), B: 0.1% TFA in water/MeOH (10:90) monitoring at 254 nm. Fractions containing the product were combined and concentrated to give (1s,4s)-4-(6-fluoroquinolin-4-yl)cyclohexanamine (100 mg, 0.201 mmol, 14% yield)$^1$H NMR (400 MHz, DMSO-d$_6$) δ 8.94 (d, J=4.6 Hz, 1H), 8.19-8.03 (m, 2H), 7.94 (br. s., 1H), 7.74 (td, J=8.7, 2.8 Hz, 1H), 7.60 (d, J=4.8 Hz, 1H), 3.59 (br. s., 1H), 3.49 (t, J=11.0 Hz, 1H), 2.10-1.82 (m, 6H), 1.75 (d, J=10.8 Hz, 2H) MS: Anal. Calc'd for C$_{15}$H$_{17}$FN$_2$ 244.138, found [M+H] 245.1 LC: tr=0.45 min (Method A)

Example 35: 1-((S)-1-(4-chlorophenyl)ethyl)-3-((1s,4R)-4-(6-fluoroquinolin-4-yl)cyclohexyl)urea To a solution of 34A ((1s,4s)-4-(6-fluoroquinolin-4-yl)cyclohexanamine, 15 mg, 0.061 mmol) in THF (0.5 mL) at RT was added (R)-1-chloro-4-(1-isocyanatoethyl)benzene (22.30 mg, 0.123 mmol). The reaction was stirred at RT for 2 h. The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 30-70% B over 22 minutes, then a 5-minute hold at 100% B; Flow: 20 mL/min. Fractions containing the desired product were combined and dried via centrifugal evaporation. The yield of the product was 9.8 mg (0.023 mmol, 37%)$^1$H NMR (500 MHz, DMSO-d$_6$) δ 8.88 (d, J=4.6 Hz, 1H), 8.12 (dd, J=9.1, 5.8 Hz, 1H), 8.03 (d, J=10.7 Hz, 1H), 7.72 (t, J=8.6 Hz, 1H), 7.52 (d, J=4.4 Hz, 1H), 7.42-7.27 (m, 5H), 7.19 (s, 1H), 7.09 (s, 1H), 4.72 (t, J=6.6 Hz, 1H), 3.87 (br. s., 1H), 3.36 (br. s., 1H), 1.78 (d, J=17.9 Hz, 3H), 1.69 (br. s., 5H), 1.30 (d, J=6.8 Hz, 3H) MS: [M+H] 426.2 LC: tr=1.35 min (Method B)

Example 36

3-((S)-1-(4-chlorophenyl)ethyl)-1-((1r,4S)-4-(6-fluoroquinolin-4-yl)cyclohexyl)-1-methylurea

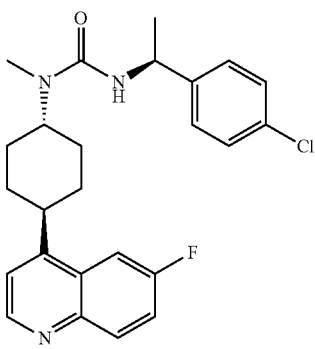 [SMILES: C[C@H](NC(=O)N(C)[C@H]1CC[C@H](c2ccnc3ccc(F)cc32)CC1)c1ccc(Cl)cc1]

36A:
(1r,4r)-4-(6-fluoroquinolin-4-yl)cyclohexanamine

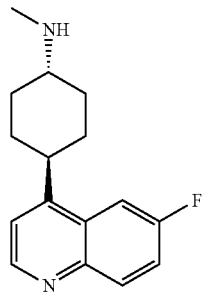 [SMILES: CN[C@H]1CC[C@H](c2ccnc3ccc(F)cc32)CC1]

To a solution of 14E (4-(6-fluoroquinolin-4-yl)cyclohexanone, 100 mg, 0.411 mmol) and methanamine (0.822 mL, 1.644 mmol) in CH$_2$Cl$_2$ (2 mL) at RT was added acetic acid (0.024 mL, 0.411 mmol), followed by sodium triacetoxyborohydride (131 mg, 0.617 mmol). The reaction was stirred at RT for 5 h. Then it was diluted with MeOH and purified with prep HPLC (Phen Luna 5 u 30×100 mm), 40 mL/min flow rate with gradient of 0% B-100% B over 12 minutes Hold at 100% B for 2 min. (A: 0.1% TFA in water/MeOH (90:10), B: 0.1% TFA in water/MeOH (10:90) monitoring at 254 nm to afford 36A (65 mg, 0.127 mmol, 31%) $^1$H NMR (400 MHz, DMSO-d$_6$) δ 8.88 (d, J=4.6 Hz, 1H), 8.55 (br. s., 2H), 8.20-8.03 (m, 2H), 7.73 (td, J=8.7, 2.8 Hz, 1H), 7.51 (d, J=4.6 Hz, 1H), 3.39 (br. s., 1H), 3.11 (br. s., 1H), 2.63 (t, J=5.5 Hz, 3H), 2.17 (br. s., 2H), 2.01 (d, J=7.0 Hz, 2H), 1.76-1.52 (m, 4H) MS: Anal. Calc'd for C$_{16}$H$_{19}$FN$_2$ 258.153, found [M+H] 259.1 LC: tr=0.43 min (Method B)

Example 36 was obtained following the procedures in Example 31 using (1r,4r)-4-(6-fluoroquinolin-4-yl)cyclohexanamine (36A) and the corresponding isocyanates.

| Example | Name | R | Tr (min)$^{Method\ B}$ | [M + H]$^+$ |
|---|---|---|---|---|
| 36 | 3-((S)-1-(4-chlorophenyl)ethyl)-1-((1r,4S)-4-(6-fluoroquinolin-4-yl)cyclohexyl)-1-methylurea | 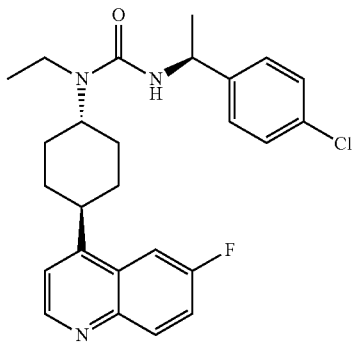 | 1.52 | 440.0 |

Example 37

3-((S)-1-(4-chlorophenyl)ethyl)-1-ethyl-1-((1r,4S)-4-(6-fluoroquinolin-4-yl)cyclohexyl)urea

37A. (1r,4r)-N-ethyl-4-(6-fluoroquinolin-4-yl)cyclohexanamine

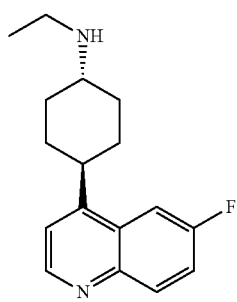 [SMILES: CCN[C@H]1CC[C@H](c2ccnc3ccc(F)cc32)CC1]

37B. (1r,4r)-N-ethyl-4-(6-fluoroquinolin-4-yl)cyclohexanamine

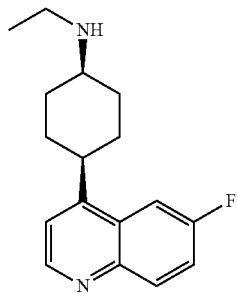 [SMILES: CCN[C@H]1CC[C@@H](c2ccnc3ccc(F)cc32)CC1]

37A and 37B were obtained following the procedures in Preparation 36A using the corresponding 14E (4-(6-fluoroquinolin-4-yl)cyclohexanone) and ethanamine.

37A: $^1$H NMR (400 MHz, DMSO-$d_6$) δ 8.88 (d, J=4.6 Hz, 1H), 8.45 (br. s., 1H), 8.20-8.01 (m, 2H), 7.73 (td, J=8.7, 2.8 Hz, 1H), 7.51 (d, J=4.6 Hz, 1H), 3.38 (br. s., 1H), 3.18 (br. s., 1H), 3.06 (dd, J=12.5, 7.1 Hz, 2H), 2.18 (br. s., 2H), 2.01 (d, J=7.2 Hz, 2H), 1.76-1.56 (m, 4H), 1.24 (t, J=7.2 Hz, 3H) MS: Anal. Calc'd for $C_{17}H_{21}CFN_2$ 272.169, found [M+H] 273.1 LC: tr=0.45 min (Method B) 37B: $^1$H NMR (400 MHz, DMSO-$d_6$) δ 8.94 (d, J=4.6 Hz, 1H), 8.31 (br. s., 1H), 8.17-7.97 (m, 2H), 7.73 (td, J=8.7, 2.8 Hz, 1H), 7.57 (d, J=4.8 Hz, 1H), 3.61-3.42 (m, 2H), 3.17-2.89 (m, 2H), 2.14-1.95 (m, 4H), 1.94-1.83 (m, 2H), 1.82-1.72 (m, 2H), 1.28 (t, J=7.2 Hz, 3H) MS: Anal. Calc'd for $C_{17}H_{21}CFN_2$ 272.169, found [M+H] 273.1 LC: tr=0.48 min (Method B)

Example 37 and Example 38 were obtained following the procedures in Example 14 using the corresponding amines (37A or 37B) and isocyanates.

| Example | Name | R | Tr (min)$^{Method\ A}$ | [M + H]$^+$ |
|---|---|---|---|---|
| 37 | 3-((S)-1-(4-chlorophenyl)ethyl)-1-ethyl-1-((1r,4S)-4-(6-fluoroquinolin-4-yl)cyclohexyl)urea | | 1.63 | 454.2 |
| 38 | 3-((S)-1-(4-chlorophenyl)ethyl)-1-ethyl-1-((1s,4R)-4-(6-fluoroquinolin-4-yl)cyclohexyl)urea | | 1.65 | 454.3 |

Example 39

1-benzyl-3-((S)-1-(4-chlorophenyl)ethyl)-1-((1r,4S)-4-(6-fluoroquinolin-4-yl)cyclohexyl)urea

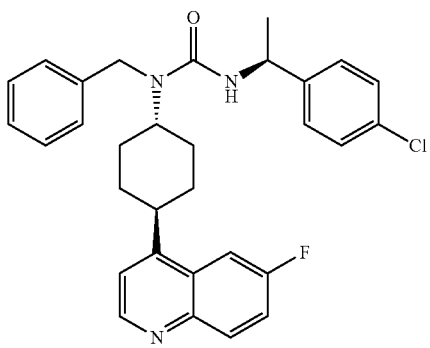 [SMILES: C[C@H](NC(=O)N(Cc1ccccc1)[C@H]1CC[C@H](c2ccnc3ccc(F)cc32)CC1)c1ccc(Cl)cc1]

39A: (1r,4r)-N-benzyl-4-(6-fluoroquinolin-4-yl)cyclohexanamine

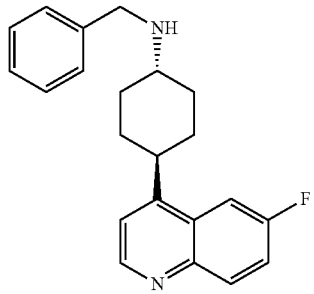 [SMILES: Fc1ccc2nccc([C@H]3CC[C@H](NCc4ccccc4)CC3)c2c1]

Intermediate 39A was obtained following the procedures in Preparation 36A using the corresponding 14E (4-(6-fluoroquinolin-4-yl)cyclohexanone) and benzylamine. $^1$H NMR (500 MHz, DMSO-$d_6$) δ 8.78 (d, J=4.2 Hz, 1H), 8.08 (dd, J=8.8, 6.0 Hz, 1H), 7.96 (d, J=10.6 Hz, 1H), 7.70-7.57 (m, 1H), 7.47-7.25 (m, 8H), 3.94 (s, 2H), 3.74-3.61 (m, 1H), 3.29 (br. s., 1H), 2.78 (br. s., 1H), 2.14 (br. s., 3H), 1.96-1.80 (m, 4H), 1.60 (br. s., 1H), 1.55 (br. s., 4H) MS: Anal. Calc'd for $C_{22}H_{23}FN_2$ 334.185, found [M+H] 335.1 LC: tr=0.78 min (Method A).

Example 39 and Example 40 were obtained following the procedures in Example 14 using (1r,4r)-N-benzyl-4-(6-fluoroquinolin-4-yl)cyclohexanamine (39A) and the corresponding isocyanates.

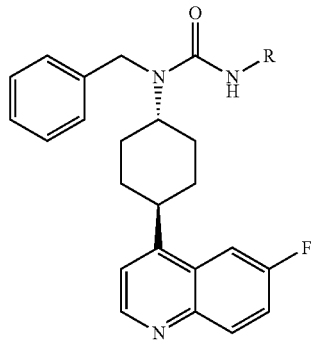

| Example | Name | R | Tr (min)$^{Method\ A}$ | [M + H]$^+$ |
|---|---|---|---|---|
| 39 | 1-benzyl-3-((S)-1-(4-chlorophenyl)ethyl)-1-((1r,4S)-4-(6-fluoroquinolin-4-yl)cyclohexyl)urea | 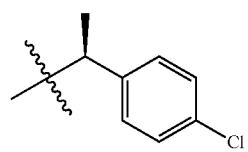 [SMILES: *[C@@H](C)c1ccc(Cl)cc1] | 1.89 | 516.1 |
| 40 | 1-benzyl-3-((R)-1-(4-fluorophenyl)ethyl)-1-((1r,4R)-4-(6-fluoroquinolin-4-yl)cyclohexyl)urea | 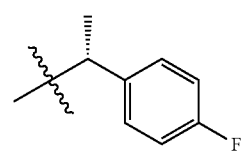 [SMILES: *[C@H](C)c1ccc(F)cc1] | 1.83 | 499.9 |

Example 41

2-(4-((3-((R)-1-(4-fluorophenyl)ethyl)-1-((1r,4R)-4-(6-fluoroquinolin-4-yl)cyclohexyl)ureido)methyl)phenyl)acetic Acid

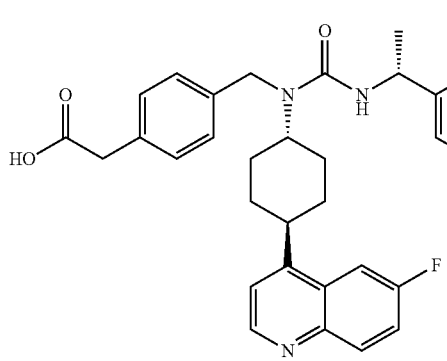

41A: 2-(4-((((1r,4r)-4-(6-fluoroquinolin-4-yl)cyclohexyl)amino)methyl)phenyl)acetic Acid

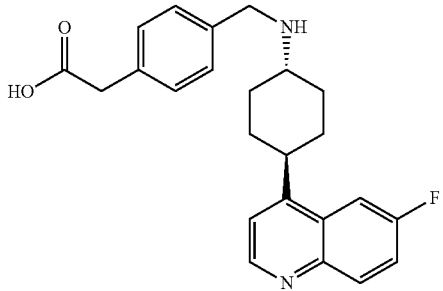 [SMILES: O=C(O)Cc1ccc(CN[C@H]2CC[C@H](c3ccnc4ccc(F)cc43)CC2)cc1]

41A was obtained following the procedures in Preparation 36A using 14E (4-(6-fluoroquinolin-4-yl)cyclohexanone) and 2-(4-(aminomethyl)phenyl)acetic acid hydrochloride. $^1$H NMR (500 MHz, DMSO-$d_6$) δ 8.91 (br. s., 2H), 8.83 (d, J=3.9 Hz, 1H), 8.20-8.08 (m, 1H), 8.03 (d, J=10.7 Hz, 1H), 7.71 (t, J=8.3 Hz, 1H), 7.48 (d, J=7.9 Hz, 3H), 7.35 (d, J=7.3 Hz, 2H), 4.21 (br. s., 2H), 3.60 (d, J=19.4 Hz, 2H), 3.41-3.28 (m, 1H), 3.21 (br. s., 1H), 2.28 (d, J=10.6 Hz, 2H), 2.01 (d, J=11.3 Hz, 2H), 1.81-1.59 (m, 4H) MS: Anal. Calc'd for $C_{24}H_{25}FN_2O_2$ 392.190, found [M+H] 393.1 LC: tr=0.72 min (Method A)

Example 41 was obtained following the procedures in Example 34 using 2-(4-((((1r,4r)-4-(6-fluoroquinolin-4-yl)cyclohexyl)amino)methyl)phenyl)acetic acid (Intermediate 25A) and the corresponding isocyanates.

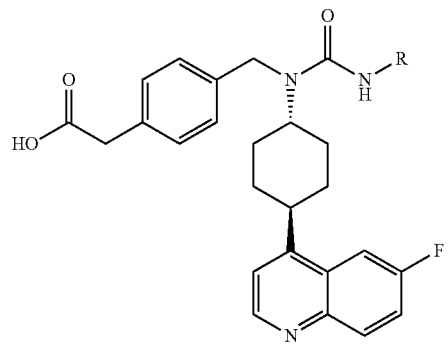

| Example | Name | R | Tr (min)$^{Method\ A}$ | [M + H]$^+$ |
|---|---|---|---|---|
| 41 | 2-(4-((3-((R)-1-(4-fluorophenyl)ethyl)-1-((1r,4R)-4-(6-fluoroquinolin-4-yl)cyclohexyl)ureido)methyl)phenyl)acetic acid | | 1.52 | 558.5 |

Example 42

3-((R)-1-(4-fluorophenyl)ethyl)-1-((1r,4R)-4-(6-fluoroquinolin-4-yl)cyclohexyl)-1-((R)-1-phenylethyl)urea

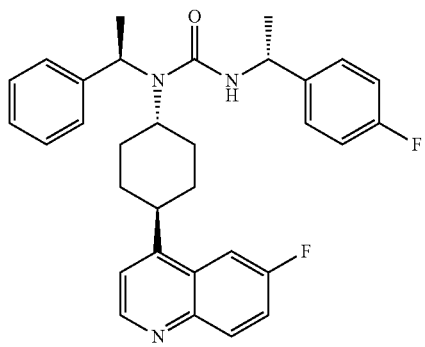 [SMILES: C[C@H](c1ccccc1)N(C(=O)N[C@H](C)c1ccc(F)cc1)[C@H]1CC[C@H](c2ccnc3ccc(F)cc32)CC1]

42A: (1r,4R)-4-(6-fluoroquinolin-4-yl)-N—((R)-1-phenylethyl)cyclohexanamine

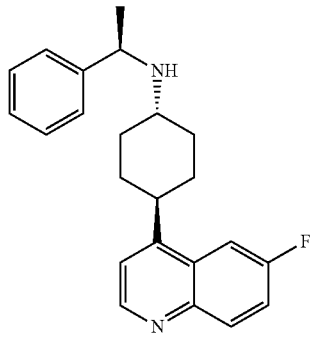 [SMILES: C[C@@H](N[C@H]1CC[C@H](c2ccnc3ccc(F)cc32)CC1)c1ccccc1]

42A was obtained following the procedures in Preparation 36A using 14E (4-(6-fluoroquinolin-4-yl)cyclohexanone) and (R)-1-phenylethanamine $^1$H NMR (500 MHz, DMSO-$d_6$) δ 8.74 (d, J=4.5 Hz, 1H), 8.07 (dd, J=9.0, 5.8 Hz, 1H), 7.93 (d, J=8.8 Hz, 1H), 7.71-7.57 (m, 1H), 7.46-7.31 (m, 7H), 7.28-7.21 (m, 1H), 4.03 (d, J=6.3 Hz, 1H), 3.65-3.46 (m, 2H), 3.24 (br. s., 1H), 2.37 (br. s., 1H), 2.14 (br. s., 1H), 1.90 (s, 5H), 1.84 (d, J=12.6 Hz, 3H), 1.51-1.35 (m, 5H), 1.29 (d, J=6.4 Hz, 3H) LC-MS: [M+H] 349.2 LC: tr=0.58 min (Method A)

Example 42 was obtained following the procedures in Example 14 using (1r,4R)-4-(6-fluoroquinolin-4-yl)-N—((R)-1-phenylethyl)cyclohexanamine (Intermediate 42A) and the corresponding isocyanates.

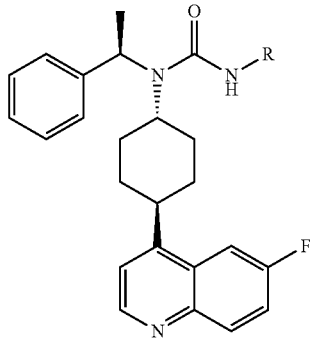

| Example | Name | R | Tr (min)$^{Method\ A}$ | [M + H]$^+$ |
|---|---|---|---|---|
| 42 | 3-((R)-1-(4-fluorophenyl)ethyl)-1-((1r,4R)-4-(6-fluoroquinolin-4-yl)cyclohexyl)-1-((R)-1-phenylethyl)urea | (structure with 4-fluorophenyl) | 1.92 | 514.3 |

Analytical HPLC/MS was performed using the following methods for Examples 43-45:

Method A:
Waters Acquity SDS using the following method: Linear Gradient of 2% to 98% solvent B over 1.7 min; UV visualization at 220 nm; Column: BEH C18 2.1 mm×50 mm; 1.7 μm particle (Heated to Temp. 50° C.); Flow rate: 0.8 ml/min; Mobile phase A: 100% Water, 0.05% TFA; Mobile phase B: 100% Acetonitrile, 0.05% TFA.

Method B:
Column: Waters Acquity UPLC BEH C18, 2.1×50 mm, 1.7-μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0-100% B over 3 minutes, then a 0.75-minute hold at 100% B; Flow: 1.00 mL/min; Detection: UV at 220 nm.

Method C:
Column: Waters Acquity UPLC BEH C18, 2.1×50 mm, 1.7-μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0-100% B over 3 minutes, then a 0.75-minute hold at 100% B; Flow: 1.0 mL/min; Detection: UV at 220 nm.

Example 43

3-cyclohexyl-1-(4-methoxybenzyl)-1-((1r,4r)-4-phenylcyclohexyl)urea

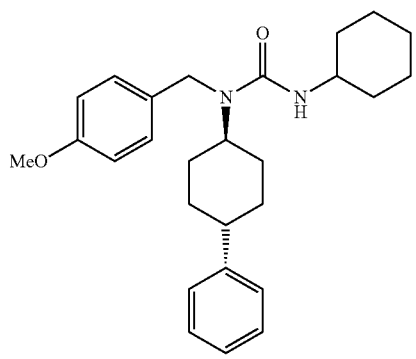

43A: (1r,4r)-N-(4-methoxybenzyl)-4-phenylcyclohexanamine

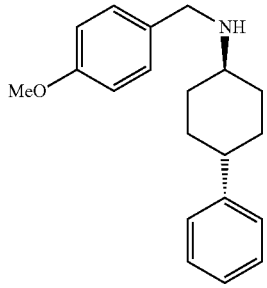

A suspension of 4-phenylcyclohexanone (2 g, 11.48 mmol) in DCM (30 mL) was treated with (4-methoxyphenyl)methanamine (1.575 g, 11.48 mmol) and magnesium perchlorate (0.128 g, 0.574 mmol), stirred at rt for 16 h, then $Na_2SO_4$ was added, stirred at rt for 1 hr, washed with MeOH, the mother liquor was conc. to yield yellow viscous oil which was dissolved into MeOH (10 mL), and treated with $NaBH_4$ (0.651 g, 17.22 mmol) in portion, stirred at rt for 30 min reaction was done, quenched with water (75 ml), extracted with EtOAc (3×), combined organic extractes was dried, filtered, concentrated. The yellow residue was purified by ISCO silica column (40 g), eluted with (DCM:10% MeOH in DCM contain 2.5% $NH_4OH$=0%-70%) in 20 mins. to yield (1r,4r)-N-(4-methoxybenzyl)-4-phenylcyclohexanamine (870 mg, 2.94 mmol, 25%) $^1$H NMR (500 MHz, CHLOROFORM-d) δ 7.32-7.22 (m, 3H), 7.22-7.10 (m, 4H), 6.92-6.77 (m, 2H), 3.84-3.70 (m, 5H), 2.60-2.46 (m, 2H), 2.15-2.02 (m, 2H), 1.97-1.82 (m, 2H), 1.49 (qd, J=12.9, 3.0 Hz, 2H), 1.36-1.15 (m, 2H) MS: Anal. Calc'd for $C_{20}H_{25}NO$ 295.194, found [M+H] 296.1 LC: tr=1.4 min (Method C)

Example 43: 3-cyclohexyl-1-(4-methoxybenzyl)-1-((1r,4r)-4-phenylcyclohexyl)urea

To a solution of (1r,4r)-N-(4-methoxybenzyl)-4-phenylcyclohexanamine (10 mg, 0.034 mmol) in THF (0.5 mL) at RT was added isocyanatocyclohexane (8.47 mg, 0.068 mmol). The reaction was stirred at RT for 2 h. The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 50-100% B over 20 minutes, then a 5-minute hold at 100% B; Flow: 20 mL/min. Fractions containing the desired product were combined and dried via centrifugal evaporation. The yield of the product was 12.0 mg (0.029 mmol, 84%) $^1$H NMR (500 MHz, DMSO-$d_6$) δ 7.31-7.22 (m, 2H), 7.21-7.09 (m, 5H), 6.86 (d, J=8.4 Hz, 2H), 4.35 (s, 2H), 4.04 (br. s., 1H), 3.74-3.55 (m, 3H), 3.45 (br. s., 1H), 2.39 (br. s., 1H), 1.80-1.65 (m, 4H), 1.64-1.41 (m, 8H), 1.25-1.01 (m, 5H) MS: [M+H] 421.4 LC: tr=2.54 min (Method C)

These compounds were obtained following the procedures in Example 43 using the corresponding isocyanates and Intermediate 43A.

| Example | Name | R | Tr (min)[Method C] | [M + H]+ |
|---|---|---|---|---|
| 44 | 3-cyclopentyl-1-(4-methoxybenzyl)-1-((1r,4r)-4-phenylcyclohexyl)urea | cyclopentyl | 2.38 | 407.2 |

-continued

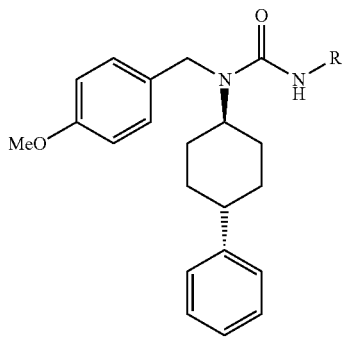

| Example | Name | R | Tr (min)$^{Method\ C}$ | [M + H]$^+$ |
|---|---|---|---|---|
| 45 | 3-cyclopropyl-1-(4-methoxybenzyl)-1-((1r,4r)-4-phenylcyclohexyl)urea | | 2.18 | 379.3 |

Materials and Methods

The following general materials and methods were used, where indicated, or may be used in the Examples below:

Standard methods in molecular biology are described in the scientific literature (see, e.g., Sambrook et al., *Molecular Cloning*, Third Edition, Cold Spring Harbor Laboratory Press, Cold Spring Harbor, N.Y. (2001); and Ausubel et al., *Current Protocols in Molecular Biology*, Vols. 1-4, John Wiley and Sons, Inc. New York, N.Y. (2001), which describes cloning in bacterial cells and DNA mutagenesis (Vol. 1), cloning in mammalian cells and yeast (Vol. 2), glycoconjugates and protein expression (Vol. 3), and bioinformatics (Vol. 4)).

The scientific literature describes methods for protein purification, including immunoprecipitation, chromatography, electrophoresis, centrifugation, and crystallization, as well as chemical analysis, chemical modification, post-translational modification, production of fusion proteins, and glycosylation of proteins (see, e.g., Coligan et al., *Current Protocols in Protein Science*, Vols. 1-2, John Wiley and Sons, Inc., NY (2000)).

Software packages and databases for determining, e.g., antigenic fragments, leader sequences, protein folding, functional domains, glycosylation sites, and sequence alignments, are available (see, e.g., GCG® Wisconsin Package (Accelrys, Inc., San Diego, Calif.); and DECYPHER® (TimeLogic Corp., Crystal Bay, Nev.).

The literature is replete with assays and other experimental techniques that can serve as a basis for evaluation of the compounds described herein.

An IDO enzyme assay and cellular production of kynurenine (KYN) is described in Sarkar, S. A. et al., *Diabetes*, 56:72-79 (2007). Briefly, all chemicals can be purchased from Sigma-Aldrich (St. Louis, Mo.) unless specified otherwise. Groups of 1,000 human islets can be cultured for 24 h in 1 mL medium with cytokines, recovered by centrifugation for 5 min at 800×g and sonicated in 150 µL PBS containing a protease inhibitor cocktail (Set 2; Calbiochem, EMD Biosciences, San Diego, Calif.). The sonicate can be centrifuged for 10 min at 10,000×g, and the supernatant can be assayed in triplicate by incubating a 40 µl sample with an equal volume of 100 mmol/L potassium phosphate buffer, pH 6.5, containing 40 mmol/L ascorbic acid (neutralized to pH 7.0), 100 µmol/L methylene blue, 200 µg/mL catalase, and 400 µmol/l L-Trp for 30 min at 37° C. The assay can be terminated by the addition of 16 µL 30% (w/v) trichloroacetic acid (TCA) and further incubated at 60° C. for 15 min to hydrolyze N-formylkynurenine to KYN. The mixture can then be centrifuged at 12,000 rpm for 15 min, and KYN can be quantified by mixing equal volume of supernatant with 2% (w/v) Ehrlich's reagent in glacial acetic acid in 96-well microtiter plate and reading the absorbance at 480 nm using L-KYN as standard. Protein in the islet samples can be quantified by Bio-Rad Protein assay at 595 nm. For the detection of L-KYN in the islet culture supernatants, proteins can be precipitated with 5% (w/v) TCA and centrifuged at 12,000 rpm for 15 min, and determination of KYN in the supernatant with Ehrlich's reagent can be determined as described above. IL-4 (10 µg/mL; 500-2,000 units/mL) and 1-α-methyl Trp (1-MT; 40 µmol/L) can be added to the incubation media as indicated. This assay can also form the basis of a cell-based assay, and may be quantified via LCMS/MS as an alternative to UV/Vis detection.

Western Blot Analyses.

Groups of 1,000-1,200 islets incubated for 24 h in Miami medium in the presence of cytokines can be harvested and sonicated in PBS as above, and 50 µg protein samples can be electrophoresed on 10% SDS-PAGE gels. COS7 cells (0.6×10$^6$ cells/60 mm3 petri dish) transfected with human-IDO plasmid (3 µg) or empty vector cells can be used as positive and negative controls, respectively. Proteins can be transferred electrophoretically onto polyvinylidine fluoride membranes by semidry method and blocked for 1 h with 5% (w/v) nonfat dry milk in Tris-buffered saline and 0.1% Tween and then incubated overnight with anti-human mouse IDO antibody (1:500; Chemicon, Temecula, Calif.), -66-harmaco-STAT$_{1\alpha}$ p91, and STAT$_{1\alpha}$ p91 (1:500; Zymed, San Francisco, Calif.). Immunoreactive proteins can be visualized with ECL PLUS® Western blotting detection reagent (Amersham BioSciences, Buckinghamshire, U.K.) after incubation for 1 h with anti-mouse horseradish peroxidase-conjugated secondary antibody (Jackson Immunolabs, West Grove, Pa.).

Immunohistochemical Detection of IDO.

Islets can be fixed in 4% paraformaldehyde in PBS (Invitrogen) for 1 h, immobilized in molten 10% porcine skin gelatin blocks (37° C.), and embedded in optimal cutting temperature compound. Immunofluorescent staining on islet tissue can be performed on 7 µm sections that were stained with antibodies raised against pancreatic duodenal homeobox 1 (PDX1) and IDO. Antigen retrieval can be performed in a water bath for 30 min in a buffer containing 10 mmol/l Tris and 1 mmol/l EDTA (pH 9.0) at 97° C. The sections can be blocked for 1 h with 5% normal goat serum in PBS. The tissues can then be reacted with mouse monoclonal anti-human IDO antibody (1:20; Chemicon) and goat polyclonal anti-human PDX1 antibody (1:2,000; which may be requested from Dr. Chris Wright, School of Medicine, Vanderbilt, Tenn.) overnight at room temperature in a humid chamber. Secondary antibodies anti-goat (labeled with Cy3) and anti-mouse (labeled with Cy2) can be purchased from Jackson Immunolabs and can be used at a concentration of 1:200. The nuclei can be stained with Hoechst 33258 (Molecular Probes, Eugene, Oreg.). Images can be acquired by Intelligent Imaging System software from an Olympus 1X81 inverted motorized microscope equipped with Olympus DSU (spinning disk confocal) and Hamamatsu ORCA IIER monochromatic CCD camera.

Alternative means for evaluating the IDO inhibitors of the present invention are described in WO 2010/0233166 and are summarized hereafter.

Biochemical Assay.

cDNA clones for both human and mouse IDO have been isolated and verified by sequencing and are commercially available. In order to prepare IDO for biochemical studies, C-terminal His-tagged IDO protein can be produced in *E. coli* using the IPTG-inducible pET5a vector system and isolated over a nickel column. The yield of the partially purified protein can be verified by gel electrophoresis and the concentration estimated by comparison to protein standards. To assay IDO enzymatic activity, a 96-well plate spectrophotometric assay for kynurenine production can be run following published procedures (see, e.g., Littlejohn, T. K. et al., *Prot. Exp. Purif,* 19:22-29 (2000)). To screen for IDO inhibitory activity, compounds can be evaluated at a single concentration of, for example, 200 µM against 50 ng of IDO enzyme in 100 µL reaction volumes with tryptophan added at increasing concentrations at, for example, 0, 2, 20, and 200 µM. Kynurenine production can be measured at 1 hour.

Cell-Based Assay.

COS-1 cells can be transiently transfected with a CMV promoter-driven plasmid expressing IDO cDNA using Lipofectamine 2000 (Invitrogen) as recommended by the manufacturer. A companion set of cells can be transiently transfected with TDO-expressing plasmid. Forty-eight hours post-transfection, the cells can be apportioned into a 96-well format at $6 \times 10^4$ cells per well. The following day, the wells can be washed and new media (phenol red free) containing 20 µg/mL tryptophan can be added together with inhibitor. The reaction can be stopped at 5 hours and the supernatant removed and spectrophotometrically-assayed for kynurenine as previously described for the enzyme assay. To obtain initial confirmation of IDO activity, compounds can be evaluated at a single concentration of, for example, 100 µM. More extensive dose-escalation profiles can be collected for select compounds.

Pharmacodynamic and Pharmacokinetic Evaluation.

A -67-harmacodynamics assay can be based on measuring serum levels of both kynurenine and tryptophan, and calculating the kynurenine/tryptophan ratio provides an estimate of IDO activity that is independent of baseline tryptophan levels. Serum tryptophan and kynurenine levels can be determined by HPLC analysis, and serum compound levels can optionally also be determined in the same HPLC run.

Compounds can be initially evaluated by challenging mice with LPS and then subsequently administering a bolus dose of compound at the time that the serum kynurenine level plateaus. As the kynurenine pool is rapidly turned over with a half-life in serum of less than 10 minutes, pre-existing kynurenine is not expected to unduly mask the impact that an IDO inhibitor has on kynurenine production. Each experiment can include non-LPS-exposed mice (to determine baseline kynurenine levels against which to compare the other mice) and a set of LPS-exposed mice dosed with vehicle alone (to provide a positive control for IDO activation). Each compound can initially be evaluated in mice at a single high i.p. bolus dose in the range of at least 100 mg/kg. Blood can be collected at defined time intervals (for example, 50 µL sample at 5, 15, 30 min., 1, 2, 4, 6, 8, and 24 hr. following compound administration) for HPLC analysis of kynurenine and tryptophan levels (-67-harmacodynamics analysis) as well as for the level of compound (pharmacokinetic analysis). From the pharmacokinetic data the peak serum concentration of compound achieved can be determined as well as the estimated rate of clearance. By comparing the level of compound in serum relative to the kynurenine/tryptophan ratio at various time points, the effective $IC_{50}$ for IDO inhibition in vivo can be roughly estimated. Compounds exhibiting efficacy can be evaluated to determine a maximum dose that achieves 100% IDO inhibition at the peak concentration.

Evaluation of Biological Activity

Exemplary compounds were tested for inhibition of IDO activity. Experimental procedures and results are provided below.

HEK293 cells were transfected with a pCDNA-based mammalian expression vector harboring human IDO1 cDNA (NM 002164.2) by electroporation. They were cultured in medium (DMEM with 10% FBS) containing 1 mg/ml G418 for two weeks. Clones of HEK293 cells that stably expressed human IDO1 protein were selected and expanded for IDO inhibition assay.

The human IDO1/HEK293 cells were seeded at 10,000 cells per 50 µL per well with RPMI/phenol red free media contains 10% FBS in a 384-well black wall clear bottom tissue culture plate (Matrix Technologies LLC) 100 nL of certain concentration of compound was then added to each well using ECHO liquid handling systems. The cells were incubated for 20 hours in 37° C. incubator with 5% $CO_2$.

The compound treatments were stopped by adding trichloroacetic acid (Sigma-Aldrich) to a final concentration at 0.2%. The cell plate was further incubated at 50° C. for 30 minute. The equal volume supernatant (20 µL) and 0.2% (w/v) Ehrlich reagent (4-dimethylaminobenzaldehyde, Sigma-Aldrich) in glacial acetic acid were mixed in a new clear bottom 384-well plate. This plate was then incubated at room temperature for 30 minute. The absorbance at 490 nm was measured on Envision plate reader.

Compound $IC_{50}$ values were calculated using the counts of 500 nM of a reference standard treatment as one hundred percent inhibition, and counts of no compound but DMSO treatment as zero percent inhibition.

Assessment of inhibitor activity in HeLa cell-based indoleamine 2,3-dioxygenase (IDO) assay:

HeLa (ATCC® CCL-2) cells were obtained from the ATCC® and cultured in Dulbecco's Modified Eagle Medium supplemented with 4.5 g/L glucose, 4.5 g/L L-glutamine and 4.5 g/L sodium pyruvate (#10-013-CV, Corning), 2 mM L-alanyl-L-glutamine dipeptide (#35050-061, Gibco), 100 U/mL penicillin, 100 µg/mL streptomycin (# SV30010, HyClone) and 10% fetal bovine serum (# SH30071.03 HyClone). Cells were maintained in a humidified incubator at 37° C. in 5% $CO_2$.

IDO activity was assessed as a function of kynurenine production as follows: HeLa cells were seeded in a 96-well culture plate at a density of 5,000 cells/well and allowed to equilibrate overnight. After 24 hours, the media was aspirated and replaced with media containing IFNγ (#285-IF/CF, R&D Systems) at a final concentration of 25 ng/mL. A serial dilution of each test compound was added to the cells in a total volume of 200 µL of culture medium. After a further 48 hour incubation, 170 µL of supernatant was transferred from each well to a fresh 96-well plate. 12.1 µL of 6.1N trichloroacetic acid (# T0699, Sigma-Aldrich) was added to each well and mixed, followed by incubation at 65° C. for 20 minutes to hydrolyze N-formylkynurenine, the product of indoleamine 2,3-dioxygenase, to kynurenine. The reaction mixture was then centrifuged for 10 mins at 500×g to sediment the precipitate. 100 μL of the supernatant was transferred from each well to a fresh 96-well plate. 100 μl of 2% (w/v) p-dimethylaminobenzaldehyde (#15647-7, Sigma-Aldrich) in acetic acid (# A6283, Sigma-Aldrich) was added to each well mixed and incubated at room temperature for 20 mins. Kynurenine concentrations were determined by measuring absorbance at 480 nm and calibrating against an L-kynurenine (# K8625, Sigma-Aldrich) standard curve using a SPECTRAMAX® M2e microplate reader (Molecular Devices). The percentage activity at each inhibitor concentration was determined and $IC_{50}$ values assessed using nonlinear regression.

Activity for compounds described herein is provided below, wherein potency levels are provided as follows: (Potency: IDO $IC_{50}$: A<0.1 μM; B<1 μM; C<10 μM).

Results of the IDO assays are shown in the table below.

| HEK Human IDO-1 | |
| --- | --- |
| Example No. | Bio Activity (μM) A < 0.1 μM; B < 1 μM; C < 10 μM |
| 1 | B |
| 2 | A |
| 3 | B |
| 4 | A |
| 5 | B |
| 6 | |
| 7 | B |
| 8 | B |
| 9 | B |
| 10 | B |
| 12 | A |
| 13 | B |
| 14 | A |
| 15 | B |
| 16 | A |
| 17 | B |
| 18 | A |
| 19 | A |
| 20 | B |
| 21 | B |
| 22 | C |
| 23 | B |
| 24 | A |
| 25 | B |
| 26 | A |
| 27 | A |
| 28 | C |
| 29 | |
| 30 | |
| 31 | B |
| 32 | C |
| 33 | A |
| 34 | B |
| 35 | B |
| 36 | B |
| 37 | B |
| 38 | |
| 39 | C |
| 40 | B |
| 41 | A |
| 42 | |
| 43 | A |
| 44 | B |
| 45 | B |

What is claimed:

1. A compound of formula I or formula II

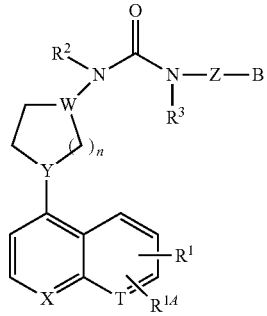

(I)

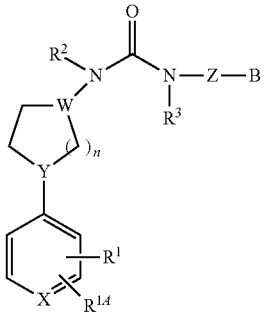

(II)

wherein
X is CH or N;
T is CH or N;
$R^1$ is H, halo, or $C_1$-$C_6$haloalkyl;
$R^{1A}$ is H, halo, or $C_1$-$C_6$haloalkyl;
Y is CH or N;
W is —CH—, —C($C_1$-$C_6$alkyl)-, or N;
n is 0, 1, 2, 3, or 4;
Z is a bond or $C_1$-$C_6$alkylene optionally substituted with one, two, or three $R^4$ substituents independently selected from $C_1$-$C_6$alkyl;
$R^2$ is -alkaryl optionally substituted with —$OC_1$-$C_6$alkyl, —$C_1$-$C_6$alkCOOH, or —$C_1$-$C_6$alkCOOC$_1$-$C_6$alkyl;
$R^3$ is H or $C_1$-$C_6$alkyl;
B is aryl optionally substituted with 1, 2, or 3 substituents independently selected from —OH, $C_1$-$C_6$alkyl, $C_1$-$C_6$haloalkyl, halo, —$OC_1$-$C_6$alkyl, —CN, aryl, or —Oaryl; or
$C_3$-$C_{12}$cycloalkyl optionally substituted with 1, 2, or 3 substituents independently selected from OH, $C_1$-$C_6$alkyl, $C_1$-$C_6$haloalkyl, halo, —$OC_1$-$C_6$alkyl, —$OC_1$-$C_6$haloalkyl, —CN, aryl, or Oaryl;

or a pharmaceutically acceptable salt thereof, a stereoisomer thereof, a tautomer thereof, or a solvate thereof.

2. The compound of claim 1 that is a compound of formula I.

3. The compound of claim 1 that is a compound of formula II.

4. The compound of claim 1, wherein $R^1$ is H, F, or —$CF_3$.

5. The compound of claim 1, wherein $R^{1A}$ is H.

6. The compound of claim 1, wherein Y is CH and W is CH.

7. The compound of claim 1, wherein Y is N and W is CH.

8. The compound of claim 1, wherein n is 2.

9. The compound of claim 1, wherein Z is a bond.

10. The compound of claim 1, wherein Z is $C_1$alkylene substituted with one $C_1$-$C_6$alkyl.

11. The compound of claim 1, wherein B is aryl optionally substituted with 1, 2, or 3 substituents independently selected from —OH, $C_1$-$C_6$alkyl, $C_1$-$C_6$haloalkyl, halo, —O$C_1$-$C_6$alkyl, —O$C_1$-$C_6$haloalkyl, —CN, aryl, or —Oaryl.

12. The compound of claim 11, wherein B is phenyl optionally substituted with 1 or 2 substituents independently selected from —OH, $C_1$-$C_6$alkyl, $C_1$-$C_6$haloalkyl, halo, —O$C_1$-$C_6$alkyl, —O$C_1$-$C_6$haloalkyl, —CN, aryl, or —Oaryl.

13. The compound of claim 1, wherein B is $C_3$-$C_{12}$cycloalkyl optionally substituted with 1, 2, or 3 substituents independently selected from —OH, $C_1$-$C_6$alkyl, $C_1$-$C_6$haloalkyl, halo, —O$C_1$-$C_6$alkyl, —O$C_1$-$C_6$haloalkyl, —CN, aryl, or —Oaryl.

14. A compound that is
3-(4-Chlorophenyl)-1-(1-(6-fluoroquinolin-4-yl)piperidin-4-yl)-1-methylurea;
3-(4-Butylphenyl)-1-(1-(6-fluoroquinolin-4-yl)piperidin-4-yl)-1-methylurea;
1-(1-(6-Fluoroquinolin-4-yl)piperidin-4-yl)-1-methyl-3-(4-(trifluoromethoxy)phenyl)urea;
3-(4-Chlorophenyl)-1-(4-methoxybenzyl)-1-((1r,4r)-4-phenylcyclohexyl)urea;
3-(2,4-difluorophenyl)-1-(4-methoxybenzyl)-1-(trans-4-phenylcyclohexyl)urea;
3-(4-chloro-2-fluorophenyl)-1-(4-methoxybenzyl)-1-(trans-4-phenylcyclohexyl)urea;
1-(4-methoxybenzyl)-3-(3-phenoxyphenyl)-1-(trans-4-phenylcyclohexyl)urea;
3-(3,4-difluorophenyl)-1-(4-methoxybenzyl)-1-(trans-4-phenylcyclohexyl)urea;
3-(4-fluorophenyl)-1-(4-methoxybenzyl)-1-(trans-4-phenylcyclohexyl)urea;
1-(4-methoxybenzyl)-1-(trans-4-phenylcyclohexyl)-3-(4-(trifluoromethoxy)phenyl)urea;
1-(4-methoxybenzyl)-1-(trans-4-phenylcyclohexyl)-3-(p-tolyl)urea;
1-(4-methoxybenzyl)-1-(trans-4-phenylcyclohexyl)-3-(4-(trifluoromethyl)phenyl)urea;
3-(4-ethoxyphenyl)-1-(4-methoxybenzyl)-1-(trans-4-phenylcyclohexyl)urea;
3-(4-Chlorophenyl)-1-(trans-4-(6-fluoroquinolin-4-yl)cyclohexyl)-1-methylurea;
3-(4-chlorophenyl)-1-(cis-4-(6-fluoroquinolin-4-yl)cyclohexyl)-1-methylurea;
3-(4-Chlorophenyl)-1-ethyl-1-(trans-4-(6-fluoroquinolin-4-yl)cyclohexyl)urea;
3-(4-chlorophenyl)-1-ethyl-1-(cis-4-(6-fluoroquinolin-4-yl)cyclohexyl)urea;
1-benzyl-3-(4-chlorophenyl)-1-(trans-4-(6-fluoroquinolin-4-yl)cyclohexyl)urea;
1-benzyl-3-(4-fluorophenyl)-1-(trans-4-(6-fluoroquinolin-4-yl)cyclohexyl)urea;
1-benzyl-1-(trans-4-(6-fluoroquinolin-4-yl)cyclohexyl)-3-(p-tolyl)urea;
1-benzyl-3-(4-chloro-2-fluorophenyl)-1-(trans-4-(6-fluoroquinolin-4-yl)cyclohexyl)urea;
1-benzyl-3-(4-cyanophenyl)-1-(trans-4-(6-fluoroquinolin-4-yl)cyclohexyl)urea;
1-benzyl-3-(4-chlorophenyl)-1-(cis-4-(6-fluoroquinolin-4-yl)cyclohexyl)urea;
1-benzyl-3-(4-chloro-2-fluorophenyl)-1-(cis-4-(6-fluoroquinolin-4-yl)cyclohexyl)urea;
2-(4-((3-(4-chlorophenyl)-1-(trans-4-(6-fluoroquinolin-4-yl)cyclohexyl)ureido)methyl)phenyl)acetic acid;
2-(4-((3-(4-chloro-2-fluorophenyl)-1-(trans-4-(6-fluoroquinolin-4-yl)cyclohexyl)ureido)methyl)phenyl) acetic acid;
2-(4-((1-(trans-4-(6-fluoroquinolin-4-yl)cyclohexyl)-3-phenylureido)methyl) phenyl)acetic acid;
2-(4-((3-(4-chlorophenyl)-1-(cis-4-(6-fluoroquinolin-4-yl)cyclohexyl) ureido)methyl)phenyl)acetic acid;
2-(4-((3-(4-chloro-2-fluorophenyl)-1-(cis-4-(6-fluoroquinolin-4-yl)cyclohexyl)ureido)methyl)phenyl)acetic acid;
3-(4-cyanophenyl)-1-(4-methoxybenzyl)-1-((1 r,4r)-4-phenylcyclohexyl)urea 3-((S)-1-(4-chlorophenyl)ethyl)-1-(4-methoxybenzyl)-1-((1 r,4 S)-4-phenyl cyclohexyl)urea;
3-(4-fluorobenzyl)-1-(4-methoxybenzyl)-1-((1r,4r)-4-phenylcyclohexyl)urea;
3-((R)-1-(4-fluorophenyl)ethyl)-1-(4-methoxybenzyl)-1-((1r,4R)-4-phenylcyclohexyl)urea;
1-((S)-1-(4-chlorophenyl)ethyl)-3-((1 r,4 S)-4-(6-fluoroquinolin-4-yl)cyclohexyl)urea;
1-((S)-1-(4-chlorophenyl)ethyl)-3-((1 s,4R)-4-(6-fluoroquinolin-4-yl)cyclohexyl)urea;
3-((S)-1-(4-chlorophenyl)ethyl)-1-((1 r,4 S)-4-(6-fluoroquinolin-4-yl)cyclohexyl)-1-methylurea;
3-((S)-1-(4-chlorophenyl)ethyl)-1-ethyl-1-((1 r,4 S)-4-(6-fluoroquinolin-4-yl)cyclohexyl)urea;
3-((S)-1-(4-chlorophenyl)ethyl)-1-ethyl-1-((1 s,4R)-4-(6-fluoroquinolin-4-yl)cyclohexyl)urea;
1-benzyl-3-((S)-1-(4-chlorophenyl)ethyl)-1-((1 r,4 S)-4-(6-fluoroquinolin-4-yl)cyclohexyl)urea;
1-benzyl-3-((R)-1-(4-fluorophenyl)ethyl)-1-((1r,4R)-4-(6-fluoroquinolin-4-yl)cyclohexyl)urea;
2-(4-((3-((R)-1-(4-fluorophenyl)ethyl)-1-((1r,4R)-4-(6-fluoroquinolin-4-yl)cyclohexyl)ureido)methyl)phenyl) acetic acid;
3-((R)-1-(4-fluorophenyl)ethyl)-1-((1r,4R)-4-(6-fluoroquinolin-4-yl)cyclohexyl)-1-((R)-1-phenylethyl)urea;
3-cyclohexyl-1-(4-methoxybenzyl)-1-((1r,4r)-4-phenylcyclohexyl)urea;
3-cyclopentyl-1-(4-methoxybenzyl)-1-((1r,4r)-4-phenylcyclohexyl)urea; or
3-cyclopropyl-1-(4-methoxybenzyl)-1-((1r,4r)-4-phenylcyclohexyl)urea;
or a pharmaceutically acceptable salt thereof, a stereoisomer thereof, a tautomer thereof, or a solvate thereof.

15. A pharmaceutical composition comprising a compound of claim 1 and a pharmaceutically acceptable carrier.

16. The pharmaceutical composition of claim 15, further comprising ipilimumab, nivolumab, or pembrolizumab, or a combination thereof.

17. A method of treating cancer in a patient in need of such treatment comprising administering to the patient a therapeutically effective amount of a compound according to claim 1.

18. A pharmaceutical composition comprising a compound of claim 14 and a pharmaceutically acceptable carrier.

19. The pharmaceutical composition of claim 15, further comprising ipilimumab, nivolumab, or pembrolizumab, or a combination thereof.

20. A method of treating cancer in a patient in need of such treatment comprising administering to the patient a therapeutically effective amount of a compound according to claim 14.

* * * * *

UNITED STATES PATENT AND TRADEMARK OFFICE
CERTIFICATE OF CORRECTION

Page 1 of 1

PATENT NO. : 10,696,648 B2
APPLICATION NO. : 16/098239
DATED : June 30, 2020
INVENTOR(S) : Williams et al.

It is certified that error appears in the above-identified patent and that said Letters Patent is hereby corrected as shown below:

On the Title Page

At Column 2, Other Publications Line 1, delete "phosphatidyleinositol" and insert -- phosphatidylinositol --, therefor.

In the Claims

At Column 74, Line 49 (Claim 1), before "—CN," insert -- —OC$_1$-C$_6$haloalkyl, --.

At Column 74, Line 52 (Claim 1), delete "OH," and insert -- —OH, --, therefor.

At Column 74, Line 54 (Claim 1), delete "Oaryl;" and insert -- —Oaryl; --, therefor.

At Column 76, Line 13 (Claim 14), delete "((1 r,4r)" and insert -- ((1r,4r) --, therefor.

At Column 76, Lines 15-16 (Claim 14), delete "((1 r,4 S)-4-phenyl cyclohexyl)urea;" and insert -- ((1r,4S)-4-phenylcyclohexyl)urea; --, therefor.

At Column 76, Line 21 (Claim 14), delete "((1 r,4 S)" and insert -- ((1r,4S) --, therefor.

At Column 76, Line 23 (Claim 14), delete "((1 s,4R)" and insert -- ((1s,4R) --, therefor.

At Column 76, Line 25 (Claim 14), delete "((1 r,4 S)" and insert -- ((1r,4S) --, therefor.

At Column 76, Line 27 (Claim 14), delete "((1 r,4 S)" and insert -- ((1r,4S) --, therefor.

At Column 76, Line 29 (Claim 14), delete "((1 s,4R)" and insert -- ((1s,4R) --, therefor.

At Column 76, Line 31 (Claim 14), delete "((1 r,4 S)" and insert -- ((1r,4S) --, therefor.

Signed and Sealed this
Second Day of February, 2021

Drew Hirshfeld
*Performing the Functions and Duties of the
Under Secretary of Commerce for Intellectual Property and
Director of the United States Patent and Trademark Office*